United States Patent
Crowe, Jr. et al.

(10) Patent No.: US 11,992,520 B2
(45) Date of Patent: May 28, 2024

(54) HUMAN MONOCLONAL ANTIBODIES TO STAPHYLOCOCCAL AUREUS ISD PROTEINS AND USES THEREOF

(71) Applicant: Vanderbilt University, Nashville, TN (US)

(72) Inventors: James E. Crowe, Jr., Nashville, TN (US); Eric Skaar, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 73 days.

(21) Appl. No.: 17/276,361

(22) PCT Filed: Sep. 6, 2019

(86) PCT No.: PCT/US2019/049843
§ 371 (c)(1),
(2) Date: Mar. 15, 2021

(87) PCT Pub. No.: WO2020/060771
PCT Pub. Date: Mar. 26, 2020

(65) Prior Publication Data
US 2022/0080036 A1    Mar. 17, 2022

Related U.S. Application Data

(60) Provisional application No. 62/732,824, filed on Sep. 18, 2018.

(51) Int. Cl.
| | | |
|---|---|---|
| A61K 39/40 | (2006.01) | |
| A61K 39/02 | (2006.01) | |
| A61K 39/085 | (2006.01) | |
| A61P 31/04 | (2006.01) | |
| G01N 33/569 | (2006.01) | |
| A61K 39/00 | (2006.01) | |

(52) U.S. Cl.
CPC ............ A61K 39/085 (2013.01); A61P 31/04 (2018.01); G01N 33/56938 (2013.01); A61K 2039/505 (2013.01); A61K 2039/575 (2013.01)

(58) Field of Classification Search
None
See application file for complete search history.

(56) References Cited

U.S. PATENT DOCUMENTS

| | | |
|---|---|---|
| 2007/0218069 A1 | 9/2007 | Gordon et al. |
| 2010/0004324 A1 | 1/2010 | Skaar et al. |
| 2013/0034559 A1 | 2/2013 | Queva et al. |
| 2013/0230531 A1 | 9/2013 | Gurnett-Bander et al. |

FOREIGN PATENT DOCUMENTS

WO    WO 2018/165089    9/2013

OTHER PUBLICATIONS

Ferrara et al (Mabs. Feb. 2015. 7(1): 32-41).*
Edwards et al (J. Mol. Biol. 2003. 334: 103-118).*
Pascalis et al. The Journal of Immunology (2002) 169, 3076-3084.*
Casset et al. (2003) BBRC 307, 198-205.*
Lloyd et al (Protein Engineering, Design and Selection. 2009. 22(3): 159-168).*
Brown et al., "Selection and characterization of murine monoclonal antibodies to Staphylococcus aureus iron-regulated surface determinant B with functional activity in vitro and in vivo", Clin. Vaccine Immunol., 16:1095-1104, 2009.
Diep et al., "Improved Protection in a Rabbit Model of Community-Associated Methicillin-Resistant Staphylococcus aureus Necrotizing Pneumonia upon Neutralization of Leukocidins in Addition to Alpha-Hemolysin," ASM Journals, 60(10):6333-6340, 2016.
Ebert et al., A fully human monoclonal antibody to Staphylococcus aureus iron regulated surface determinant B (IsdB) with functional activity in vitro and in vivo, Hum Antibodies, 19:113-128, 2010.
Ghasemzadeh-Moghaddam et al., "Humoral immune consequences of Staphylococcus aureus ST239-associated bacteremia", Eur J Clin Microbiol Infect Dis., 17:1-9, 2017.
Harro et al., "Safety and Immunogenicity of a Novel Staphylococcus aureus Vaccine: Results from the First Study of the Vaccine Dose Range in Humans", Clin. Vaccine Immunol., 17:1868-1874, 2010.
Moustafa et al., "Phase IIa Study of the Immunogenicity and Safety of the Novel Staphylococcus aureus Vaccine V710 in Adults with End-Stage Renal Disease Receiving Hemodialysis", Clin Vaccine Immunol., 19:1509-1516, 2012.
Pancari et al., "Characterization of the mechanism of protection mediated by CS-D7, a monoclonal antibody to Staphylococcus aureus iron regulated surface determinant B (IsdB)", Front Cell Infect Microbiol., 2:36, 2012.
PCT International Search Report and Written Opinion issued in International Application No. PCT/US2019/049843, dated Jan. 23, 2020.
Pishchany et al., "IsdB-dependent Hemoglobin Binding Is Required for Acquisition of Heme by Staphylococcus aureus", J Infect Dis., 209:1764-1772, 2014.
Torres et al., "Staphylococcus aureus IsdB Is a Hemoglobin Receptor Required for Heme Iron Utilization", Journal of Bacteriology, 188:8421-8429, 2006.
Verkaik et al., "Induction of antibodies by Staphylococcus aureus nasal colonization in young children", Clin Microbiol Infect., 16:1312-1317, 2010.
Vu et al., "Adaptive immune response to lipoproteins of Staphylococcus aureus in healthy subjects", Proteomics, 16:2667-2677, 2016.

* cited by examiner

Primary Examiner — Jennifer E Graser
(74) Attorney, Agent, or Firm — Parker Highlander PLLC

(57) ABSTRACT

The present disclosure is directed to antibodies binding to and inhibiting S. aureus and methods for use thereof.

18 Claims, 10 Drawing Sheets
Specification includes a Sequence Listing.

FIG. 1

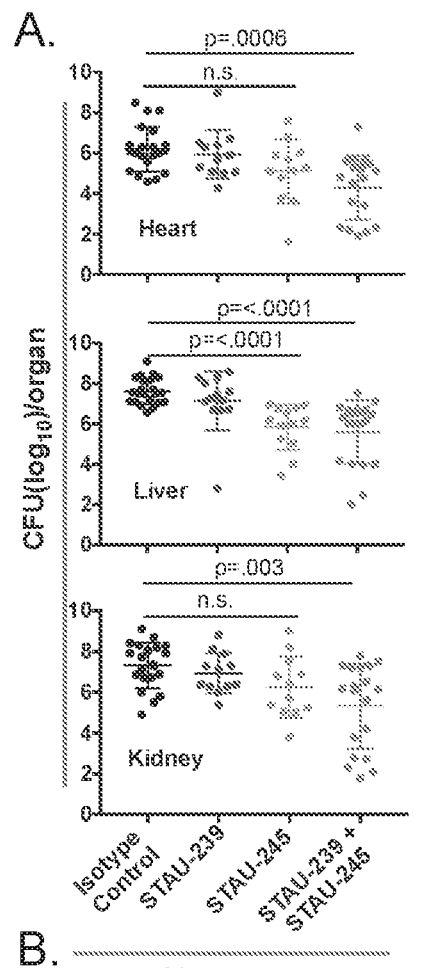
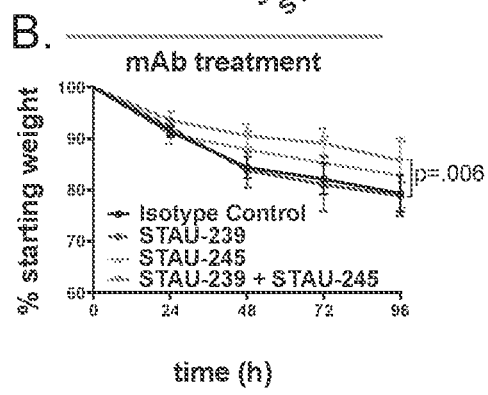
FIGS. 2A-B

A.
⁶¹VSQATSQPINFQVQKDGSSEKSHMDD⁸⁶
⁸⁷YMQHPGKVIKQNNKYYFQAVLNNASF¹¹²
¹¹³WKEYKFYNANNQELATTVVNDDKKAD¹³⁸
¹³⁹TRTINVAVEPGYKSLTTKVHIVVPQINY¹⁶⁶
¹⁶⁷NHRYTTHLEFEKAIPTLAD¹⁸⁵
B.
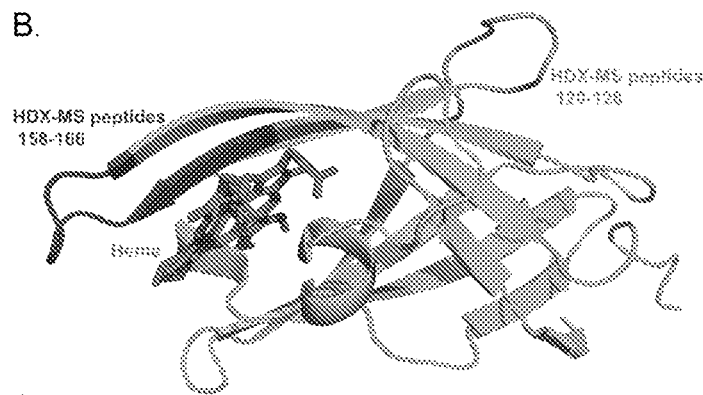
C.
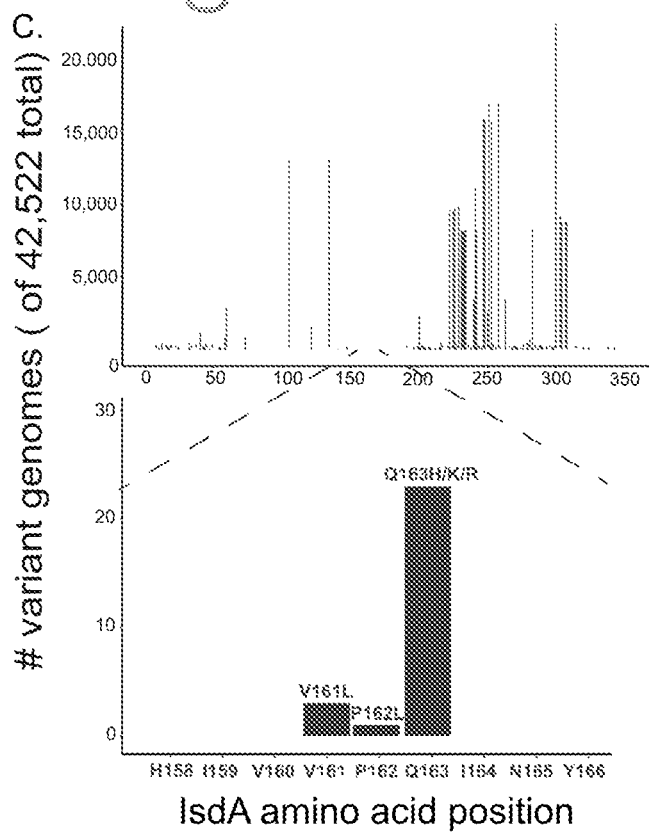
FIGS. 4A-C

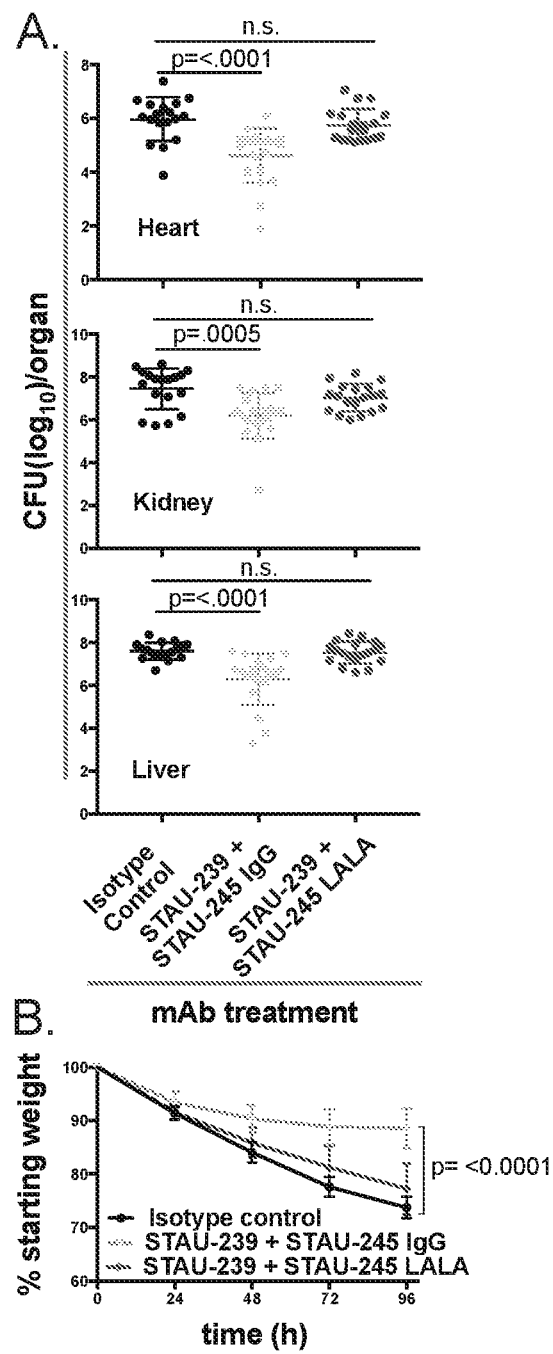
FIGS. 5A-B

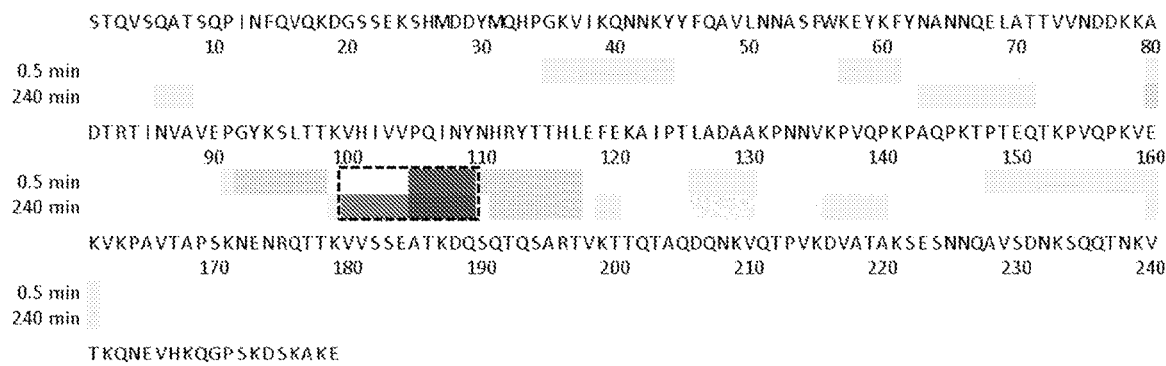
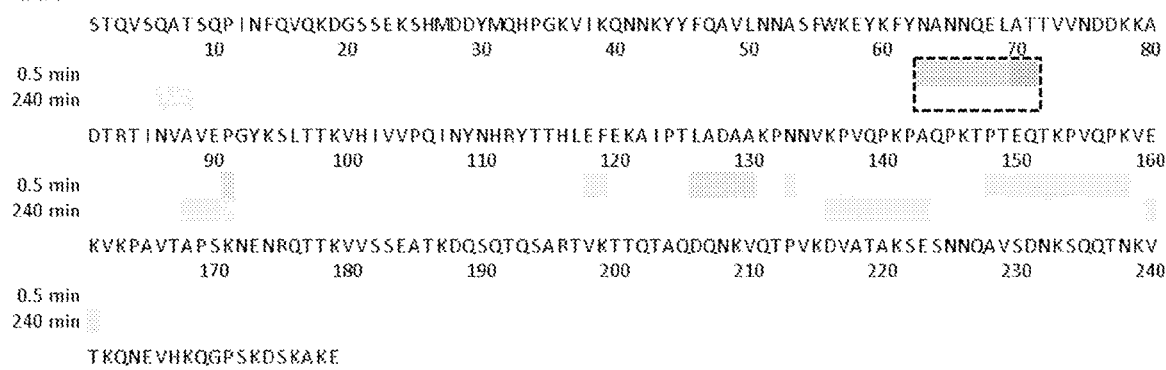
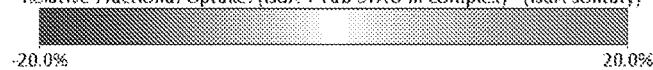
FIG. 7A

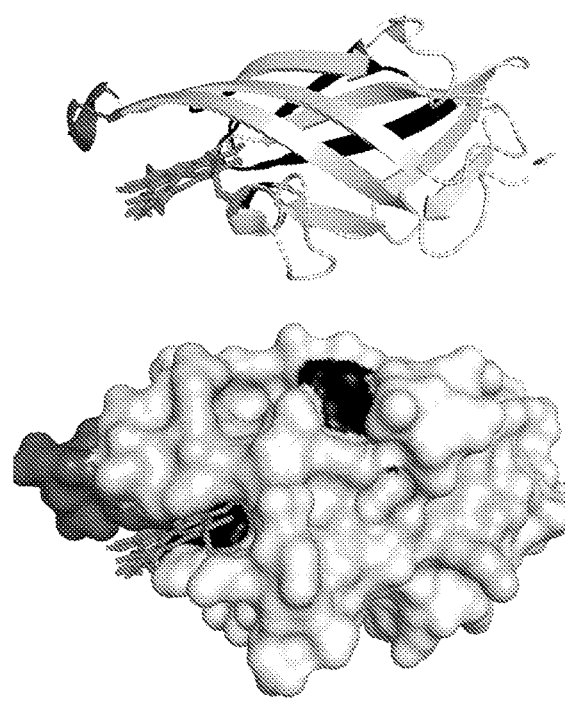 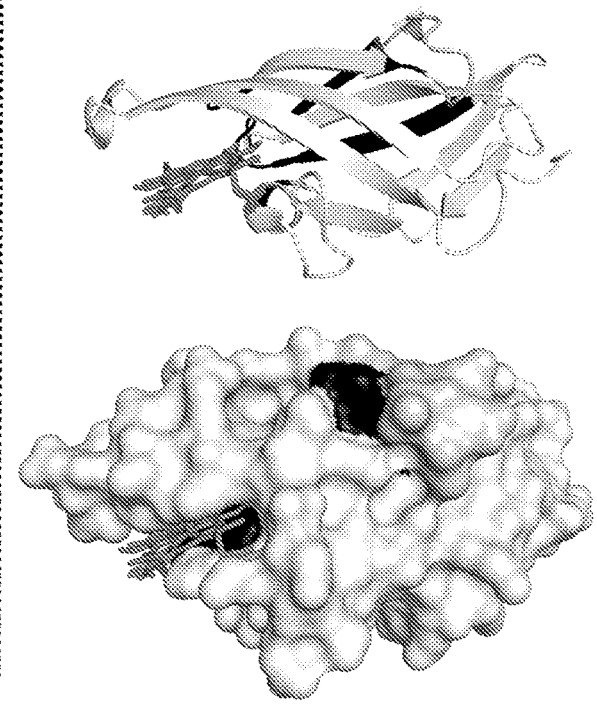
FIG. 7B  FIG. 7C
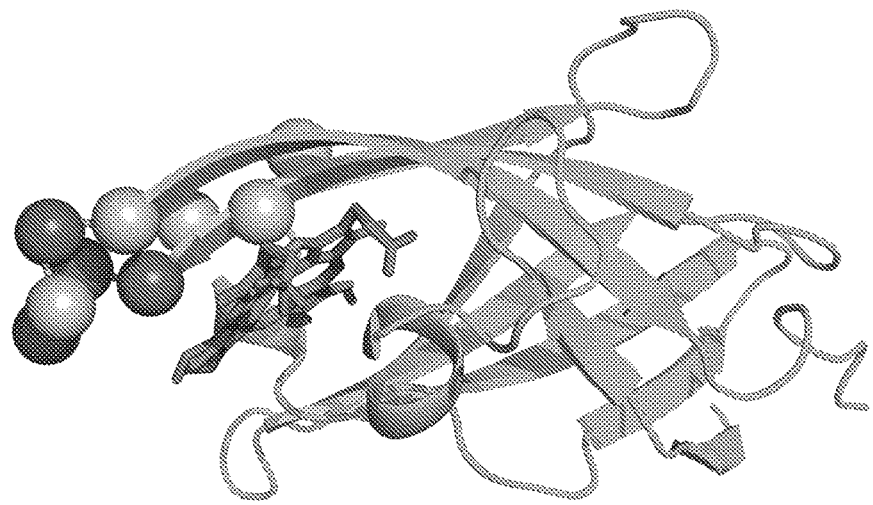
FIG. 8

HUMAN MONOCLONAL ANTIBODIES TO *STAPHYLOCOCCAL AUREUS* ISD PROTEINS AND USES THEREOF

PRIORITY CLAIM

This application is a national phase application under 35 U.S.C. § 371 of International Application No. PCT/US2019/049843, filed Sep. 6, 2019, which claims benefit of priority to U.S. Provisional Application Ser. No. 62/732,824, filed Sep. 18, 2018, the entire contents of each of which are hereby incorporated by reference.

STATEMENT OF FEDERALLY-FUNDED RESEARCH

This invention was made with government support under grant nos. T32 AI 112541, R01 AI 069233 and R01 AI 073843 awarded by the National Institutes of Health. The government has certain rights in the invention.

BACKGROUND

I. Field

The present disclosure relates to the fields of immunology, microbiology, infectious disease and medicine. More specifically, the disclosure relates to the preparation of human monoclonal antibodies against Isd surface proteins of *Staphylococcus aureus*, and methods of use therefor.

II. Related Art

Microorganisms require acquisition of nutrient metals to fulfill basic metabolic needs. In response, vertebrates produce metal-binding proteins that sequester nutrients and prevent their accessibility to pathogens, in a process termed nutritional immunity (Hood and Skaar, 2012). In order to overcome this nutrient starvation, bacterial pathogens have evolved mechanisms to acquire necessary nutrient metals from their hosts. One such nutrient metal is iron, which plays a key role in cellular metabolism, respiration, and catalysis (Hood and Skaar, 2012; Skaar, 2010). Heme is both the most abundant and preferred source of iron for *Staphylococcus aureus* within the human host (Skaar et al., 2004). In order to obtain iron, staphylococcal toxins lyse host red blood cells to release hemoglobin, from which the bacterial cell then imports heme using the iron-regulated surface determinant system (Isd) system (Mazmanian et al., 2003). The Isd system is classified by the presence of a conserved NEAr iron Transporter (NEAT) domain that is important for the capture of heme and hemoglobin (Grigg et al., 2007; 2010). The surface receptor protein of the Isd system, IsdB, binds free hemoglobin, and another receptor, IsdH, binds haptoglobin hemoglobin (Skaar and Schneewind, 2004). Once bound, the Isd proteins remove the heme cofactor and transport free heme to the third surface exposed protein, IsdA, before heme is transferred to IsdC, anchored within the peptidoglycan of the cell membrane (Tones et al., 2006; Muryoi et al., 2008; Liu et al., 2008; Pilpa et al., 2006). Heme is transferred next from IsdC to IsdE, a substrate-binding lipoprotein that works in association with the membrane permease IsdF, and then into the cytoplasm of the cell for degradation (Foster et al., 2013; Choby and Skaar, 2016). These hemoproteins are necessary for the growth and virulence of *S. aureus* because of their specialized ability to capture and transport heme-iron (Torres et al., 2006; Kuklin et al., 2006; Pishchany et al., 2009).

Heme is an important cofactor for host hemoglobin, and the acquisition of iron from heme is fundamental to staphylococcal growth and pathogenesis. Therefore, targeting bacterial mechanisms for heme acquisition has been a subject of intense study in the *S. aureus* field in an effort to identify novel candidate therapeutics (Tones et al., 2006; Kuklin et al., 2006; Kim et al., 2010; Pishchany et al., 2014a; 2010). One way to target heme acquisition is through antibodies, as antibody-mediated therapy is a promising therapeutic alternative to traditional antibiotics. Therapies using monoclonal antibodies are both versatile and specific due to the inherent function of antibodies. Antibodies can enhance immune function naturally by aiding in opsonization, complement activation, and ADCC, all of which are molecular functions that aid in the clearance of microbes (Nimmerjahn, 2007fz). *S. aureus* expresses many surface antigens, such as the Isd proteins, that contribute to virulence and may be potential candidates for antibody mediated therapies such as passive immunization. Aside from direct use in therapy, anti-*S. aureus* antibodies may also be useful for informing vaccine design by elucidating new epitopes and highlighting the humoral immune response to Staphylococcal surface antibodies.

Much attention has been paid to IsdB, the hemoglobin-binding protein of the Isd system for its dominant role in heme-iron acquisition. Mutants inactivated for isdB exhibit reduced virulence in murine models and have a decreased ability to utilize hemoglobin as a sole iron source (Pishchany et al., 2014a; 2013). The NEAT domain of IsdB is responsible for its hemoglobin binding ability; therefore, it has been hypothesized that antibody-mediated blocking of this NEAT domain may effectively inhibit hemoglobin binding and iron uptake by *S. aureus* (Tones et al., 2006; Pishchany et al., 2014a). While previous studies reported isolation of murine or human monoclonal antibodies (mAbs) to IsdB that led to the production of an IsdB vaccine candidate (Merck V710, based on recognition of the CS-D7 antibody) (Brown et al., 2009; Pancari et al., 2012; Ebert et al., 2010), this vaccine ultimately proved to be ineffective in human trials (Harro et al., 2010; Moustafa et al., 2012).

In contrast, little is known about the role of antibodies to the related *S. aureus* IsdA protein in protective immunity. However, increased IsdA antibody levels have been identified in patients infected with methicillin-resistant *S. aureus* (MRSA), which correlates with similar findings in serum antibody response to IsdB (Vu et al., 2016; Diep et al., 2016; Verkaik et al., 2010a; Ghasemzadeh-Moghaddam et al., 2017). IsdA contains a NEAT domain that is responsible for heme binding, but the role of IsdA in nutrient acquisition and pathogenesis is less well-defined than that of IsdB. Furthermore, isolated human antibodies to IsdA have not been described, particularly those generated in response to invasive *S. aureus* disease.

SUMMARY

Thus, in accordance with the present disclosure, there is provided a method of detecting a *S. aureus* infection in a subject comprising (a) contacting a sample from said subject with an antibody or antibody fragment having clone-paired heavy and light chain CDR sequences from Tables 3 and 4, respectively; and (b) detecting *S. aureus* in said sample by binding of said antibody or antibody fragment to a *S. aureus* Isd antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or Western blot. The method may further comprise performing steps (a) and (b) a second time and determining a change in *S. aureus* Isd antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

In another embodiment, there is provided a method of treating a subject infected with *S. aureus* or reducing the likelihood of infection of a subject at risk of contracting *S. aureus*, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The method subject may be treated with a cocktail of antibodies or fragments thereof having specificity for more than one Isd antigen, such as where the cocktail comprises at least one antibody or fragment thereof recognizes IsdA and at least one antibody or fragment thereof recognizes IsdB, or where the cocktail comprises at least one antibody or fragment thereof recognizes IsdA and at least one antibody or fragment thereof recognizes IsdH, or where the cocktail comprises at least one antibody or fragment thereof recognizes IsdH and at least one antibody or fragment thereof recognizes IsdB. The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

Also provided is a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

Another embodiment discloses a vaccine formulation comprising one or more expression vectors encoding a first antibody or antibody fragment as described above. The expression vector(s) may be Sindbis virus or VEE vector(s). The formulation may be formulated for delivery by needle injection, jet injection, or electroporation. The formulation may further comprise one or more expression vectors encoding for a second antibody or antibody fragment, such as a distinct antibody or antibody fragment of Tables 1-4.

In an additional embodiment, there is provided a method of protecting the health of a placenta and/or fetus of a pregnant a subject infected with or at risk of infection with S. aureus comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may further comprise a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control or may reduce viral load and/or pathology of the fetus as compared to an untreated control.

In a further embodiment, there is provided a method of determining the antigenic integrity, correct conformation and/or correct sequence of a S. aureus Isd antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen or be a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the Isd antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. Competition-binding of IsdA- or IsdB-specific antibodies. Biolayer interferometry was used to perform competition-binding studies on the Isd-specific antibody panel. Either IsdA (left panel) or IsdB (right panel) was biotinylated and loaded onto streptavidin tips before testing binding to a first and then second antibody. Data above indicate the percent binding of the second antibody to the biosensor tip in the presence of bound first antibody. Black boxes indicate the first antibody blocked binding of the second antibody by more than 70%. Grey boxes indicate the first antibody partially blocked binding of the second antibody, with 31-75% residual binding of the second remaining. White boxes indicate the first antibody did not block binding of the second antibody to the biosensor tip. Assigned competition-binding groups are outlined in color. Certain cross-competing antibodies did not bind well to both IsdA and IsdB using biolayer interferometry, suggesting that they may be members of an additional competition-binding group that could not be tested in this way.

FIGS. 2A-B. Isd-specific antibodies reduce bacterial burden in a systemic murine model of infection. (FIG. 2A) Seven-week old female BALB/c mice were inoculated retro-orbitally with an O.D. of 0.4 suspension (~10$^7$ CFU) S. aureus strain Newman. After ninety-six hours, the heart, livers, and kidneys of the infected mice were harvested in cold PBS. CFU counts were determined by serial dilution plating on TSA. P values were determined by a Kruskal-Wallis non-parametric test and the Dunn Procedure for multiple comparisons. (FIG. 2B) Weight loss over the course of 96 hours was calculated as a percentage of the starting weight. P values were determined by ANOVA.

FIGS. 4A-C. Binding sites and conservation of STAU-239 and STAU-245 on IsdA-N1. Hydrogen-deuterium exchange mass spectrometry (HD-XMS) was used to map the binding sites of STAU-239 and STAU-245 onto IsdA. (FIG. 4A) The sequence of IsdA-N1 is shown (SEQ ID NO: 211) and amino acids with the strongest decrease in deuterium uptake in the presence of STAU-239 (blue) or STAU-245 (orange) and IsdA are colored. (FIG. 4B) The structure of the crystalized NEAT domain of IsdA (PDB ID: 2ITF) is shown binding heme (red) with the predicted binding sites of STAU-239 (blue) and STAU-245 (orange). (FIG. 4C) Amino acid changes in the S. aureus strain Newman IsdA protein were determined from 42,522 S. aureus genomes. Frequency distribution of all amino acid changes across the 350 residues of IsdA in 42,522 strains is shown (top). Amino acid changes observed specifically in the STAU-239 binding site (amino acid positions 159 and 167) are highlighted (bottom).

FIGS. 5A-B. STAU-239+STAU-245 Fc mutants do not reduce bacterial burden in systemic murine model of infection. (FIG. 5A) Seven-week old female BALB/c mice were inoculated retro-orbitally with an O.D.$_{600}$ of 0.4 suspension of S. aureus strain Newman. Mice were given one of two mixes: [STAU-239+245 IgG] or [STAU-239+245 LALA (L234A, L235A) variant] by the IP route two hours before infection. After ninety-six hours, the heart, livers, and kidneys of the infected mice were harvested in cold PBS. CFU counts were determined by serial dilution plating on TSA. P values were determined by a Kruskal-Wallis non-parametric test and the Dunn Procedure for multiple comparisons. (FIG. 5B) Weight loss over the 96-hour infection was calculated as a percentage of the starting weight. P values were determined by ANOVA.

FIGS. 7A-C. HDX-MS of IsdA-STAU-239 and IsdA-STAU-245 (FIG. 7A) Heat map showing the difference in relative Deuterium-uptake of IsdA in complex with STAU-239 fab (top) and STAU-245 (bottom) compared to unbound IsdA. The sequence of IsdA is shown (SEQ ID NO: 212) and overlapping peptides are shown below. Shielded amino acids (blue) indicate potential binding-sites and are boxed.

(FIG. 7B) The structure of the crystalized NEAT domain of IsdA (PDB ID: 2ITF) with the binding site for STAU-239 and heme (red) shown. Coloring represents the difference in Deuterium-uptake in complex to solitary IsdA from HDX (30 s time point). Scale ranges from −20 (blue) to +20 (red), black represents not observed regions. (FIG. 7C) The structure of the crystalized NEAT domain of IsdA (PDB ID: 2ITF) with the binding site for STAU-245 and heme (red) shown.

FIG. 8. Genetic conservation within the binding site of STAU-239. The frequency of mutations within the STAU-239 binding site is mapped onto the crystalized NEAT domain of IsdA (PDB ID: 2ITF). Spheres represent individual amino acid residues and the color denotes conservation of that residue. Pale blue spheres are residues that are conserved throughout all *S. aureus* genomes while blue spheres show differences in less than 10 genomes, and violet spheres represent differences in more than 10 genomes.

DESCRIPTION OF ILLUSTRATIVE EMBODIMENTS

Figure 3:
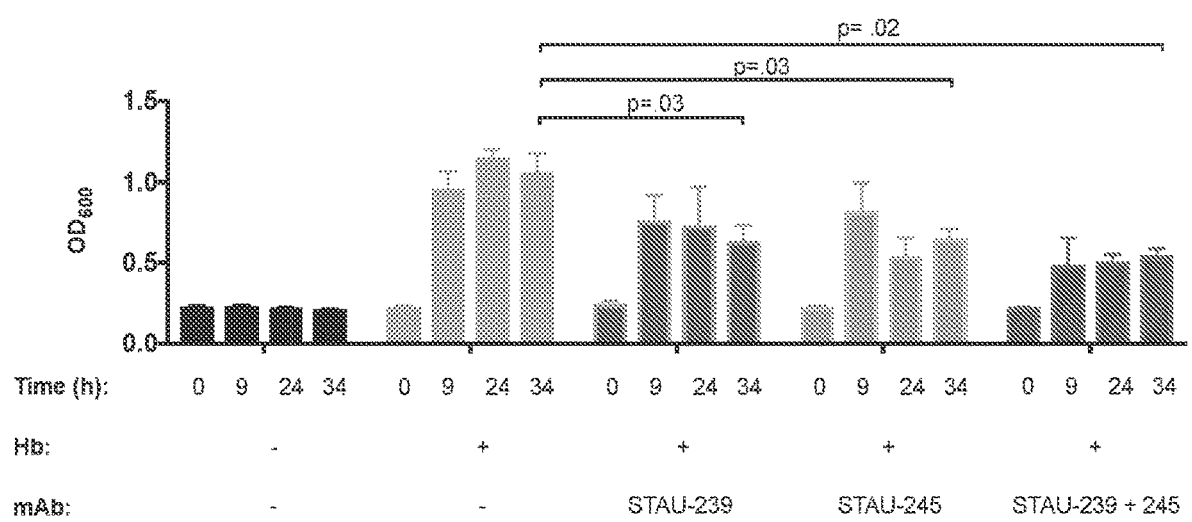
FIG. 3. Partial inhibition of S. aureus hemoglobin-dependent growth. S. aureus strain Newman was cultured overnight in RPMI with 1 µM EDDHA and normalized to an O.D.$_{600}$ of 1 before being subcultured and grown in broth for 32 hours. Untreated indicates there was no addition of hemoglobin (Hb) or antibody. Asterisks indicate statistically significant differences as determined by an unpaired t-test where the Hb treated group was set as the comparator.

As discussed above, the human pathogen *Staphylococcus aureus* causes a wide range of infections, including skin abscesses, osteomyelitis, and sepsis. There is currently no licensed vaccine to prevent *S. aureus* infection, and its treatment has become increasingly difficult due to antibiotic resistance. One potential way to inhibit *S. aureus* pathogenesis is to prevent iron acquisition. The iron-regulated surface determinant (Isd) system has evolved in *S. aureus* to acquire hemoglobin from the human host as a source of heme-iron. In this study, the inventors identified cross-reactive human monoclonal antibodies that bind to several surface Isd proteins. Using a murine septic model of infection, they discovered antibodies that worked cooperatively to decrease bacterial burden by an Fc-mediated mechanism mediated by binding of the antibody region to FcγR receptors on effector cells. This is the first description of the isolation and characterization of IsdA-specific human monoclonal antibodies, in addition to providing novel IsdA/B and IsdA/B/H cross-reactive antibodies. The inventors also show that IsdA-specific antibodies can reduce bacterial replication in a murine model of *S. aureus* septicemia. Unexpectedly, they found that this IsdA antibody-mediated protection did not predominately act by blocking iron acquisition but also used antibody Fc-mediated effector functions for inhibition of bacterial growth in vivo. These data expand upon the current understanding of IsdA-antibodies, highlighting the value of Fc-mediated antibody functions in protective immunity to *S. aureus* infection.

These and other aspects of the disclosure are described in detail below.

I. *Staphylococcus aureus*

*Staphylococcus aureus* (*S. aureus*) is a Gram-positive, round-shaped bacterium that is a member of the Firmicutes, and it is a member of the normal flora of the body, frequently found in the nose, respiratory tract, and on the skin. It is often positive for catalase and nitrate reduction and is a facultative anaerobe that can grow without the need for oxygen. Although *S. aureus* is not always pathogenic (and can be found commonly existing as a commensal), it is a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies. The emergence of antibiotic-resistant strains of *S. aureus* such as methicillin-resistant *S. aureus* (MRSA) is a worldwide problem in clinical medicine. Despite much research and development there is no approved vaccine for *S. aureus*.

*Staphylococcus* was first identified in 1880 in Aberdeen, Scotland, by surgeon Sir Alexander Ogston in pus from a surgical abscess in a knee joint. This name was later amended to *Staphylococcus aureus*. An estimated 20% to 30% of the human population are long-term carriers of *S. aureus* which can be found as part of the normal skin flora, in the nostrils, and as a normal inhabitant of the lower reproductive tract of women. *S. aureus* can cause a range of illnesses, from minor skin infections, such as pimples, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. It is still one of the five most common causes of hospital-acquired infections and is often the cause of wound infections following surgery. Each year, around 500,000 patients in hospitals of the United States contract a staphylococcal infection, chiefly by *S. aureus*. Up to 50,000 deaths each year in the USA are linked with *S. aureus* infections.

A. Microbiology

*S. aureus* is a facultative anaerobic, gram-positive coccal (round) bacterium also known as "golden staph" and "oro staphira". *S. aureus* is non-motile and does not form spores. In medical literature, the bacterium is often referred to as *S. aureus, Staph aureus* or Staph A. *S. aureus* appears as staphylococci (grape-like clusters) when viewed through a microscope, and has large, round, golden-yellow colonies, often with hemolysis, when grown on blood agar plates. *S. aureus* reproduces asexually by binary fission. Complete separation of the daughter cells is mediated by *S. aureus* autolysin, and in its absence or targeted inhibition, the daughter cells remain attached to one another and appear as clusters.

*S. aureus* is catalase-positive (meaning it can produce the enzyme catalase). Catalase converts hydrogen peroxide ($H_2O_2$) to water and oxygen. Catalase-activity tests are sometimes used to distinguish staphylococci from enterococci and streptococci. Previously, *S. aureus* was differentiated from other staphylococci by the coagulase test. However, not all *S. aureus* strains are coagulase-positive and incorrect species identification can impact effective treatment and control measures.

Natural genetic transformation is a reproductive process involving DNA transfer from one bacterium to another through the intervening medium, and the integration of the donor sequence into the recipient genome by homologous recombination. *S. aureus* was found to be capable of natural genetic transformation, but only at low frequency under the experimental conditions employed. Further studies suggested that the development of competence for natural genetic transformation may be substantially higher under appropriate conditions, yet to be discovered.

B. Role in Health

In humans, *S. aureus* is part of the normal microbiota present in the upper respiratory tract, and on skin and in the gut mucosa. *S. aureus*, along with similar species that can colonize and act symbiotically but can cause disease if they begin to take over the tissues they have colonized or invade other tissues, have been called "pathobionts".

C. Role in Disease

While *S. aureus* usually acts as a commensal bacterium, asymptomatically colonizing about 30% of the human population, it can sometimes cause disease. In particular, *S. aureus* is one of the most common causes of bacteremia and infective endocarditis. Additionally, it can cause various skin and soft tissue infections, particularly when skin or mucosal barriers have been breached.

*S. aureus* infections can spread through contact with pus from an infected wound, skin-to-skin contact with an infected person and contact with objects used by an infected person such as towels, sheets, clothing, or athletic equipment. Joint replacements put a person at particular risk of septic arthritis, staphylococcal endocarditis (infection of the heart valves), and pneumonia.

Diabetics, injection drug users, and individuals with heart conditions, should take extra precautions to avoid coming into contact with *Staphylococcus aureus*, as they are at the highest risk. A couple preventive measures are, washing hands often with soap and making sure to bathe or shower daily.

*S. aureus* is a significant cause of chronic biofilm infections on medical implants and the repressor of toxins is part of the infection pathway.

*S. aureus* can lay dormant in the body for years undetected. Once symptoms begin to show, the host is contagious for another two weeks and the overall illness lasts a few weeks. If untreated though, the disease can be deadly. Deeply penetrating *S. aureus* infections can be severe.

Skin infections. Skin infections are the most common form of *S. aureus* infection. This can manifest in various ways, including small benign boils, folliculitis, impetigo, cellulitis, and more severe, invasive soft-tissue infections.

*S. aureus* is extremely prevalent in persons with atopic dermatitis. It is mostly found in fertile, active places, including the armpits, hair, and scalp. Large pimples that appear in those areas may exacerbate the infection if lacerated. This can lead to staphylococcal scalded skin syndrome, a severe form of which can be seen in newborns.

The presence of *S. aureus* in persons with atopic dermatitis is not an indication to treat with oral antibiotics, as evidence has not shown this to give benefit to the patient. The relationship between *S. aureus* and atopic dermatitis is unclear.

Food poisoning. *S. aureus* is also responsible for food poisoning. It is capable of generating toxins that produce food poisoning in the human body. Its incubation period lasts one to six hours, with the illness itself lasting anywhere from thirty minutes to three days. Preventative measures one can take to help prevent the spread of the disease include washing hands thoroughly with soap and water before preparing food. Stay away from any food if you are ill, and wear gloves if there are any open wounds on your hands or wrists while preparing food. If storing food for longer than 2 hours, keep the food above 140° F. or below 40° F.

Bone and joint infections. *S. aureus* is the bacterium that is commonly responsible for all major bone and joint infections. This manifests in one of three forms: osteomyelitis, septic arthritis and infection from a replacement joint surgery.

Bacteremia. *S. aureus* is a leading cause of bloodstream infections throughout much of the industrialized world. Infection is generally associated with breakages in the skin or mucosal membranes due to surgery, injury, or use of intravascular devices such as catheters, hemodialysis machines, or injected drugs. Once the bacteria have entered the bloodstream, they can infect various organs, causing infective endocarditis, septic arthritis, and osteomyelitis. This disease is particularly prevalent and severe in the very young and very old.

Without antibiotic treatment, *S. aureus* bacteremia has a case fatality rate around 80%. With antibiotic treatment, case fatality rates range from 15% to 50% depending on the age and health of the patient, as well as the antibiotic resistance of the *S. aureus* strain.

Medical implant infections. *S. aureus* is often found in biofilms formed on medical devices implanted in the body or on human tissue. It is commonly found with another pathogen, *Candida albicans*, forming multispecies biofilms. The latter is suspected to help *S. aureus* penetrate human tissue. A higher mortality is linked with multispecies biofilms.

*S. aureus* biofilm is the predominant cause of orthopedic implant-related infections but is also found on cardiac implants, vascular grafts, various catheters, and cosmetic surgical implants. After implantation, the surface of these devices becomes coated with host proteins, which provide a rich surface for bacterial attachment and biofilm formation. Once the device becomes infected, it must by completely removed since *S. aureus* biofilm cannot be destroyed by antibiotic treatments.

Current therapy for *S. aureus* biofilm-mediated infections involves surgical removal of the infected device followed by antibiotic treatment. Conventional antibiotic treatment alone is not effective in eradicating such infections. An alternative to post-surgical antibiotic treatment is using antibiotic-loaded, dissolvable calcium sulfate beads, which are implanted with the medical device. These beads can release high doses of antibiotics at the desired site to prevent the initial infection.

Novel treatments for *S. aureus* biofilm involving nano silver particles, bacteriophages, and plant-derived antibiotic agents, are being studied. These agents have shown inhibitory effects against *S. aureus* embedded in biofilms. A class of enzymes have been found to have biofilm matrix degrading ability and thus may be used as biofilm dispersal agents in combination with antibiotics.

Animal infections. *S. aureus* can survive on dogs, cats, and horses, and can cause bumblefoot in chickens. Some believe health-care workers' dogs should be considered a significant source of antibiotic-resistant *S. aureus*, especially in times of outbreak. *S. aureus* is one of the causal agents of mastitis in dairy cows. Its large polysaccharide capsule protects the organism from recognition by the cow's immune defenses.

D. Virulence factors

Enzymes. *S. aureus* produces various enzymes such as coagulase (bound and free coagulases) which clots plasma and coats the bacterial cell, probably to prevent phagocytosis. Hyaluronidase (also known as spreading factor) breaks down hyaluronic acid and helps in spreading it. *S. aureus* also produces deoxyribonuclease, which breaks down the DNA, lipase to digest lipids, staphylokinase to dissolve fibrin and aid in spread, and beta-lactamase for drug resistance.

Toxins. Depending on the strain, *S. aureus* is capable of secreting several exotoxins, which can be categorized into three groups. Many of these toxins are associated with specific diseases.

Superantigens. Antigens known as superantigens can induce toxic shock syndrome (TSS). This group includes the toxins TSST-1, and enterotoxin type B, which causes TSS associated with tampon use. Toxic shock syndrome is characterized by fever, erythematous rash, low blood pressure, shock, multiple organ failure, and skin peeling. Lack of antibody to TSST-1 plays a part in the pathogenesis of TSS. Other strains of *S. aureus* can produce an enterotoxin that is the causative agent of a type of gastroenteritis. This form of gastroenteritis is self-limiting, characterized by vomiting and diarrhea one to six hours after ingestion of the toxin, with recovery in eight to 24 hours. Symptoms include nausea, vomiting, diarrhea, and major abdominal pain.

Exfoliative toxins. Exfoliative toxins are exotoxins implicated in the disease staphylococcal scalded skin syndrome (SSSS), which occurs most commonly in infants and young children. It also may occur as epidemics in hospital nurseries. The protease activity of the exfoliative toxins causes peeling of the skin observed with SSSS.

Other toxins. Staphylococcal toxins that act on cell membranes include alpha toxin, beta toxin, delta toxin, and several bicomponent toxins. Strains of *S. aureus* can host phages, such as the prophage Φ-PVL that produces Panton-Valentine leukocidin (PVL), to increase virulence. The bicomponent toxin PVL is associated with severe necrotizing pneumonia in children. The genes encoding the components of PVL are encoded on a bacteriophage found in community-associated MRSA strains.

small RNA. There is a growing list of small RNAs involved in the control of bacterial virulence in *S. aureus*. For example, RNAIII, SprD, RsaE, SprA1, SSR42, ArtR, SprX and Teg49.

Strategies for post-transcriptional regulation by 3'untranslated region. It has been shown that many mRNAs in *S. aureus* carry three prime untranslated regions (3'UTR) longer than 100 nucleotides, which may potentially have a regulatory function.

Further investigation of icaR mRNA (mRNA coding for the repressor of the main expolysaccharidic compound of the bacteria biofilm matrix) demonstrated that the 3'UTR binding to the 5' UTR can interfere with the translation initiation complex and generate a double stranded substrate for RNase III. It was shown that the interaction is between the UCCCCUG motif in the 3'UTR and the Shine-Dalagarno region at the 5'UTR. Deletion of the motif resulted in IcaR repressor accumulation and inhibition of biofilm development. The biofilm formation is the main cause of *Staphylococcus* implant infections.

Biofilm. *S. aureus* biofilm has high resistance to antibiotic treatments and host immune response. One hypothesis for explaining this is that the biofilm matrix protects the embedded cells by acting as a barrier to prevent antibiotic penetration. However, recent findings have shown that the biofilm matrix is composed with many water channels, so this hypothesis is becoming increasingly less likely. But it is possible that biofilm matrix contains antibiotic-degrading enzymes such as β-lactamases, which can prevent antibiotic penetration. Another hypothesis is that the conditions in the biofilm matrix favor the formation of persister cells, which are highly antibiotic resistant, dormant bacterial cells. *S. aureus* biofilms also have high resistance to host immune response. Even though the exact mechanism of resistance is unknown, studies have demonstrated that *S. aureus* biofilms had increased growth under the presence of cytokines produced by the host immune response. Host antibodies are less effective for *S. aureus* biofilm due to the heterogenous antigen distribution, where an antigen may be present in some areas of the biofilm but completely absent from other areas.

E. Other Immunoevasive Strategies

Protein A. Protein A is anchored to staphylococcal peptidoglycan pentaglycine bridges (chains of five glycine residues) by the transpeptidase sortase A. Protein A, an IgG-binding protein, binds to the Fc region of an antibody. In fact, studies involving mutation of genes coding for protein A resulted in a lowered virulence of *S. aureus* as measured by survival in blood, which has led to speculation that protein A-contributed virulence requires binding of antibody Fc regions.

Protein A in various recombinant forms has been used for decades to bind and purify a wide range of antibodies by immunoaffinity chromatography. Transpeptidases, such as the sortases responsible for anchoring factors like protein A to the staphylococcal peptidoglycan, are being studied in hopes of developing new antibiotics to target MRSA infections.

Staphylococcal pigments. Some strains of *S. aureus* are capable of producing staphyloxanthin—a golden-coloured carotenoid pigment. This pigment acts as a virulence factor, primarily by being a bacterial antioxidant which helps the microbe evade the reactive oxygen species which the host immune system uses to kill pathogens.

Mutant strains of *S. aureus* modified to lack staphyloxanthin are less likely to survive incubation with an oxidizing chemical, such as hydrogen peroxide, than pigmented strains. Mutant colonies are quickly killed when exposed to human neutrophils, while many of the pigmented colonies survive. In mice, the pigmented strains cause lingering abscesses when inoculated into wounds, whereas wounds infected with the unpigmented strains quickly heal.

These tests suggest the *Staphylococcus* strains use staphyloxanthin as a defence against the normal human immune system. Drugs designed to inhibit the production of staphyloxanthin may weaken the bacterium and renew its susceptibility to antibiotics. In fact, because of similarities in the pathways for biosynthesis of staphyloxanthin and human cholesterol, a drug developed in the context of cholesterol-lowering therapy was shown to block *S. aureus* pigmentation and disease progression in a mouse infection model.

F. Classical Diagnosis

Depending upon the type of infection present, an appropriate specimen is obtained accordingly and sent to the laboratory for definitive identification by using biochemical or enzyme-based tests. A Gram stain is first performed to guide the way, which should show typical Gram-positive bacteria, cocci, in clusters. Second, the isolate is cultured on mannitol salt agar, which is a selective medium with 7-9% NaCl that allows *S. aureus* to grow, producing yellow-colored colonies as a result of mannitol fermentation and subsequent drop in the medium's pH Furthermore, for differentiation on the species level, catalase (positive for all *Staphylococcus* species), coagulase (fibrin clot formation, positive for *S. aureus*), DNAse (zone of clearance on DNase agar), lipase (a yellow color and rancid odor smell), and phosphatase (a pink color) tests are all done. For staphylococcal food poisoning, phage typing can be performed to determine whether the staphylococci recovered from the food were the source of infection.

Rapid diagnosis and typing. Recent activities and food that a patient has recently eaten will be inquired about by a physician, and a physical examination is conducted to review any symptoms. With more severe symptoms, blood tests and stool culture may be in order. Diagnostic microbiology laboratories and reference laboratories are key for identifying outbreaks and new strains of *S. aureus*. Recent genetic advances have enabled reliable and rapid techniques for the identification and characterization of clinical isolates of *S. aureus* in real time. These tools support infection control strategies to limit bacterial spread and ensure the appropriate use of antibiotics. Quantitative PCR is increasingly being used to identify outbreaks of infection.

When observing the evolvement of *S. aureus* and its ability to adapt to each modified antibiotic, two basic methods known as "band-based" or "sequence-based" are employed. Keeping these two methods in mind, other methods such as multilocus sequence typing (MLST), pulsed-field gel electrophoresis (PFGE), bacteriophage typing, spa locus typing, and SCCmec typing are often conducted more than others. With these methods, it can be determined where strains of MRSA originated and also where they are currently.

With MLST, this technique of typing uses fragments of several housekeeping genes known as aroE, glpF, gmk, pta, tip, and yqiL. These sequences are then assigned a number which give to a string of several numbers that serve as the allelic profile. Although this is a common method, a limitation about this method is the maintenance of the microarray which detects newly allelic profiles, making it a costly and time-consuming experiment.

With PFGE, a method which is still very much used dating back to its first success in 1980s, remains capable of helping differentiate MRSA isolates. To accomplish this, the technique uses multiple gel electrophoresis, along with a voltage gradient to display clear resolutions of molecules. The *S. aureus* fragments then transition down the gel, producing specific band patterns that are later compared with other isolates in hopes of identifying related strains. Limitations of the method include practical difficulties with uniform band patterns and PFGE sensitivity as a whole.

Spa locus typing is also considered a popular technique that uses a single locus zone in a polymorphic region of *S. aureus* to distinguish any form of mutations. Although this technique is often inexpensive and less time-consuming, the chance of losing discriminatory power makes it hard to differentiate between MLST CCs exemplifies a crucial limitation.

Treatment. The treatment of choice for *S. aureus* infection is penicillin. An antibiotic derived from some *Penicillium* fungal species, penicillin inhibits the formation of peptidoglycan cross-linkages that provide the rigidity and strength in a bacterial cell wall. The four-membered β-lactam ring of penicillin is bound to enzyme DD-transpeptidase, an enzyme that when functional, cross-links chains of peptidoglycan that form bacterial cell walls. The binding of β-lactam to DD-transpeptidase inhibits the enzyme's functionality and it can no longer catalyze the formation of the cross-links. As a result, cell wall formation and degradation are imbalanced, thus resulting in cell death. In most countries, however, penicillin resistance is extremely common, and first-line therapy is most commonly a penicillinase-resistant β-lactam antibiotic (for example, oxacillin or flucloxacillin, both of which have the same mechanism of action as penicillin). Combination therapy with gentamicin may be used to treat serious infections, such as endocarditis, but its use is controversial because of the high risk of damage to the kidneys. The duration of treatment depends on the site of infection and on severity. Adjunctive rifampicin has been historically used in the management of *S aureus* bacteraemia, but randomised controlled trial evidence has shown this to be of no overall benefit over standard antibiotic therapy.

Antibiotic resistance in *S. aureus* was uncommon when penicillin was first introduced in 1943. Indeed, the original Petri dish on which Alexander Fleming of Imperial College London observed the antibacterial activity of the *Penicillium* fungus was growing a culture of *S. aureus*. By 1950, 40% of hospital *S. aureus* isolates were penicillin-resistant; by 1960, this had risen to 80%.

MRSA is one of a number of greatly feared strains of *S. aureus* which have become resistant to most β-lactam antibiotics. For this reason, vancomycin, a glycopeptide antibiotic, is commonly used to combat MRSA. Vancomycin inhibits the synthesis of peptidoglycan, but unlike β-lactam antibiotics, glycopeptide antibiotics target and bind to amino acids in the cell wall, preventing peptidoglycan cross-linkages from forming. MRSA strains are most often found associated with institutions such as hospitals but are becoming increasingly prevalent in community-acquired infections.

Minor skin infections can be treated with triple antibiotic ointment.

G. Antibiotic Resistance

Bacterial cells of *S. aureus*, which is one of the causal agents of mastitis in dairy cows: Its large capsule protects the organism from attack by the cow's immunological defenses.

Staphylococcal resistance to penicillin is mediated by penicillinase (a form of (3-lactamase) production: an enzyme that cleaves the β-lactam ring of the penicillin molecule, rendering the antibiotic ineffective. Penicillinase-resistant β-lactam antibiotics, such as methicillin, nafcillin, oxacillin, cloxacillin, dicloxacillin, and flucloxacillin, are able to resist degradation by staphylococcal penicillinase.

Resistance to methicillin is mediated via the mec operon, part of the staphylococcal cassette chromosome mec (SCCmec). Resistance is conferred by the mecA gene, which codes for an altered penicillin-binding protein (PBP2a or PBP2') that has a lower affinity for binding β-lactams (penicillins, cephalosporins, and carbapenems). This allows for resistance to all β-lactam antibiotics and obviates their clinical use during MRSA infections. As such, the glycopeptide vancomycin is often deployed against MRSA.

Aminoglycoside antibiotics, such as kanamycin, gentamicin, streptomycin, etc., were once effective against staphylococcal infections until strains evolved mechanisms to inhibit the aminoglycosides' action, which occurs via protonated amine and/or hydroxyl interactions with the ribosomal RNA of the bacterial 30S ribosomal subunit. Three main mechanisms of aminoglycoside resistance mechanisms are currently and widely accepted: aminoglycoside modifying enzymes, ribosomal mutations, and active efflux of the drug out of the bacteria.

Aminoglycoside-modifying enzymes inactivate the aminoglycoside by covalently attaching either a phosphate, nucleotide, or acetyl moiety to either the amine or the alcohol key functional group (or both groups) of the antibiotic. This changes the charge or sterically hinders the antibiotic, decreasing its ribosomal binding affinity. In *S. aureus*, the best-characterized aminoglycoside-modifying enzyme is aminoglycoside adenylyltransferase 4' IA (ANT (4)IA). This enzyme has been solved by X-ray crystallography. The enzyme is able to attach an adenyl moiety to the 4' hydroxyl group of many aminoglycosides, including kamamycin and gentamicin.

Glycopeptide resistance is mediated by acquisition of the vanA gene, which originates from the enterococci and codes for an enzyme that produces an alternative peptidoglycan to which vancomycin will not bind.

Today, *S. aureus* has become resistant to many commonly used antibiotics. In the UK, only 2% of all *S. aureus* isolates are sensitive to penicillin, with a similar picture in the rest of the world. The β-lactamase-resistant penicillins (methicillin, oxacillin, cloxacillin, and flucloxacillin) were developed to treat penicillin-resistant *S. aureus* and are still used as first-line treatment. Methicillin was the first antibiotic in this class to be used (it was introduced in 1959), but, only two years later, the first case of MRSA was reported in England.

Despite this, MRSA generally remained an uncommon finding, even in hospital settings, until the 1990s, when the MRSA prevalence in hospitals exploded, and it is now endemic.

MRSA infections in both the hospital and community setting are commonly treated with non-β-lactam antibiotics, such as clindamycin (a lincosamine) and co-trimoxazole (also commonly known as trimethoprim/sulfamethoxazole). Resistance to these antibiotics has also led to the use of new, broad-spectrum anti-Gram-positive antibiotics, such as linezolid, because of its availability as an oral drug. First-line treatment for serious invasive infections due to MRSA is currently glycopeptide antibiotics (vancomycin and teicoplanin). A number of problems with these antibiotics occur, such as the need for intravenous administration (no oral preparation is available), toxicity, and the need to monitor drug levels regularly by blood tests. Also, glycopeptide antibiotics do not penetrate very well into infected tissues (this is a particular concern with infections of the brain and meninges and in endocarditis). Glycopeptides must not be used to treat methicillin-sensitive *S. aureus* (MSSA), as outcomes are inferior.

Because of the high level of resistance to penicillins and because of the potential for MRSA to develop resistance to vancomycin, the U.S. Centers for Disease Control and Prevention has published guidelines for the appropriate use of vancomycin. In situations where the incidence of MRSA infections is known to be high, the attending physician may choose to use a glycopeptide antibiotic until the identity of the infecting organism is known. After the infection is confirmed to be due to a methicillin-susceptible strain of *S. aureus*, treatment can be changed to flucloxacillin or even penicillin], as appropriate.

Vancomycin-resistant *S. aureus* (VRSA) is a strain of *S. aureus* that has become resistant to the glycopeptides. The first case of vancomycin-intermediate *S. aureus* (VISA) was reported in Japan in 1996; but the first case of *S. aureus* truly resistant to glycopeptide antibiotics was only reported in 2002. Three cases of VRSA infection had been reported in the United States as of 2005.

H. Infection Control

Spread of *S. aureus* (including MRSA) generally is through human-to-human contact, although recently some veterinarians have discovered the infection can be spread through pets, with environmental contamination thought to play a relatively unimportant part. Emphasis on basic handwashing techniques are, therefore, effective in preventing its transmission. The use of disposable aprons and gloves by staff reduces skin-to-skin contact, so further reduces the risk of transmission.

Recently, myriad cases of *S. aureus* have been reported in hospitals across America. Transmission of the pathogen is facilitated in medical settings where healthcare worker hygiene is insufficient. *S. aureus* is an incredibly hardy bacterium, as was shown in a study where it survived on polyester for just under three months; polyester is the main material used in hospital privacy curtains.

The bacteria are transported on the hands of healthcare workers, who may pick them up from a seemingly healthy patient carrying a benign or commensal strain of *S. aureus*, and then pass it on to the next patient being treated. Introduction of the bacteria into the bloodstream can lead to various complications, including endocarditis, meningitis, and, if it is widespread, sepsis.

Ethanol has proven to be an effective topical sanitizer against MRSA. Quaternary ammonium can be used in conjunction with ethanol to increase the duration of the sanitizing action. The prevention of nosocomial infections involves routine and terminal cleaning. Nonflammable alcohol vapor in $CO_2$ NAV-$CO_2$ systems have an advantage, as they do not attack metals or plastics used in medical environments, and do not contribute to antibacterial resistance.

An important and previously unrecognized means of community-associated MRSA colonization and transmission is during sexual contact.

*S. aureus* is killed in one minute at 78° C. and in ten minutes at 64° C.

Certain strains of *S. aureus* have been described as being resistant to chlorine disinfection.

II. Monoclonal Antibodies and Production Thereof

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that monoclonal antibodies binding to *S. aureus* will have several applications. These include the production of diagnostic kits for use in detecting and diagnosing *S. aureus* infection, as well as for treating the same.

In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce *S. aureus*-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A. When the antibody neutralizes S. aureus, antibody escape mutant variant organisms can be isolated by propagating S. aureus in vitro or in animal models in the presence of high concentrations of the antibody. Sequence analysis of the S. aureus gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-S. aureus antibody, the above-described binding methodology is performed in two orientations: In a first orientation, the reference antibody is allowed to bind to the S. aureus antigen under saturating conditions followed by assessment of binding of the test antibody to the S. aureus molecule. In a second orientation, the test antibody is allowed to bind to the S. aureus antigen molecule under saturating conditions followed by assessment of binding of the reference antibody to the S. aureus molecule. If, in both orientations, only the first (saturating) antibody is capable of binding to the S. aureus, then it is concluded that the test antibody and the reference antibody compete for binding to the S. aureus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (0 the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al. (1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1m$\Psi$) outperforms several other nucleoside modifications and their combinations in terms of translation capacity. In addition to turning off the immune/eIF2α phosphorylation-dependent inhibition of translation, incorporated N1m$\Psi$ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401 403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAbs, but were completely devoid of enhancing activity. LALA mutations of this nature are therefore contemplated in the context of the presently disclosed antibodies.

Altered Glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells, but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1\times10^{-8}$ M or less and from Fc gamma RIII with a Kd of $1\times10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications. such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:
1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an antipathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab').sub.2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from E. coli, which can be chemically coupled to form bispecific antibodies. Shalaby et al., J. Exp. Med., 175: 217-225 (1992) describe the production of a humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., Nat. Biotechnol. 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264; Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., Science, 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
(a) a first Fab molecule which specifically binds to a first antigen
(b) a second Fab molecule which specifically binds to a second antigen, and wherein the variable domains VL and VH of the Fab light chain and the Fab heavy chain are replaced by each other,
wherein the first antigen is an activating T cell antigen and the second antigen is a target cell antigen, or the first antigen is a target cell antigen and the second antigen is an activating T cell antigen; and
wherein
i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. Active/Passive Immunization and Treatment/Prevention of *S. aureus* Infection A. Formulation and Administration The present disclosure provides pharmaceutical compositions comprising anti-*S. aureus* antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of *S. aureus* infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. Antibody Conjugates

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugate contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850, 752, 3,939,350, 3,996,345, 4,277,437, 4,275,149 and 4,366, 241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxy benzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. Immunodetection Methods

In still further embodiments, the present disclosure concerns immunodetection methods for binding, purifying, removing, quantifying and otherwise generally detecting S. aureus and its associated antigens. While such methods can be applied in a traditional sense, another use will be in quality control and monitoring of vaccine and other S. aureus stocks, where antibodies according to the present disclosure can be used to assess the amount or integrity (i.e., long term stability) of antigens in S. aureus. Alternatively, the methods may be used to screen various antibodies for appropriate/desired reactivity profiles.

Other immunodetection methods include specific assays for determining the presence of S. aureus in a subject. A wide variety of assay formats are contemplated, but specifically those that would be used to detect S. aureus in a fluid obtained from a subject, such as saliva, blood, plasma, sputum, semen or urine. The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of S. aureus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing S. aureus, and contacting the sample with a first antibody in accordance with the present disclosure, as the case may be, under conditions effective to allow the formation of immunocomplexes.

These methods include methods for purifying S. aureus or related antigens from a sample. The antibody will preferably be linked to a solid support, such as in the form of a column matrix, and the sample suspected of containing the S. aureus or antigenic component will be applied to the immobilized antibody. The unwanted components will be washed from the column, leaving the S. aureus antigen immunocomplexed to the immobilized antibody, which is then collected by removing the organism or antigen from the column.

The immunobinding methods also include methods for detecting and quantifying the amount of S. aureus or related components in a sample and the detection and quantification of any immune complexes formed during the binding process. Here, one would obtain a sample suspected of containing S. aureus or its antigens and contact the sample with an antibody that binds S. aureus or components thereof, followed by detecting and quantifying the amount of immune complexes formed under the specific conditions. In terms of antigen detection, the biological sample analyzed may be any sample that is suspected of containing S. aureus or S. aureus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to S. aureus or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/ antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the *S. aureus* or *S. aureus* antigen is added to the wells. After binding and washing to remove non-specifically bound immune complexes, the bound antigen may be detected. Detection may be achieved by the addition of another anti-*S. aureus* antibody that is linked to a detectable label. This type of ELISA is a simple "sandwich ELISA." Detection may also be achieved by the addition of a second anti-*S. aureus* antibody, followed by the addition of a third antibody that has binding affinity for the second antibody, with the third antibody being linked to a detectable label.

In another exemplary ELISA, the samples suspected of containing the *S. aureus* or *S. aureus* antigen are immobilized onto the well surface and then contacted with the anti-*S. aureus* antibodies of the disclosure. After binding and washing to remove non-specifically bound immune complexes, the bound anti-*S. aureus* antibodies are detected. Where the initial anti-*S. aureus* antibodies are linked to a detectable label, the immune complexes may be detected directly. Again, the immune complexes may be detected using a second antibody that has binding affinity for the first anti-*S. aureus* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of *S. aureus* antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled *S. aureus* monoclonal antibodies to determine the amount of *S. aureus* antibodies in a sample. The basic format would include contacting a known amount of *S. aureus* monoclonal antibody (linked to a detectable label) with *S. aureus* antigen or cell. The *S. aureus* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in $-70°$ C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect *S. aureus* or *S. aureus* Isd antigens, the antibodies may be included in the kit. The immunodetection kits will thus comprise, in suitable container means, a first antibody that binds to *S. aureus* or *S. aureus* Isd antigen, and optionally an immunodetection reagent.

In certain embodiments, the anti-*S. aureus* antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the *S. aureus* or *S. aureus* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity, and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns, but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective *S. aureus* antibodies. Antibodies, antibody fragment, or variants and derivatives thereof, as described in the present disclosure may also be used in a kit for monitoring vaccine manufacture with the desired immunogenicity.

VI. Examples

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Human subjects. Blood was collected from pediatric subjects at Vanderbilt University Medical Center with prior documented blood culture-confirmed history of invasive MRSA or MS SA infection. Heparizined peripheral blood was collected after informed parent consent and subject assent. The studies were approved by the Institutional Review Board of Vanderbilt University Medical Center.

Generation of human monoclonal antibodies. Peripheral blood mononuclear cells (PBMCs) were isolated by Ficoll density centrifugation from de-identified blood samples. Human hybridomas were generated by transforming PBMCs with media containing Epstein-Barr virus, agonist CpG (phosphorothioate-modified oligodeoxynucleotide OEZOEZZZZZOEEZOEZZZT (SEQ ID NO: 213), Life Technologies), Chk2 inhibitor (Chk2i) (Sigma), and cyclosporine A (Sigma). Cells were plated in 384 cell culture plates and grown for seven days before expanding to 96 well plates with irradiated heterologous human PBMCs (obtained from sterile discarded de-identified leukofiltration filters, Red Cross, Nashville, TN). After an additional four to five days, cells were screened via enzyme-linked immunosorbent assay (ELISA) using S. aureus surface antigens to identify cell culture wells that contained B-cells secreting antigen specific antibodies. Cell culture wells that contained reactant wells were fused with HMMA2.5 myeloma cells via electrofusion. After fusion, hybridoma cell lines were sorted using single-cell fluorescence-activated cell sorting to achieve monoclonal hybridoma lines. Cell lines were screened and expanded before purifying filtered hybridoma supernatants using HiTrap Protein G columns.

Purified IgG proteins. For expression of antibodies from hybridoma clones, cells were cultured in serum-free medium, Hybridoma SFM (Life Technologies), for about 21 days. Antibodies were harvested from the supernatants by affinity chromatography on HiTrap Protein G columns (Life Technologies) according to the manufacturer's instructions. Antibodies eluted from affinity columns were concentrated using Amicon centrifugal filters (Millipore).

Bacterial strains. The S. aureus strain Newman was used throughout this paper. Newman was grown at 37° C. for 12-18 hours on TSA and in TSB. Isogenic knockouts were made in a Newman background and include isdB, isdA, and isdH. Development of these mutants has been described previously (Mamanian et al., 2003; 2002)

Antigen generation. Soluble forms of the antigens of interest were cloned into the pET15b plasmid vector and expressed recombinantly using the BL21 (DE3) E. coli expression system. Cultures were grown for 36 hours in Luria-Bertani (LB) broth and induced after 6 hours at 30° C. with 1 mM Isopropyl β-D-1-thiogalactopyranoside (IPTG). Cells were harvested by centrifugation and resuspended in 50 mM $Na_2HPO_4$+500 mM NaCl before disruption by sonication. The soluble fraction was purified using a HiTrap TALON column. Purified antigen was used at a concentration of 2 μg/mL when screening PBMCs and supernatants for reactivity. Antigens that were purified by this method included IsdA, IsdB, and IsdH. Each of the purified Isd proteins exhibited the capacity to interact with heme, as shown by binding in ELISA to plates coated with heme and to heme coated sensor tips in a biolayer interferometry binding assay.

Hemoglobin growth curves. S. aureus strain Newman was grown overnight in RPMI medium+1 μM EDDHA. The $O.D_{600}$ was normalized to approximately 1 and subcultured into fresh tubes of RPMI+EDDHA with 20 nM of human hemoglobin and 2 μg/mL antibody. Tubes were grown for 36 hours at 37° C. $OD_{600}$ was recorded at 12, 24, and 36 hours using path length correction in the Gen5 microtiter plate software (Bio-Tek). Human hemoglobin was purified from hemolysate by HPLC, as previously described (Pishchany et al., 2013).

Measurement of mAb binding to recombinant S. aureus proteins and half-maximal binding analysis ($EC_{50}$). MAb binding to each of the recombinant S. aureus proteins was measured by ELISA. Briefly, recombinant IsdA, IsdB or IsdH was diluted to 2 μg/mL in PBS and adsorbed on 384-well Thermo Fischer Scientific microtiter plates overnight at 4° C. Plates were blocked for 1 hour in PBS-T (0.05% Tween 20)+2% milk. Plates were washed three times with PBS-T and incubated with primary hybridoma supernatants for at least 1 hour at room temperature. When testing $EC_{50}$ binding, purified antibodies were diluted 3-fold in PBS-T at a starting concentration of 20 μg/ml before binding to the microtiter plates. Plates were washed 3 times with PBS-T and 25 μL of secondary antibody at a 1:4,000 dilution (goat anti-human IgG alkaline phosphatase conjugate; Meridian Life Science) was added to each well. After 1 hour of incubation, plates were washed 4 times and 25 μL of phosphatase substrate solution (1 mg/mL phosphatase substrate in 1 M Tris aminomethane; Sigma) was added to each well. The plates were incubated at room temperature in the dark before reading at an optical density of 405 nm using a Biotek plate reader. To calculate $EC_{50}$ values, anon-linear regression analysis was applied to the curves using Prism v 7.0 (GraphPad Software, Inc.).

Biolayer interferometry competition-binding assay. Competition-binding studies using biolayer interferometry and biotinylated IsdA, IsdB, or IsdH (5 μg/mL) were performed on an Octet RED biosensor (Pall FortéBio Menlo Park, CA). The antigen was immobilized onto streptavidin-coated biosensor tips. After a brief washing step, biosensor tips were immersed into the wells containing a first antibody at a concentration of 100 μg/mL and then into the wells containing a second mAb, also at a concentration of 100 μg/mL. Competition groups were determined by calculating the percent binding of the second mAb in the presence of the first mAb, compared to the maximal signal of the second mAb alone (the value of uncompleted binding was normalized to 100%). Antibodies were defined as competing if the first antibody reduced the binding of the second antibody to <30% of the uncompeted level of binding; the figure shows values for the % binding during competition. Antibodies were defined as partial competitors if they reduced binding of the second antibody to a level of 31-74% of uncompeted binding. Finally, antibodies that did not reduce binding of the second antibody below 75% of uncompleted binding were characterized as non-competing.

Mouse experiments. A mouse septic model of S. aureus infection was used, as previously described (Pishchany et al., 2010). Wild-type S aureus strain Newman was streaked from frozen stocks onto TSA plates two days before infection. Overnight cultures then were grown in TSB broth. On the day of infection, overnight cultures were subcultured 1:100 and grown for two hours to mid-exponential phase. During this time, mice were weighed and injected with 10 mg/kg antibody via the intraperitoneal route. *S. aureus* cells were harvested by centrifugation and washed with cold PBS to a final concentration of $10^7$ CFU/100 μL injection. 6-8 week female BALB/cJ (n=20 for all experimental groups except MRSA 239 where n=15) were anesthetized prior to retro-orbital injection with *S. aureus*. The infection continued for 96 hours before the mice were euthanized using $CO_2$ inhalation. The heart, liver, and kidneys were homogenized in PBS and serially diluted before plating on TSA for colony enumeration. Mouse experiments were approved and performed according to the guidelines of the Vanderbilt University School of Medicine Institutional Animal Care and Use Committee (IACUC).

Statistical analysis. All data were analysed in Prism v 7.0 (GraphPad Software Inc.) and expressed as mean values and their standard error of the mean (SEM). P-values for animal experiments were calculated using a Mann-Whitney test as indicated and hemoglobin-dependent growth p-values were calculated using an unpaired t-test. P-values for peptide binding were determined by a Kruskal-Wallis one-way analysis of variance. *=P≤0.05. =P≤0.01. *P≤0.001.

Example 2—Results

Isolation of Isd-reactive human mAbs. To define the human B cell response to staphylococcal surface Isd proteins, the inventors isolated a panel of human mAbs reactive with IsdA, IsdB, or IsdH recombinant proteins. Antibodies were isolated from the circulating memory B cells of human subjects with varying severity of *S. aureus* invasive disease (Table 51). Peripheral blood was drawn from these individuals 4-6 weeks following infection. PBMCs were isolated from the donor blood samples and immortalized by EBV before fusing with myeloma cells and single-cell flow cytometric sorting to isolate mAb-secreting hybridomas.

Antibodies were classified based on their pattern of binding to three Isd proteins: IsdA, IsdB, or IsdH. The inventors observed all possible cross-reactive binding patterns for clonal IgGs (Table A). Antibodies specific to individual Isd proteins were identified, however the majority of the mAbs bound to more than one Isd protein in ELISA. Three antibodies (STAU-307, -399, and -37) bound to all three Isd proteins. An ELISA was used to determine the immunoglobulin subclass of each mAb, with the majority of the panel being IgG1 (Table A). The $EC_{50}$ values are the half-maximal binding concentrations of the antibodies to their antigen. Each antibody was tested for binding to IsdA, IsdB, or IsdH and any antibody that did not bind at the starting concentration of 20 μg/mL was classified as a non-binder for that antigen. The cross-reactive nature of the identified IgGs was consistent with the conservation of heme- and hemoglobin-binding functions in these three *S. aureus* proteins.

Figure 1:
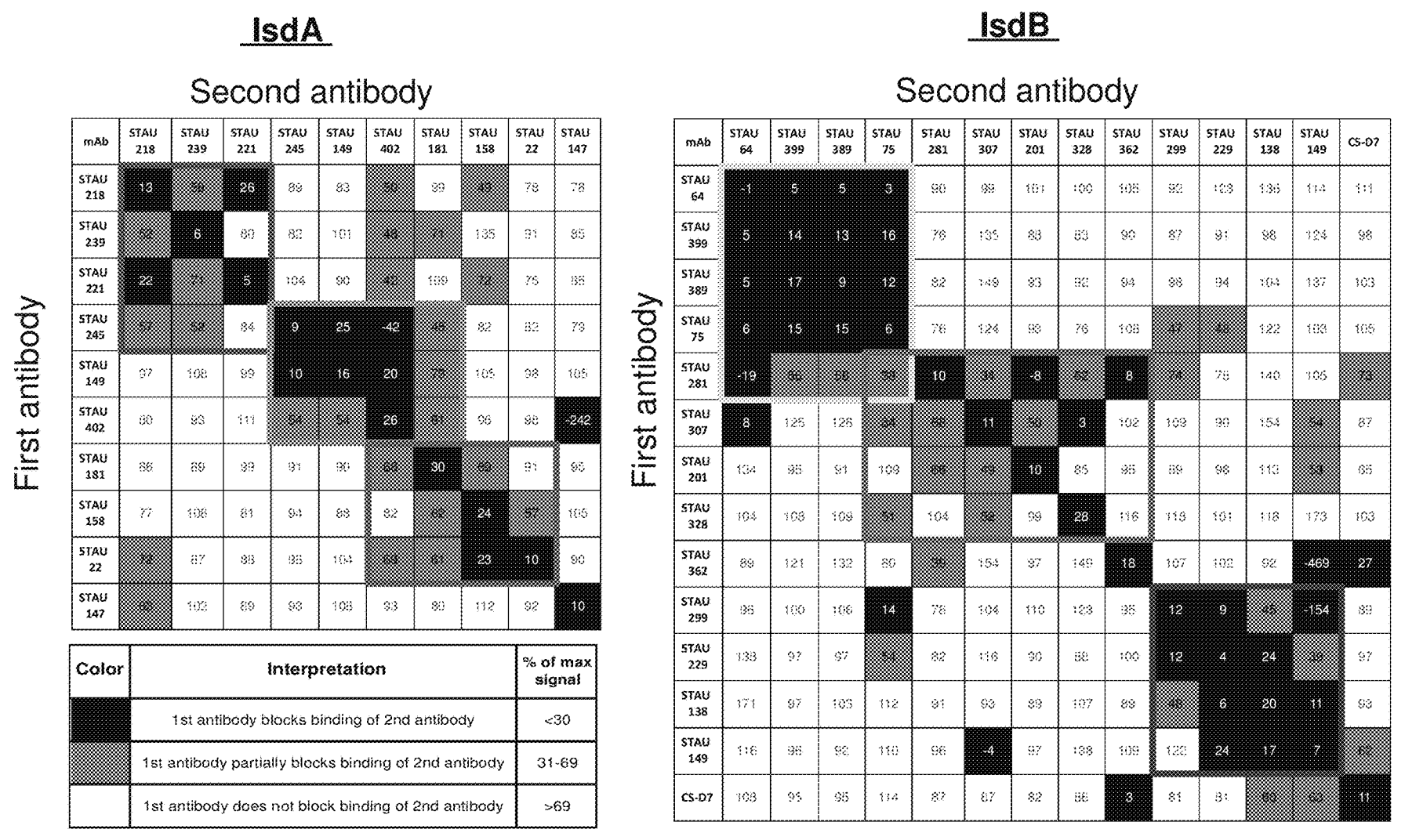

Competition-binding studies. The inventors performed competition-binding studies using biolayer interferometry (BLI) to identify the major antigenic sites targeted by each mAb. Biotinylated recombinant IsdA or IsdB suspensions were used to coat streptavidin biosensor tips before association with a first and then a second mAb (FIG. 1). Although all isolated antibodies were tested by BLI, not all antibodies bound to the biosensors with a high enough affinity to allow competition analysis. A recombinant form of the previously identified mAb CS-D7 (Pancari et al., 2012; Ebert et al., 2010) was included in the IsdB competition-binding study for comparative purposes. Three competition-binding groups were identified for both IsdA and IsdB. Multiple cross-reactive antibodies bound to both IsdA and IsdB by ELISA, but in some cases these mAbs did not bind to both Isd antigens in the BLI assay. Two antibodies, STAU-239 and STAU-245, were members of a single competition-binding group to IsdA (blue), suggesting that they bound to a common major antigenic site that may be important for Isd function.

Figure 6:
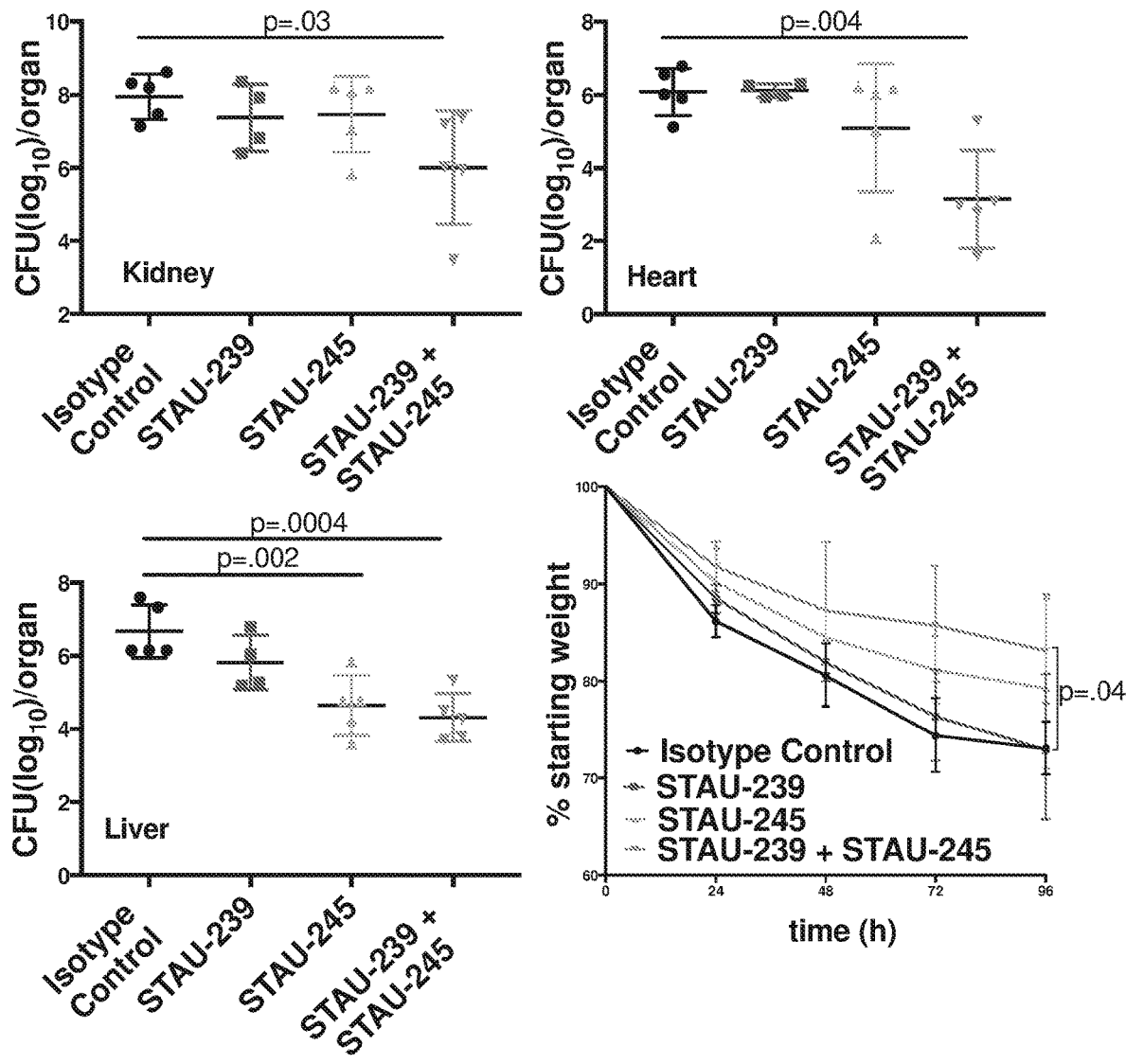
FIG. 6. Isd-specific antibodies reduce bacterial burden in a murine model of S. aureus USA300 infection. Seven-week old female BALB/c mice were inoculated retro-orbitally with an O.D. of 0.4 suspension (~10$^7$ CFU) S. aureus strain USA300. Mice were given antibodies by the IP route two hours before infection. After ninety-six hours, the heart, livers, and kidneys of the infected mice were harvested in cold PBS. CFU counts were determined by serial dilution plating on TSA. For CFU counts, statistics were determined by a Kruskal-Wallis non-parametric test with multiple comparisons to the isotype control. For weight loss, statistical significance was determined using a two-way ANOVA with Bonferroni's posttest to correct for repeated measures.

Human mAb prophylaxis against *S. aureus* in a septic model of murine infection. To determine the in vivo efficacy of the antibody panel, mAbs from each competition-binding group were tested in a septic mouse model of *S. aureus* infection. For initial testing, mAbs were combined at a 1:1 mixture and injected into mice via the intraperitoneal route before retro-orbital inoculation with *S. aureus*. Two IsdA-specific mAbs, STAU-239+STAU-245, combined to reduce the bacterial burden by 102-fold in the kidneys and liver compared to the isotype control and 81-fold in the heart (FIG. 2A). To determine if either STAU-239 or STAU-245 alone was sufficient for this effect, each antibody was tested individually. STAU-239 did not reduce bacterial burden significantly in any organ tested, whereas STAU-245 reduced bacterial burden in the liver and kidneys alone. These data indicate that combining both antibodies results in a cooperative effect. The 12-fold reduction in bacterial burden in the kidneys caused by STAU-245 is also consistent with previously published data showing that an ΔisdA mutant *S. aureus* strain leads to a 10-fold reduction in bacterial burden (Pishchany et al., 2009). This finding indicated that STAU-245 possesses inhibitory function and suggests that the addition of STAU-239 results in an additive effect not solely dependent on blocking IsdA. The weight loss for each mouse also was monitored over the 96-hour period of infection, and percent weight loss is graphed. The STAU-239+STAU-245 mouse group lost the least amount of weight, followed next by the STAU-245 treatment group (FIG. 2B). These antibodies were tested further in a septic model of infection using a MRSA strain of *S. aureus*, USA300 (FIG. 6). These data were consistent with the infection data with strain Newman, as STAU-239+STAU-245 reduced bacterial burden in the heart, kidneys, and livers of infected mice.

Inhibition of *S. aureus* hemoglobin-dependent growth. To test the hypothesis that the efficacy of STAU-239+STAU-245 in vivo was the result of inhibition of hemoglobin-dependent iron-acquisition, the ability of these antibodies to block *S. aureus* utilization of hemoglobin as the sole iron source was tested in vitro with human hemoglobin (FIG. 3). *S. aureus* was incubated overnight in iron-chelated conditions. The bacterial suspension was normalized for density by $OD_{600}$ and subcultured into fresh tubes to grow for 34 hours with the addition of: 1) no hemoglobin, 2) hemoglobin, 3) hemoglobin+STAU-239, 4) hemoglobin+STAU-245, or 5) hemoglobin+the STAU-239+STAU-245 combination. Hemoglobin was used at a concentration of 20 nM and antibody at a concentration of 2 μg/mL (molar ratio of Ab to Hb was 665 to 1).

Untreated samples without hemoglobin did not grow, due to a lack of available hemoglobin for use as an iron source (Pishchany et al., 2014a). When hemoglobin was added, samples grew to an $OD_{600}$ greater than 1.0 as hemoglobin-dependent growth requires the Isd system (Torres et al., 2006; Pishchany et al., 2014b). All antibody treated groups led to a partial inhibition of *S. aureus* growth in comparison with hemoglobin treatment. The inability of the antibodies to completely reduce *S. aureus* growth in the presence of hemoglobin (similar to levels shown with no Hb and no mAb) suggested that hemoglobin blocking might not be the only mechanism by which the antibodies inhibited bacterial growth.

STAU-239+STAU-245 binding site and conservation on IsdA. Hydrogen-deuterium exchange mass spectrometry (HDX-MS) was performed to identify the binding sites of STAU-239 and STAU-245. HDX-MS identifies amino acids involved in protein-protein interactions by comparing the relative deuterium-uptake in two different states. HDX-MS breaks the antigen into overlapping peptides and identifies peptides with decreased deuterium accumulation where the antibody binds the antigen. The Fab fragments of STAU-239 and STAU-245 were tested individually for binding to IsdA and both binding sites were found within the NEAT domain of IsdA (FIG. 4A, FIG. 7A). The crystallized structure of the NEAT domain binding to heme was modeled with the NEAT domain (green) (Grigg et al., 2007), heme (red), and binding site for STAU-239 (orange) and STAU-245 (blue) shown (FIG. 4B). STAU-239 bound near the heme-binding pocket of IsdA-N1, to peptide residues H158-V161 and P162-Y166. STAU-245, however, bound to peptides (N120-L126, A127-T128) on the far region of IsdA-N1, away from the heme-binding site as modeled on the crystal structure in blue (FIG. 4B, FIGS. 7B-C).

Because STAU-239 binds both IsdA and IsdB (Table A), the inventors investigated genetic variation within the binding site of STAU-239. The conservation of each amino acid was determined by comparing the *S. aureus* strain Newman IsdA protein sequence against predicted protein sequences from 42,949 publicly available *S. aureus* genomes sampled from over 2,500 MLST sequence types (STs) (Petit and Read, 2018). Genomes without a predicted full length IsdA protein owing to gaps in de novo assembly were excluded. The IsdA protein was extracted from the remaining 42,522 genomes and clustered based on 100% identity into 556 unique protein sequences. The most common sequence had 16,416 strains (including Newman) and the second most common had 7,420 strains. There were 29 strains (0.06%) that had predicted amino acid substitutions compared to the canonical Newman sequence in positions 159 and 167 (FIG. 4C). At amino acid position 163, 18 ST22 strains shared a glutamine to arginine mutation (Q163R). Q163 is also a surface residue and the position farthest from heme in the binding site, which may explain the variability at this position (FIG. 8). The remaining mutations were shared in 4 or fewer strains. Five of the amino acid sites were invariant in the 42,522 strains, underscoring the conservation of this epitope across *S. aureus*.

Figure 9:
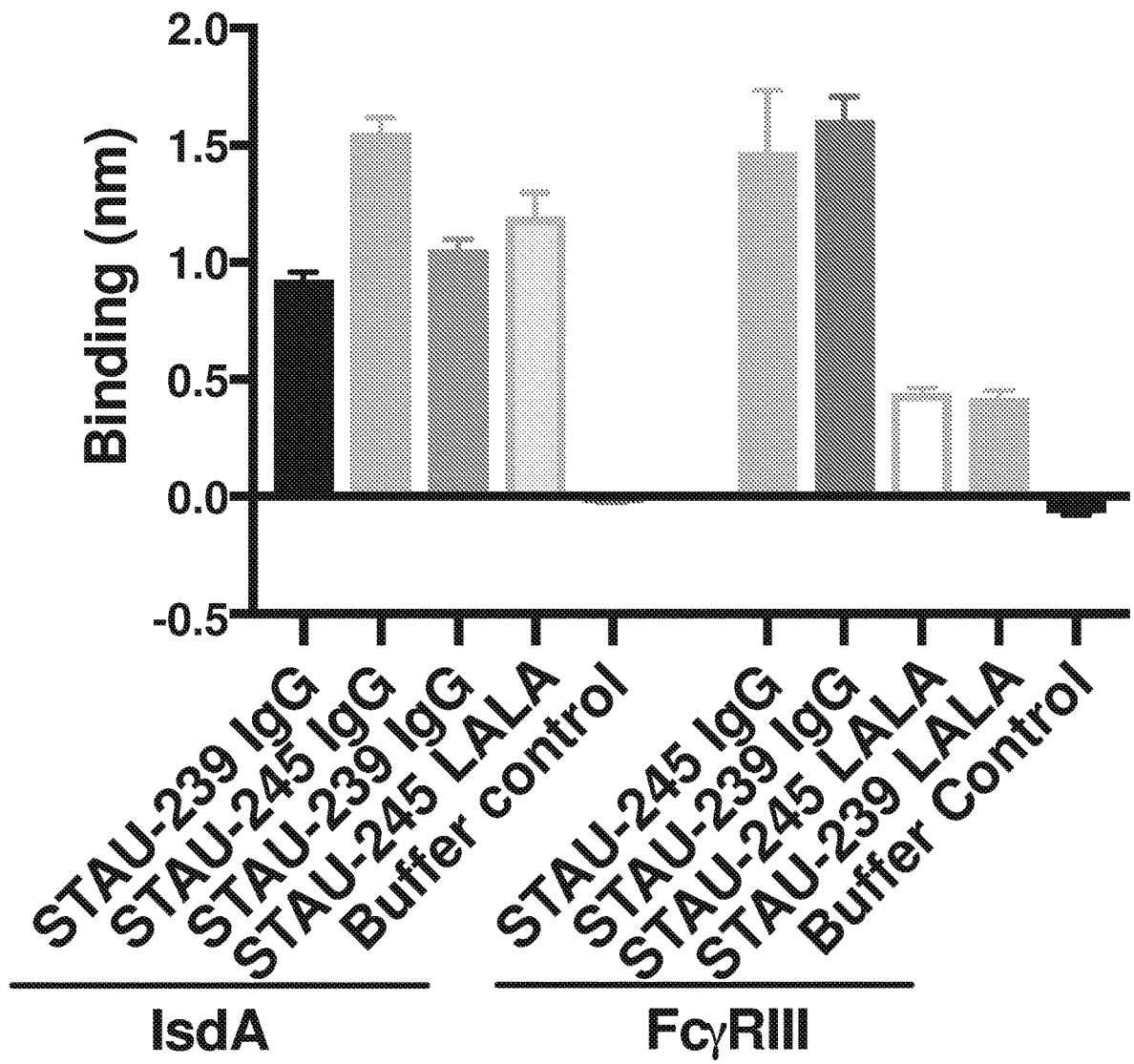
FIG. 9. STAU-239+STAU-245 IgG or LALA variant binding to IsdA or FcγRIII. Recombinant mAbs were expressed in Expi293F cells and were tested by biolayer interferometry to ensure the LALA variant antibodies still bound to the Isd antigen but lost binding to recombinant FcγR.
Figure 10:
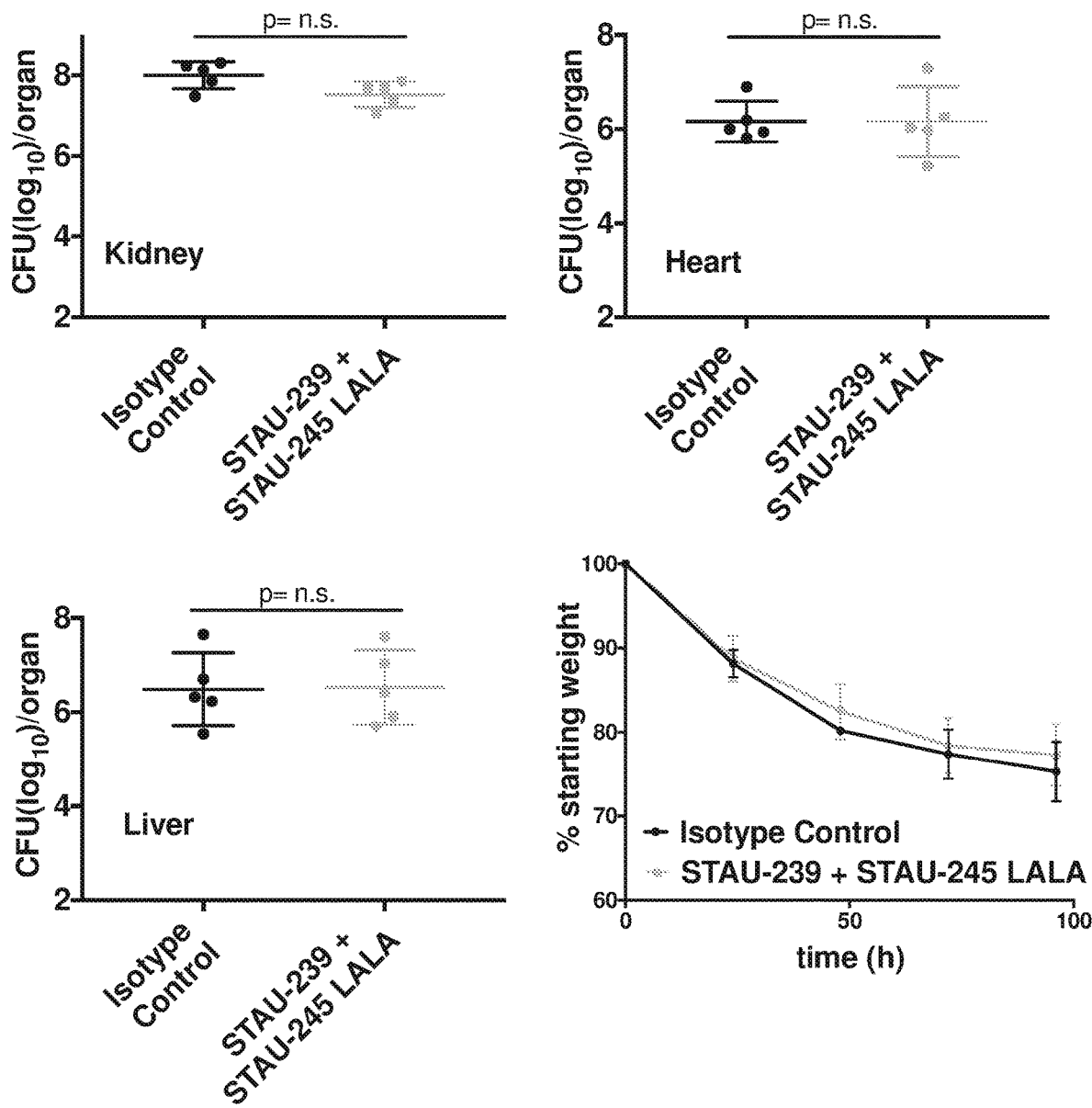
FIG. 10. Fc mutants do not reduce bacterial burden in a murine model of *S. aureus* USA300 infection. Seven-week old female BALB/c mice were inoculated retro-orbitally with an O.D. of 0.4 suspension (~$10^7$ CFU) *S. aureus* strain USA300. Mice were given STAU-239+245 LALA (L234A, L235A) variant antibodies by the IP route two hours before infection. After ninety-six hours, the heart, livers, and kidneys of the infected mice were harvested in cold PBS. CFU counts were determined by serial dilution plating on TSA. For CFU counts, statistics were determined by a Kruskal-Wallis non-parametric test with multiple comparisons to the isotype control. For weight loss, statistical significance was determined using a two-way ANOVA with Bonferroni's posttest to correct for repeated measures.

Prophylaxis against *S. aureus* in a septic model of murine infection with antibodies containing Fc mutations. The Fc region of an IgG antibody binds to Fc receptors and mediates secondary functions such as phagocytosis and ADCC (Mimmerjahn & Ravetch, 2007). To test the contribution of Fc-mediated effector functions in vivo, variant STAU-239+STAU-245 antibodies were made in which the leucine residues at positions 234 and 235 of the CH2 domain were mutated to alanine (L234A/L235A or LALA). These substitutions prevent antibody binding to FcγR1, FcγRII, or FcγRIIIa (Wines et al., 2000; Hezareh et al., 2001; Hessell et al., 2007). The recombinant mAbs were tested by BLI to ensure the antibodies still bound to the Isd antigen but lost binding to recombinant FcγR (FIG. 9). STAU-239+STAU-245 LALA were tested next in the septic murine model of infection in comparison with STAU-239+STAU-245 IgG (FIG. 5). The inventors did not detect a significant difference in bacterial burden between STAU-239+STAU-245 LALA and the isotype control treatment in the heart, liver and kidneys. This finding indicates that these antibodies employ Fc-mediated functions to reduce bacterial burden in the systemic *S. aureus* model. These variant antibodies also were tested further in a septic model of infection using the MRSA strain of *S. aureus*, USA300 (FIG. 10). No significant difference in bacterial burden was detected between the LALA variant antibodies and the isotype control group.

TABLE A

Characterization of Isd-reactive antibodies

| Isd binding pattern of antibody[a] | STAU antibody | Subject # | IgG subclass | Light chain | $EC_{50}$ (µg/mL) of indicated mAb | | |
|---|---|---|---|---|---|---|---|
| | | | | | IsdA | IsdB | IsdH |
| A/B/H | 307 | 1 | 1 | λ | 0.01 | 0.00028 | 0.00001 |
| | 399 | 1 | 2 | λ | 8.7 | 0.53 | 0.95 |
| | 37 | 2 | 1 | κ | 3.8 | 16.1 | 17.5 |
| A/H | 147 | 1 | 2 | λ | 0.01 | > | 0.8 |
| | 407 | 1 | 1 | λ | 1.6 | | 3.1 |
| B/H | 281 | 3 | 1 | κ | >[c] | 0.002 | 0.0027 |
| | 328 | 1 | n.d.[b] | λ | | 0.08 | 0.06 |
| | 389 | 1 | n.d. | λ | | 0.13 | 0.34 |
| A/B | 239 | 1 | 1 | λ | 0.07 | 0.001 | > |
| | 229 | 1 | 3 | λ | 0.7 | 0.01 | |
| | 221 | 1 | 1 | λ | 0.03 | 1.9 | |
| | 218 | 1 | 1 | κ | 0.08 | 4.1 | |
| | 201 | 1 | 1 | λ | 0.26 | 9.5 | |
| | 299 | 1 | 2 | λ | 0.22 | 12.7 | |
| | 402 | 1 | 1 | λ | 8.2 | 3.4 | |
| | 138 | 4 | 1 | n.d. | 5.9 | 9.5 | |
| | 401 | 1 | 1 | λ | 25.1 | 3.7 | |
| | 280 | 1 | 1 | κ | 52.1 | 7.6 | |
| H | 139 | 4 | 1 | λ | > | > | 2.7 |
| B | 75 | 5 | 1 | κ | > | 0.02 | > |
| | 64 | 5 | 1 | κ | | 0.14 | |
| | 141 | 4 | 1 | κ | | 10.2 | |
| A | 158 | 1 | 1 | κ | 0.01 | > | |
| | 231 | 1 | 1 | λ | 0.9 | | |
| | 181 | 1 | 4 | κ | 0.7 | | |
| | 245 | 1 | 1 | κ | 0.2 | | |

TABLE A-continued

Characterization of Isd-reactive antibodies

| Isd binding pattern of antibody[a] | STAU antibody | Subject # | IgG subclass | Light chain | EC$_{50}$ (μg/mL) of indicated mAb | | |
|---|---|---|---|---|---|---|---|
| | | | | | IsdA | IsdB | IsdH |
| | 22 | 6 | 1 | κ | 0.3 | | |
| | 228 | 1 | 1 | κ | 3.2 | | |
| | 149 | 1 | 1 | κ | 0.2 | | |

[a]Indicates the binding pattern of each antibody based on IsdA, IsdB, or IsdH protein binding.
[b]n.d. indicates the experiment was repeated but the subclass or light chain could not be determined.
[c]> symbol indicates binding was not detected at the maximal concentration tested of 20 μg/mL.

TABLE S1

Summary of human subject information

| Subject Number | Age | Sex | Race | Invasive Disease | Clinical diagnosis |
|---|---|---|---|---|---|
| 1 | 20 | F | White | MSSA[1] | Cellulitis and osteomyelitis |
| 2 | 9 | M | African American | MSSA | Septic arthritis and osteomyelitis |
| 3 | 41 | M | White | Zika[2] | N/A |
| 4 | 46 | M | African American | MRSA[3] | Endocarditis |
| 5 | 11 | F | White | MSSA | Sepsis and pyomyositis |
| 6 | 15 | M | White | MSSA | Sepsis and multifocal osteomyelitis |

[1]MSSA indicates methicillin sensitive *Staphlococcus aureus*
[2]Otherwise healthy subject with an unrelated history of recent viral infection. There was no specific medical history of *S. aureus* infection in this subject. The inventors used the sample from a healthy subject as a matter of convenience. Since many subjects in the healthy adult population have been colonized on infected with *S. aureus* in the past, it is expected that many healthy subjects have circulating memory B cells reacting with *S. aureus* antigens.
[3]MRSA indicates methicillin resistant *Staphlococcus aureus*

Example 3—Discussion

*S. aureus* continues to grow as a public health threat, with no licensed vaccine for prevention. Diverse bacterial components have been proposed and studied as candidate *S. aureus* vaccines including toxins, adherence factors, lipoproteins, and surface proteins (Foster et al., 2013; Diep et al., 2014; Rouha et al., 2015; O'Riordan & Lee, 2004). Inhibiting the capacity of bacterial surface proteins involved in the nutrient acquisition of iron is a decisive way to interrupt the pathogenesis of *S. aureus*. Indeed, previous studies have shown that passive transfer of anti-Isd antibodies or active immunization with IsdB, IsdA, or IsdH proteins alone or as a cocktail can reduce bacterial burden in multiple infection models including mice, rats, and macaques (Kuklin et al., 2006; Kim et al., 2010; Ebert et al., 2010; Joshi et al., 2014; Stranger-Jones et al., 2006; Clarke et al., 2006).

Multiple studies following serum antibody response to *S. aureus* infection have identified a separate Isd protein of emerging importance, IsdA, as being an immunogenic protein in bacteremic patients (Verkaik et al., 2010a; Ghasemzadeh-Moghaddam et al., 2017) or in young children with *S. aureus* colonization of the nares (Verkaik et al., 2010b). IsdA also has been identified as important for biofilm formation in epidermal models and on polysterene surfaces (Den Reijer et al., 2016). IsdA-reactive antisera react with and opsonize both *S. aureus* and *S. agalactiae*, suggesting that IsdA is a conserved antigen across genera (Stapleton et al., 2012). Furthermore, It has been unclear whether antibodies targeting Isd proteins mediate bacterial inhibition purely by blocking nutrient metal acquisition or whether other antibody functions can be equally important (Balderas et al., 2016). Studies presented here reveal that IsdA could be a plausible component of a preventative vaccine strategy, not only due to its ability to interfere with heme-iron acquisition, but also by stimulating Fc-mediated protective effects.

In this report, the inventors searched for naturally occurring human Isd-reactive antibodies after infection and identified the first panel of IsdA- and IsdH-specific human mAbs. This included antibodies that bound to all three Isd surface proteins, highlighting the human capacity to mount a broadly reactive humoral response to iron-binding proteins. Two of the identified IsdA mAbs showed a cooperative protective effect in vivo, which appears to be due to each antibody using a distinct mechanism of action. STAU-239 partially inhibited the in vitro hemoglobin-dependent growth of *S. aureus* and bound to the heme-blocking site of IsdA, however, this only partially explained the in vivo phenotype observed. IgG variants of STAU-239+STAU-245 containing the L234A, L235A ("LALA") variant mutations that functionally abrogate binding to Fc receptors lacked the ability to protect mice from *S. aureus* infection. This finding suggests that antibody effector functions, especially Fc-mediated functions, play a critical role in the action of antibodies reducing *S. aureus* infection. The combination of iron-blocking activity along with the addition of Fc-mediated functions combines to inhibit *S. aureus* through multiple mechanisms. This proof of principle suggests that blocking *S. aureus* pathogenesis via different pathways may be the best chance to inhibit disease caused by such a multifaceted pathogen.

TABLE 1

NUCLEOTIDE SEQUENCES FOR ANTIBODY VARIABLE REGIONS

| Clone | Variable Sequence Region | SEQ ID NO: |
|---|---|---|
| STAU-37 heavy | caggtgcagctggtggagtctgggggaggcttggtcaagcctggagggtccctgagactctcctgtgcagcctct ggattcaccttcagtgactactacatgagctggatccgccaggctccagggaaggggctggagtgggtttcatac attagtagtagtggtagtaccatatactacgcagactctgtgaagggccgattcaccatctccagggacaacgcc aagaactcactgtatctgcaaatgaacagcctgagagccgaggacacggctgtgtattactgtgcgagagagac | 1 |

TABLE 1-continued

NUCLEOTIDE SEQUENCES FOR ANTIBODY VARIABLE REGIONS

| Clone | Variable Sequence Region | SEQ ID NO: |
|---|---|---|
| | cccccgacgtataactggaatggggcttgaggactactactacggtatggacgtctggggccaagggaccctgg tcaccgtctcctca | |
| STAU-37 light | Not available | 2 |
| STAU-64 heavy | gaggtgcagctggtggagtctgggggaggcctggtcaagccggggggtccctgagactctcctgtgcagcctc tggattcagcttcagttactatagcatgaattgggtccgccaggctccagggaaggggctggagtggatctcatc gattagtagtagtggtgaatacatatattacgcagattcagtgaagggccgattcaccatctccagagacaacgc cgagaactcactgtatctgcaaatgaacagcctgagagccgaggacacggctgtgtattactgtgcgaaagtgg tttctcagcagtcccttgattactggggccagggaaccctggtcaccgtctcctca | 3 |
| STAU-64 light | gacatcgtgatgacccagtctccatcctccctgtctgtatctgttggagacagagtcaccatcacttgccgggcaa gtcagagcattagtacctatttaaactggtatcagcagaaaccagggaaagcccctaagctcctgatctctggtg gatccaatttgcaaagtggggtcccatcaaggttcagtggcagtggatctgggacagatttcactctcaccatcat cagtctccaacctgaagattttgcaacttactactgtcaacagagttacagtacccggtacagttttggccagggg accaagctggagatcaaa | 4 |
| STAU-75 heavy | cagctgcagctgcaggagtcgggcccaggactggtgaagccttcggagaccctgtcctcacctgcactgtctct ggtggctccatcagcagtgtttcttactactggggctggatccgccagcccccagggaaggggctggagtggtt gcgtccatattttatagtgggagcacaaagtacaacccgtccctcgagagtcgagtcaccatatcagtagacacg tccaagaaccagttcttcctgaagctgacctctgtgaccgccgcagacacggctgtatattactgtgcgagacaa atatattactacgaacttgaagaatttgactactggggccagggaaccctggtcaccgtctcctca | 5 |
| STAU-75 light | Not available | 6 |
| STAU-138 heavy | Not available | 7 |
| STAU-138 light | cagtctgtgttgacgcagccgccctcagtgtctgcggccccaggacagaaggtcaccatctcctgctctggaagc agctccaacattgggaataattatgtatcctggtaccagcagctcccaggaacagcccccaaactcctcatttat gacaataataagcgaccctcaggggattcctgaccgattctctggctccaagtctggcacgtcagccaccctggc atcaccggactccagactggggacgaggccgattattactgcggaacatgggatagcagcctgagtgctgggt attcggcggagggaccaagctgaccgtccta | 8 |
| STAU-139 heavy | gaggtgcagctggtgcagtctggagcagaggtgaaaaagcccggggagtctctgaagatctcctgtaagggttc tggatacagctttaccagctactggatcggctgggtgcgccagatgcccgggaaaggcctggagtggatgggga tcatctatcctggtgactctgataccagatacgcccgtccttccaaggccaggtcaccatctcagccgacaagtc catcagcaccgcctacctgcagtggagcagcctgaaggcctcggacaccgccatgtattactgtgcgagaccgc cgggactacgcggagatgcttttgatatctggggccaagggaccctggtcaccgtctcctca | 9 |
| STAU-139 light | cagtctgccctgactcagcctccctccgcgtccgggtctcctggacagtcagtcaccatctcctgcactggaacca gcagtgacgttggtggttataactatgtctcctggtaccaacagcacccaggcaaagcccccaaactcatgattt atgaggtcagtaagcggccctcaggggtccctgatcgcttctctggctccaagtctggcaacacggcctccctga ccgtctctgggctccaggctgaggatgaggctgattattactgcagctcatatgcaggcagcaacaatttggtgtt cggcggagggaccaagctgaccgtccta | 10 |
| STAU-147 heavy | gaggtgcagctggtgcagtctggaacagaggtgaaaaagcccggggagtctctgaggatctcctgtacgggttc taaacacatgttttccaattactggatcgcctgggtgcgccagagggcccgggaaaggcctggagtggatgggga tcatctaccctcctgacgctgataccagatacgcccgtccttcaaaggccaggtcaccatctcagccgacaagg ccaccaacaccgcctacctgcagtggagcagcctgagggcctcggacaccgccatgtattactgtgctaccacg ggaggatcaggaacctatttagattactttgactactggggccagggaaccctggtcaccgtctcctca | 11 |
| STAU-147 light | Not available | 12 |
| STAU-201 heavy | caggttcagctggtgcagtctggacctgaggtgaagaagcctggggcctcagtgaaggtctcctgcaaggcttct ggttacacctttaccaactatggtctcacctgggtgcgacaggcccctggaaaaggacttgagtggattggatgg atcagcccttacactgggcgcgcaaagtttgccctgaagttccagggcagattcaccttgaccacagacacatcc acgaccacagcctacatggaggtgaggagcctgaaatctgacgactcggccgtgtattactgcgcgagggaag ggattaaagatgctagtgcttttgacttctggggccagggaaccctggtcaccgtctcctca | 13 |
| STAU-201 light | cagtctgccctgactcagcctgcctccgtgtctgggtctcctggacagtcgatcaccatctcctgcactggaaccg gcagtgacattgtggttataaccatgtctcctggtaccaccattacccaggcaaagcccccaaactcttgattttt ggggtcactcatcgtccctcaggtgtttctgatcgcttctctggctccaagtctggcgtcacggccttcctgaccatc tctgggctccaggctgaggacgaggctgattattactgcagctcatatacagacaacacttctgggtgtttggcg gggggaccaaggtgaccgtccta | 14 |
| STAU-218 heavy | caggtcaccttgaaggagtctggtcctgtagtggtgaaacccacagagaccctcacgctgacctgcaccgtctct gacgtctcactccgcaatgttcaaatgggtgtgagctggatccgccagccccagggaaggcccctggagtggctt gcacacatcttttcgcatgacgaaaaggcctacgttacatctctggagaaccggctcaccatctccagggacacc | 15 |

TABLE 1-continued

NUCLEOTIDE SEQUENCES FOR ANTIBODY VARIABLE REGIONS

| Clone | Variable Sequence Region | SEQ ID NO: |
|---|---|---|
| | tccaacagtcaggtggtcctgaccatgacgaacatggaccctgtggacacaggcacatattactgtgcacggat acgttctacttcaggggaagaggaggatccttttgctttctggggccagggacactggtcaccgtctcctca | |
| STAU-218 light | gacatccagatgacccagtctcttcctccctgtctgcatctgttggagacagggtcaccatcacttgccgggcca gtcagagtgtcactacctggttggcctggtatcagcagaaaccagggaaagcccctaaactcctaatctatagtg cctcaagttttggaaagtggggtcccatcaaggttcagcggcagtggatctgggacagacttcactctcaccatca gtaacctgcagcctgatgactttgcaacttattactgccaacagtatcgttttattggacgttcggccaagggacc aaggtggaaagcaag | 16 |
| STAU-221 heavy | caggtcaccttgagggagtctggtcctgcgctggtgaaacccacacagaccctcacactgacctgcaccttctct gggttctcacttaccagtagtggaatgtgtgtgcctggatccgtcagcccccaggaaggccctggagtggcttg cactcattgattgggatgatgataaatactacatcacatctctaaagaccaggctcatcatctccaaggacacct ccaaaaaccaggtggtccttacaatgaccaacatggaccctgtggacacagccacgtattactgtgcacggacg caaagtggatatagtggctactacgttgactactggggccagggaaccctggtcaccgtctcctca | 17 |
| STAU-221 light | cagtctgtgctgactcagccaccctcagcgtctgggaccccgggcagaaggtcaccatctcttgttctggaagc agctccaacatcggaagtaatactgtaaactggtaccagcagctcccaggaacggcccccaaactcctcatcta tagtaatgataagcggccctcaggggtccctgaccgattctctggctccaagtctggcacctcagcctccctggcc atcagtgggctccagtctgaggatgaggctgattattactgttcagcgtgggatgacagcctgaatggtcgttatg tcttcggaactgggaccaaggtcaccgtccta | 18 |
| STAU-229 heavy | gaggtccagctggtacagtctggggctgaggtgaagaagcctggggctacaatgaaaatctcctgcaaggtttc tggataccccttcaccgactactacatgcactgggtgcaacaggcccctggaaaagggcttgagtggatgggac ttattgatcctgaagatggtgaaacaaactacgcagagaagttccagggcagagtcaccataaccgcggacac gtctacagacacagtctacatggaactgagcagctgagatctgaggacacggccgtctatttctgtgcaaaacc acactgtagtagtaggacctgccagcgggtgtcggggtactacttcggtatggacgtctgggcaagggacccct ggtcaccgtctcctca | 19 |
| STAU-229 light | cagtctgccctgactcagcctccctccgcgtccgggtctcctggacagtcagtcaccatctcctgcactggaagca gcaatgacgttggtgattataactttgtctcgtggtaccaacaacacccaggcaaaccccccaaactcatgattta tgaggtcactaagcggccctcaggggtccctgatcgcttctttggctccaagtctggcaacacggcctccctgacc gtctctgggctccaggctgacgatgaggctgattattattgcagctcatatgcaggcggcaactctgtggtattcg gcggtgggaccaagcttaccgtccta | 20 |
| STAU-239 heavy | caggtcagctggtgcagtctggggctgaggtgaagaagcctgggtcttcggtgaaggtctcctgcagggcctct ggaggccccttcaacacctatgttatcacctgggtgcgacaggcccctggacaaggtcttgagtggatgggggg aatcgtccctgtctttaatacatcacactccgcacagaagttccagggcagagtcaagattccgcgagacacatc caccaacactgtctcatatggaattgaccagcctaacatttgaggacacggccgtatacttttgcgcgcgagatgg cgccgcagctcccctgaattggtacgaccctggggccagggaaccctggtcaccgtctcctca | 21 |
| STAU-239 light | tcctatgtgctgactcagccaccctcggtgtcgctggccccagggcagacggccacgcttacctgtgggggaaac aatattggcagtaaaagtgtacactggtaccagaagaagccaggccaggcccctgtgctggtcgtctatgatgtc agggaccggccctctgggatccccgagcgattctctggctccagctctgagaacacggccaccctgaccctcagc agggtcgaagccgaggatgaggccgactattactgtcaggtgtgggaaagtactacttctcatgtgatattcggc ggagggaccaagctgaccgtccta | 22 |
| STAU-280 heavy | gaggtgcagctggtggagtcgggggggaggcttggtacagactggagggtccctgagactctcctgtgcagcctc tggattcacctttagtagatataacatgaattgggtccgccaggctccaggaaggactggagtgggtttccttc attagtgctagagtagtagcatatactacgcagactctgtgaagggccgattcaccatctccagagacaatgcc aagaactcactggatctgcaaatgaacagcctgagagacagccggctgtatattttctgtgtgagagagga tgctgcgattttggagtggggagttggttcgaccctggggccagggaaccctggtcaccgtctcctca | 23 |
| STAU-280 light | gaaattgtgatgactcagtctccagccaccctgtctgtgtctccaggggaaagagccaccctctcctgcagggcc agtcagagtgttagtagcaacttagcctggtaccagcagaaacctggccaggctcccaggctcctcatctatggt gcatccaccagggccactggtatcccagccaggttcagtggcagtgggtctgggacagagttcactctcaccatc agcagcctgcagtctgaagattttgcagtttatttctgtcaggagtataatgactggcccctgtacacttttggcca gggggaccaagctggagatcaaa | 24 |
| STAU-281 heavy | caggtgcagctggtgcagtctggggctgaagtgaagaggccagggtcctcggtgagggtctcctgcaaggactc tggagacagcttcagaagatatgttatcaattgggtgcgacaggcccctggacaagggcttgagtggatgggag ggatcatccctatctttgacaaagcaaagtccgtccagaaattccaggacagactcaccattaccgcggacgaa tctacgagcacatcgtacatggagttgagcagtctgacatctgaagacacggccgtgtattactgtgcgagaaa agaagatggacgtagagatgatgttttttgatatctggggccaagggaccctggtcaccgtctcctca | 25 |
| STAU-281 light | gaaatagtgatgacgcagtctccagccacccctgtctgtgtctctgggagaaagagccaccctctcctgcagggcc agtcacagtgttggcagcagcttggctggtatcagcagaaacctggccaggctcccaggctcctcatctatggt gtctccaccagggccactggtatcccagccaggttcagtggcagtgggtctgcgacagagttcactctcaccatc agcagcctgcagtctgaggatttagcagcttatcactgtcagcagtatgataactggccattcactttggccagg ggaccaagctggagatcaaa | 26 |
| STAU-299 heavy | caggtcaccttgagggagtctggtcctgcgctggtgaagccacagagaccgtcacactgacctgcaccttctct gggttctcactcagcactagtggaatgtgtgtgacctggctccgtcagcccccaggaaggccctggagtggctt gcactcattgattgggaggatgataaatactacagcacatctctgaagaccaggttcaccatctccaaggacacc tccaaaaaccaggtggtccttacaatgaccaacatggaccctgtggacacagccacgtattactgtgcacggac cccaacgtatcgcggggcttttgatatgtggggccaagggaccctggtcaccgtctcctca | 27 |

TABLE 1-continued

NUCLEOTIDE SEQUENCES FOR ANTIBODY VARIABLE REGIONS

| Clone | Variable Sequence Region | SEQ ID NO: |
|---|---|---|
| STAU-299 light | cagtctgtgctgactcagccaccctcagcgtctgggaccccgggcagagggtcaccatctcttgttctggaagcacctccaacatcggaagtaatactgtaaactggtaccagcagctcccaggaacggccccccaactcctcatctataataataatcagcggccctcaggggtccctgaccgattctctggctccaagcctggcacctcagcctccctggccatcagtgggctccagtctgaggatgaggctgattattactgcgcagcatgggatgacagcctgaatggtgtggtattcggcggagggaccaagctgaccgtccta | 28 |
| STAU-307 heavy | caggtgcagctggtgcagtctggggctgaggttaagaagactgggtcctcggtgaaggtctcatgcacggcttcaggagccaccttcaacaccaatgatctcatgtgggtgcgacaggcccctggacaaggacttgagtggatgggggggatcgtcccagttttttggaagaccgaaatacgcaaagaagttccatggcagactcatcataagtgcggacgaattcacaaccaccttctacatggaactgaccagcctgacattcgacgacacggccatatattattgcgcgagaagtgcagtacagaatcacccattcagcatattgacttttggggccagggaaccctggtcaccgtctcctca | 29 |
| STAU-307 light | tcctatgtgctgactcagccaccctcggtgtcagtggcccaggacagacggccacgattacctgtggggagacaacattgcgactttcagtgtgcactggtaccggcagaagccaggccaggcccctgtgttggtcgtctatgatgatctcgaccgggcctcagggatccctgcgcgattctccggctccaattctgggaacacggccaccctgacaatcagcagagtcgagcccgggatgaggccgactatttctgtcaggtgtgggaaatttctagtgacgaatatgtcttcggaactgggaccagtgtcaccgtcctc | 30 |
| STAU-328 heavy | caggtgcagctacagcagtggggcgcaggactgttgaagccttcggagaccctgtcctcacctgcgctgtctatggtgggtccttcagtggttactactggagctggatccgccagcccccagggaaggggctggagtggattgggaaatcaatcatagtggaagcaccaactacaacccgtccctcaagagtcgagtcaccatatcagtagacacgtccaagaaccagttctccctgaagctgagctctgtgaccgccgcggacacggctgtgtattactgtgcgagagatgtcggtgaccggtactactttgactactggggccagggaaccctggtcaccgtctcctca | 31 |
| STAU-328 light | cagtctgccctgactcagcctgcctccgtgtctgggtctcctggacagtcgatcaccatctcctgcactggaaccagcagtgatgttgggagttataaccttgtctcctggtaccaacagcacccaggcaaagcccccaaactcatgatttatgagggcagtaagcggccctcaggggtttctaatcgcttctctggctccaagtctggcaacacggcctcctgacaatctctgggctccaggctgaggacgaggctgattattactgctgctcatatgcaggtagtagcacttttgtggttcggcggagggaccaagctgaccgtccta | 32 |
| STAU-389 heavy | caggtgcagctggtgcagtctggggctgaggtaaagcagtctgggtcctcgctgaaggtctcctgtaaggtttctggaggcaatttacggagttatggtatcagttgggtgcgacaggcccctggacaagggcttgagtggatgggagtgatcatccctatctttggagcaccaacctacgcacagaagttccagggcagagttacatttgtcgcggacgatggcaacaatgtagtcttcatggagctgagtagtctgagatctgaggacacggccgtgtattactgtgcgagagattggccctcaattacagtggcggtcgatgctatcaatttcgcaatggacgtctggggccaagggaccctggtcaccgtctcctca | 33 |
| STAU-389 light | cagtctgccctgactcagcctcgctcagtgtccgggtctcctggacagtcagtcaccatatcctgcaccggaaccaacaatgacgttggatcttatgaccatgtctcctggtaccagcagcacccgggcaaagcccccaaattcataatttatgatgtctctacgcggccgtcaggggtccctgatcgcttctctggctccaagtctgacaacacggcctccctgaccatctctgggctccaggctgaggatgaggctgattattactgctgctcatttgcgggcagctacacttatgtcttcggaactgggacgacggtcaccgtcctc | 34 |
| STAU-399 heavy | caggtgcagctggtgcagtctggggctgaggtaaagaagcctgggtcctcgctgaaggtctcctgtaaggtttctggaggcaatttacggagttatggtatcagttgggtgcgacaggcccctggacaggggcttgagtggatgggagtgatcatccctatctttggaacaccaacctacgcacagaagttccagggcagagtcacacttgccgcggacgattcaacaatatagtcttcatggagctgagtagtcttagatctgaggacacggccgtatattactgtgcgagagattggccctcattacagtggcggtcgatgctaccaattacggaatggacgtctggggccaagggaccctggtcaccgtctcctca | 35 |
| STAU-399 light | cagtctgccctgactcagcctcgctcagtgtccgggtctcctggacagtcagtcaccatatcctgcaccggaaccagcaatgacgttggatattatgaccatgtctcctggtaccagcagcacccgggcaaagcccccaaattcataatttatgatgtcagtaagcggccgtcaggggtccctgatcgcttctctggctccaagtctgacaacacggcctccctgaccatctctgggctccaggctgaggatgaggctgattattactgctgctcatttgcaggcagctacacttatgtcttcggaactgggacgaaggtcaccgtcctc | 36 |
| STAU-401 heavy | caggttcagctggtgcagtctggacctgaggcgaggaagcctgggacctcagtgaaggtctcctgcaagacgtctggttacacctttagtagctatggcattgcctgggtgcgacaggcccctggacaagggcttgagtggatgggatgatcagcggttacagtgattacacaatctatgcacagaggctccagggcagagtctccatgaccacagacccatatacgagcacagcctacatggagctgaggagcctgagacctgacgacacggccgtctattactgtgcgaccctgtcgttcggggagttagtggaaaataaacttgacttctggggacagggaaccctggtcaccgtctcctca | 37 |
| STAU-401 light | cagtctgtgctgacgcagccgccctcagtgtctggggcccagggcagagggtcaccatctcctgcactgggaccagctccaatatcggggctgattatgctgtccactggtatcagcagcttccaggaacagcccccaaactcctcatctatggtaccatcaatcggccctcaggggtccctgaccgattctctggctccaggtctggcacgtcagcctccctggccatcactgggctccagtctgatgatgaggctgattactactgccagtcctatgacagcagcctgagcggctctgtggttttcggtggagggaccaagctgaccgtgcta | 38 |
| STAU-402 heavy | cagctgcagctgcaggagtcgggcccaggactggtgaagccttcggagaccctgtcctcacctgcactgtctctggtggctccatcagcagtagtagttactactggggctggatccgccagcccccagggaaggggctggagtggattgggagtatctattatagtgggagcacctactacaacccgtccctcaagagtcgagtcaccatatccgtagacacgtccaagaaccagttctccctgaagctgagctctgtgaccgccgcagacacggctgtgtattactgtgcgagaccaatagcagtggctggtcgtactactttgactactggggccagggaaccctggtcaccgtctcctca | 39 |

TABLE 1-continued

NUCLEOTIDE SEQUENCES FOR ANTIBODY VARIABLE REGIONS

| Clone | Variable Sequence Region | SEQ ID NO: |
|---|---|---|
| STAU-402 light | cagtctgtgctgacgcagccgccctcagtgtctggggccccagggcagagggtcaccatctcctgcactgggacc agctccaatatcggggctgattatgatgtccactggtatcagcagcttccaggaacagcccccaaactcctcatct atggtaacatcaatcggccctcaggggtccctgaccgattctctggctccaggtctggcacgtcagcctccctggc catcactgggctccaggctgatgatgaggctgattactactgccagtcctatgacagcagcctgagcggtctgt ggttttcggtggagggaccaagctgaccgtgcta | 40 |
| STAU-407 heavy | cagctgcagctgcaggagtcgggcccaggactggtgaagcccctcggagaccctgtccctcacttgcagtgtctct ggtggctccatcagcaggacgtattactactgggactggatccgccagcccccagggaaggggctggagtggat tgggagtgtctattatagtgggagcacctactacaacccgtccctcaagagtcgagtcaccatgtccgtagacac gtccaagaacctgttctcccctgaagctgagctctgtgaccgccgcagacacggctgtgtattactgtgcgagccat gagtcatggcagcagctgatctcctggggccagggaaccctggtcaccgtctcctca | 41 |
| STAU-407 light | caggctgtgctgactcagccgtcttccctctctgcatctcctggagcatcagccagtctcacctgcaccttacgcag tggcatcaatgttggtatctacaggatatattggtaccagcagaagccagggagtcctccccagtatctcctgag gtacaaatcagactcagataagcatcaggggtctggagtccccagccgcttctctgtgatccaaagatgcttcggc caatgcagggattttactcatctctggcctccagtctgaggatgaggctgactattattgtatgatttggcacagca gcgccgtggcattcggcggagggaccaagctgaccgtccta | 42 |

TABLE 2

PROTEIN SEQUENCES FOR ANTIBODY VARIABLE REGIONS

| Clone | Variable Sequence | SEQ ID NO. |
|---|---|---|
| STAU-37 heavy | QVQLVESGGGLVKPGGSLRLSCAASGFTFSDYYMSWIRQAPGKGLEWVSYISSSGSTIYY ADSVKGRFTISRDNAKNSLYLQMNSLRAEDTAVYYCARETPRRITGMGLEDYYYGMDV WGQGTLVTVSS | 43 |
| STAU-37 light | Not available | 44 |
| STAU-64 heavy | EVQLVESGGGLVKPGGSLRLSCAASGFSFSYYSMNWVRQAPGKGLEWISSISSSGEYIYYA DSVKGRFTISRDNAENSLYLQMNSLRAEDTAVYYCAKVVSQQSLDYWGQGTLVTVSS | 45 |
| STAU-64 light | DIVMTQSPSSLSVSVGDRVTITCRASQSISTYLNWYQQKPGKAPKLLISGGSNLQSGVPSR FSGSGSGTDFTLTIISLQPEDFATYYCQQSYSTRYSFGQGTKLEIK | 46 |
| STAU-75 heavy | QLQLQESGPGLVKPSETLSLTCTVSGGSISSVSYYWGWIRQPPGKGLEWVASIFYSGSTKY NPSLESRVTISVDTSKNQFFLKLTSVTAADTAVYYCARQIYYYELEEFDYWGQGTLVTVSS | 47 |
| STAU-75 light | Not available | 48 |
| STAU-138 heavy | Not available | 49 |
| STAU-138 light | QSVLTQPPSVSAAPGQKVTISCSGSSSNIGNNYVSWYQQLPGTAPKLLIYDNNKRPSGIPD RFSGSKSGTSATLGITGLQTGDEADYYCGTWDSSLSAGVFGGGTKLTVL | 50 |
| STAU-139 heavy | EVQLVQSGAEVKKPGESLKISCKGSGYSFTSYWIGWVRQMPGKGLEWMGIIYPGDSDTRYS PSFQGQVTISADKSISTAYLQWSSLKASDTAMYYCARPPGLRGDAFDIWGQGTLVTVSS | 51 |
| STAU-139 light | QSALTQPPSASGSPGQSVTISCTGTSSDVGGYNYVSWYQQHPGKAPKLMIYEVSKRPSG VPDRFSGSKSGNTASLTVSGLQAEDEADYYCSSYAGSNNLVFGGGTKLTVL | 52 |
| STAU-147 heavy | EVQLVQSGTEVKKPGESLRISCTGSKHMFSNYWIAWVRQRPGKGLEWMGIIYPPDADT RYSPSFKGQVTISADKATNTAYLQWSSLRASDTAMYYCATTGGSGTYLDYFDYWGQGTL VTVSS | 53 |
| STAU-147 light | Not available | 54 |
| STAU-201 heavy | QVQLVQSGPEVKKPGASVKVSCKASGYTFTNYGLTWVRQAPGKGLEWIGWISPYTGRA KFALKFQGRFTLTTDTSTTTAYMEVRSLKSDDSAVYYCAREGIKDASAFDFWGQGTLVTV SS | 55 |
| STAU-201 light | QSALTQPASVSGSPGQSITISCTGTGSDIGGYNHVSWYHHYPGKAPKLLIFGVTHRPSGVS DRFSGSKSGVTAFLTISGLQAEDEADYYCSSYTDNTSWVFGGGTKVTVL | 56 |

TABLE 2-continued

PROTEIN SEQUENCES FOR ANTIBODY VARIABLE REGIONS

| Clone | Variable Sequence | SEQ ID NO. |
|---|---|---|
| STAU-218 heavy | QVTLKESGPVVVKPTETLTLTCTVSDVSLRNVQMGVSWIRQPPGKALEWLAHIFSHDEK AYVTSLENRLTISRDTSNSQVVLTMTNMDPVDTGTYYCARIRSTSGEEEDPFAFWGQGTL VTVSS | 57 |
| STAU-218 light | DIQMTQSPSSLSASVGDRVTITCRASQSVTTWLAWYQQKPGKAPKLLIYSASSLESGVPSR FSGSGSGTDFTLTISNLQPDDFATYYCQQYRFYWTFGQGTKVESK | 58 |
| STAU-221 heavy | QVTLRESGPALVKPTQTLTLTCTFSGFSLTSSGMCVSWIRQPPGKALEWLALIDWDDDKY YITSLKTRLIISKDTSKNQVVLTMTNMDPVDTATYYCARTQSGYSGYYVDYWGQGTLVTV SS | 59 |
| STAU-221 light | QSVLTQPPSASGTPGQKVTISCSGSSSNIGSNTVNWYQQLPGTAPKLLIYSNDKRPSGVP DRFSGSKSGTSASLAISGLQSEDEADYYCSAWDDSLNGRYVFGTGTKVTVL | 60 |
| STAU-229 heavy | EVQLVQSGAEVKKPGATMKISCKVSGYPFTDYYMHWVQQAPGKGLEWMGLIDPEDGE TNYAEKFQGRVTITADTSTDTVYMELSSLRSEDTAVYFCAKPHCSSRTCQRVSGYYFGMD VWGQGTLVTVSS | 61 |
| STAU-229 light | QSALTQPPSASGSPGQSVTISCTGSSNDVGDYNFVSWYQQHPGKPPKLMIYEVTKRPSG VPDRFFGSKSGNTASLTVSGLQADDEADYYCSSYAGGNSVVFGGGTKLTVL | 62 |
| STAU-239 heavy | QVQLVQSGAEVKKPGSSVKVSCRASGGPFNTYVITWVRQAPGQGLEWMGGIVPVFNT SHSAQKFQGRVKISADTSTNTVYMELTSLTFEDTAVYFCARDGAAAPLNWYDPWGQGT LVTVSS | 63 |
| STAU-239 light | SYVLTQPPSVSLAPGQTATLTCGGNNIGSKSVHWYQKKPGQAPVLVVYDVRDRPSGIPE RFSGSSSENTATLTLSRVEAEDEADYYCQVWESTTSHVIFGGGTKLTVL | 64 |
| STAU-280 heavy | EVQLVESGGGLVQTGGSLRLSCAASGFTFSRYNMNWVRQAPGKGLEWVSFISATSSSIYY ADSVKGRFTISRDNAKNSLDLQMNSLRDEDTAVYFCVREDAAIFGVGSWFDPWGQGTL VTVSS | 65 |
| STAU-280 light | EIVMTQSPATLSVSPGERATLSCRASQSVSSNLAWYQQKPGQAPRLLIYGASTRATGIPAR FSGSGSGTEFTLTISSLQSEDFAVYFCQEYNDWPLYTFGQGTKLEIK | 66 |
| STAU-281 heavy | QVQLVQSGAEVKRPGSSVRVSCKDSGDSFRRYVINWVRQAPGQGLEWMGGIIPIFDKA KSVQKFQDRLTITADESTSTSYMELSSLTSEDTAVYYCARKEDGRRDDVFDIWGQGTLVT VSS | 67 |
| STAU-281 light | EIVMTQSPATLSVSLGERATLSCRASHSVGSSLAWYQQKPGLAPRLLIYGVSTRATGIPAR FSGSGSATEFTLTISSLQSEDLAAYHCQQYDNWPFTFGQGTKLEIK | 68 |
| STAU-299 heavy | QVTLRESGPALVKPTETVTLTCTFSGFSLSTSGMCVTWLRQPPGKALEWLALIDWEDDKY YSTSLKTRFTISKDTSKNQVVLTMTNMDPVDTATYYCARTPTYRGAFDMWGQGTLVTVSS | 69 |
| STAU-299 light | QSVLTQPPSASGTPGQRVTISCSGSTSNIGSNTVNWYQQLPGTAPQLLIYNNNQRPSGV PDRFSGSKPGTSASLAISGLQSEDEADYYCAAWDDSLNGVVFGGGTKLTVL | 70 |
| STAU-307 heavy | QVQLVQSGAEVKKTGSSVKVSCTASGATFNTNDLMWVRQAPGQGLEWMGGIVPVFG RPKYAKKFHGRLIISADEFTTTFYMELTSLTFDDTAIYYCARSGSTESPIQHIDFWGQGTLVT VSS | 71 |
| STAU-307 light | SYVLTQPPSVSVAPGQTATITCGGDNIATFSVHWYRQKPGQAPVLVVYDDLDRASGIPA RFSGSNSGNTATLTISRVEPGDEADYFCQVWEISSDEYVFGPGTSVTVL | 72 |
| STAU-328 heavy | QVQLQQWGAGLLKPSETLSLTCAVYGGSFSGYYWSWIRQPPGKGLEWIGElNHSGSTNY NPSLKSRVTISVDTSKNQFSLKLSSVTAADTAVYYCARDVGDRYYFDYWGQGTLVTVSS | 73 |
| STAU-328 light | QSALTQPASVSGSPGQSITISCTGTSSDVGSYNLVSWYQQHPGKAPKLMIYEGSKRPSGV SNRFSGSKSGNTASLTISGLQAEDEADYYCCSYAGSSTFVVFGGGTKLTVL | 74 |
| STAU-389 heavy | QVQLVQSGAEVKQSGSSLKVSCKVSGGNLRSYGISWVRQAPGQGLEWMGVIIPIFGAPT YAQKFQGRVTFVADDGNNVVFMELSSLRSEDTAVYYCARDWPSITVAVDAINFAMDV WGQGTLVTVSS | 75 |
| STAU-389 light | QSALTQPRSVSGSPGQSVTISCTGTNNDVGSYDHVSWYQQHPGKAPKFIIYDVSTRPSGV PDRFSGSKSDNTASLTISGLQAEDEADYYCCSFAGSYTYVFGTGTTVTVL | 76 |
| STAU-399 heavy | QVQLVQSGAEVKKPGSSLKVSCKVSGGNLRSYGISWVRQAPGQGLEWMGVIIPIFGTPT YAQKFQGRVTLAADDSNNIVFMELSSLRSEDTAVYYCARDWPSITVAVDATNYGMDVW GQGTLVTVSS | 77 |
| STAU-399 light | QSALTQPRSVSGSPGQSVTISCTGTSNDVGYYDHVSWYQQHPGKAPKFIIYDVSKRPSGV PDRFSGSKSDNTASLTISGLQAEDEADYYCCSFAGSYTYVFGTGTKVTVL | 78 |

TABLE 2-continued

PROTEIN SEQUENCES FOR ANTIBODY VARIABLE REGIONS

| Clone | Variable Sequence | SEQ ID NO. |
|---|---|---|
| STAU-401 heavy | QVQLVQSGPEARKPGTSVKVSCKTSGYTFSSYGIAWVRQAPGQGLEWMGWISGYSDYT IYAQRLQGRVSMTTDPYTSTAYMELRSLRPDDTAVYYCATLSFGELVENKLDFWGQGTLV TVSS | 79 |
| STAU-401 light | QSVLTQPPSVSGAPGQRVTISCTGTSSNIGADYAVHWYQQLPGTAPKLLIYGTINRPSGV PDRFSGSRSGTSASLAITGLQADDEADYYCQSYDSSLSGSVVFGGGTKLTVL | 80 |
| STAU-402 heavy | QLQLQESGPGLVKPSETLSLTCTVSGGSISSSSYYWGWIRQPPGKGLEWIGSIYYSGSTYY NPSLKSRVTISVDTSKNQFSLKLSSVTAADTAVYYCARPNSSGWSYYFDYWGQGTLVTVSS | 81 |
| STAU-402 light | QSVLTQPPSVSGAPGQRVTISCTGTSSNIGADYDVHWYQQLPGTAPKLLIYGNINRPSGV PDRFSGSRSGTSASLAITGLQADDEADYYCQSYDSSLSGSVVFGGGTKLTVL | 82 |
| STAU-407 heavy | QLQLQESGPGLVKPSETLSLTCSVSGGSISRTYYYWDWIRQPPGKGLEWIGSVYYSGSTYY NPSLKSRVTMSVDTSKNLFSLKLSSVTAADTAVYYCASHESWQQLISWGQGTLVTVSS | 83 |
| STAU-407 light | QAVLTQPSSLSASPGASASLTCTLRSGINVGIYRIYWYQQKPGSPPQYLLRYKSDSDKHQG SGVPSRFSGSKDASANAGILLISGLQSEDEADYYCMIWHSSAVAFGGGTKLTVL | 84 |

TABLE 3

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| STAU-37 | GFTFSDYY (85) | ISSSGSTI (86) | ARETPRRITGMGLEDYYYGMDV (87) |
| STAU-64 | GFSFSYYS (88) | ISSSGEYI (89) | AKVVSQQSLDY (90) |
| STAU-75 | GGSISSVSYY (91) | IFYSGST (92) | ARQIYYYELEEFDY (93) |
| STAU-138 | Not available (94) | Not available (95) | Not available (96) |
| STAU-139 | GYSFTSYW (97) | IYPGDSDT (98) | ARPPGLRGDAFDI (99) |
| STAU-147 | KHMFSNYW (100) | IYPPDADT (101) | ATTGGSGTYLDYFDY (102) |
| STAU-201 | GYTFTNYG (103) | ISPYTGRA (104) | AREGIKDASAFDF (105) |
| STAU-218 | DVSLRNVQMG (106) | IFSHDEK (107) | ARIRSTSGEEEDPFAF (108) |
| STAU-221 | GFSLTSSGMC (109) | IDWDDDK (110) | ARTQSGYSGYYVDY (111) |
| STAU-229 | GYPFTDYY (112) | IDPEDGET (113) | AKPHCSSRTCQRVSGYYFGMDV (114) |
| STAU-239 | GGPFNTYV (115) | IVPVFNTS (116) | ARDGAAAPLNWYDP (117) |
| STAU-280 | GFTFSRYN (118) | ISATSSSI (119) | VREDAAIFGVGSWFDP (120) |
| STAU-281 | GDSFRRYV (121) | IIPIFDKA (122) | ARKEDGRRDDVFDI (123) |
| STAU-299 | GFSLSTSGMC (124) | IDWEDDK (125) | ARTPTYRGAFDM (126) |
| STAU-307 | GATFNTND (127) | IVPVFGRP (128) | ARSGSTESPIQHIDF (129) |

TABLE 3-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| STAU-328 | GGSFSGYY (130) | INHSGST (131) | ARDVGDRYYFDY (132) |
| STAU-389 | GGNLRSYG (133) | IIPIFGAP (134) | ARDWPSITVAVDAINFAMDV (135) |
| STAU-399 | GGNLRSYG (136) | IIPIFGTP (137) | ARDWPSITVAVDATNYGMDV (138) |
| STAU-401 | GYTFSSYG (139) | ISGYSDYT (140) | ATLSFGELVENKLDF (141) |
| STAU-402 | GGSISSSSYY (142) | IYYSGST (143) | ARPNSSGWSYYFDY (144) |
| STAU-407 | GGSISRTYYY (145) | VYYSGST (146) | ASHESWQQLIS (147) |

TABLE 4

CDR LIGHT CHAIN SEQUENCES

| Antibody | CDRH1 (SEQ ID NO:) | CDRH2 (SEQ ID NO:) | CDRH3 (SEQ ID NO:) |
|---|---|---|---|
| STAU-37 | Not available (148) | Not available (149) | Not available (150) |
| STAU-64 | QSISTY (151) | GGS (152) | QQSYSTRYS (153) |
| STAU-75 | Not available (154) | Not available (155) | Not available (156) |
| STAU-138 | SSNIGNNY (157) | DNN (158) | GTWDSSLSAGV (159) |
| STAU-139 | SSDVGGYNY (160) | EVS (161) | SSYAGSNNLV (162) |
| STAU-147 | Not available (163) | Not available (164) | Not available (165) |
| STAU-201 | GSDIGGYNH (166) | GVT (167) | SSYTDNTSWV (168) |
| STAU-218 | QSVTTW (169) | SAS (170) | QQYRFYWT (171) |
| STAU-221 | SSNIGSNT (172) | SND (173) | SAWDDSLNGRYV (174) |
| STAU-229 | SNDVGDYNF (175) | EVT (176) | SSYAGGNSVV (177) |
| STAU-239 | NIGSKS (178) | DVR (179) | QVWESTTSHVI (180) |
| STAU-280 | QSVSSN (181) | GAS (182) | QEYNDWPLYT (183) |
| STAU-281 | HSVGSS (184) | GVS (185) | QQYDNWPFT (186) |
| STAU-299 | TSNIGSNT (187) | NNN (188) | AAWDDSLNGVV (189) |
| STAU-307 | NIATFS (190) | DDL (191) | QVWEISSDEYV (192) |
| STAU-328 | SSDVGSYNL (193) | EGS (194) | CSYAGSSTFVV (195) |
| STAU-389 | NNDVGSYDH (196) | DVS (197) | CSFAGSYTYV (198) |
| STAU-399 | SNDVGYYDH (199) | DVS (200) | CSFAGSYTYV (201) |
| STAU-401 | SSNIGADYA (202) | GTI (203) | QSYDSSLSGSVV (204) |
| STAU-402 | SSNIGADYD (205) | GNI (206) | QSYDSSLSGSVV (207) |
| STAU-407 | SGINVGIYR (208) | YKSDSDK (209) | MIWHSSAVA (210) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, NY, 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Barzon et al., *Euro Surveill.* 2016 Aug. 11; 21(32).
Beltramello et al., *Cell Host Microbe* 8, 271-283, 2010.
Brown et al., *J Immunol. Meth.*, 12; 130(1), 111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
De Jager et al., *Semin. Nucl. Med.* 23(2), 165-179, 1993.
Dholakia et al., *J. Biol. Chem.*, 264, 20638-20642, 1989.
Diamond et al., *J Virol* 77, 2578-2586, 2003.
Doolittle and Ben-Zeev, *Methods Mol. Biol.*, 109, 215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.*, 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Persic et al., *Gene* 187:1, 1997
Potter and Haley, *Meth. Enzymol.*, 91, 613-633, 1983.
Purpura et al., *Lancet Infect Dis.* 2016 October; 16(10): 1107-8. Epub 2016 Sep. 19.
Remington's Pharmaceutical Sciences, 15th Ed., 3:624-652, 1990.
Tang et al., *J. Biol. Chem.*, 271: 28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., *J Immunol Methods* 336, 142-151, doi:10.1016/j.jim.2008.04.008,2008.
Hood and Skaar. 2012. Nat Rev Microbiol 10:525-537.
Skaar E P. 2010. PLoS Pathog 6:e1000949.
Skaar et al., 2004. Science 305:1626-1628.
Mazmanian et al., 2003. Science 299:906-909.
Grigg et al., 2007. Molecular Microbiology 63:139-149.
Grigg et al., 2010. Journal of Inorganic Biochemistry 104: 341-348.
Skaar and Schneewind, 2004. Microbes and Infection 6:390-397.
Torres et al., 2006. Journal of Bacteriology 188:8421-8429.
Muryoi et al., 2008. J Biol Chem 283:28125-28136.
Liu et al., 2008. J Biol Chem 283:6668-6676.
Pilpa et al., 2006. J Mol Biol 360:435-447.
Foster et al., 2013. Nat Rev Microbiol 12:49-62.
Choby and Skaar. 2016. J Mol Biol 428:3408-3428.
Pishchany et al., 2009. Infect Immun 77:2624-2634.
Kuklin et al., 2006. Infect Immun 74:2215-2223.
Kim et al., 2010. Vaccine 28:6382-6392.
Pishchany et al., 2014. J Infect Dis 209:1764-1772.
Pishchany et al., 2010. Cell Host Microbe 8:544-550.
Nimmerjahn and Ravetch. 2007. Fc-Receptors as Regulators of Immunity, pp. 179-204. In. Elsevier.
Pishchany et al., 2013. J Vis Exp., 72:50072.
Brown et al., 2009. Clin Vaccine Immunol 16:1095-1104.
Pancari et al., 2012. Front Cell Infect Microbiol 2:36.
Ebert et al., 2010. Hum Antibodies 19:113-128.
Harro et al., 2010. Clin Vaccine Immunol 17:1868-1874.
Moustafa et al., 2012. Clin Vaccine Immunol 19:1509-1516.
Vu et al., 2016. PROTEOMICS 16:2667-2677.
Diep et al., 2014. J Infect Dis 209:1533-1541.
Verkaik et al., 2010. Eur J Clin Microbiol Infect Dis 29:509-518.
Ghasemzadeh-Moghaddam et al., 2017. Eur J Clin Microbiol Infect Dis 17:1-9.
Ebert et al., 2010. Hum Antibodies 19:113-128.
Pishchany et al., 2014. J Infect Dis 209:1764-1772.
Petit and Read. 2018. Peer J 6:e5261.
Wines et al., 2000. Immunol BWJ 164:5313-8.
Hezareh et al., 2001. J Virol 75:12161-12168.
Hessell et al., 2007. Nature 449:101-104.
Rouha et al., 2015. mAbs 7:243-254.
O'Riordan and Lee. 2004. Clinical Microbiology Reviews 17:218-234.
Joshi et al., 2014. Hum Vaccin Immunother 8:336-346.
Stranger-Jones et al., 2006. Proc Natl Acad Sci USA 103: 16942-16947.
Clarke et al., 2006. J Infect Dis 193:1098-1108.
Verkaik et al., 2010. Clin Microbiol Infect 16:1312-1317.
Reijer et al., 2016. PLoS ONE 11:e0145722.
Stapleton et al., 2012. Journal of Medical Microbiology 61:766-779.
Balderas et al., 2016. Infect Immun 84:3408-3422.
Mazmanian et al., 2002. Proc Natl Acad Sci USA 99:2293-2298.
Camacho et al., 2009. BMC Bioinformatics 10:421.
Li and Godzik. 2006. Bioinformatics 22:1658-1659.
Fu et al., 2012. Bioinformatics 28:3150-3152.

What is claimed is:

1. A method of treating a subject infected with *S. aureus*, or reducing the likelihood of infection of a subject at risk of contracting *S. aureus*, comprising delivering to said subject an antibody or antibody fragment having heavy chain CDR1-3 sequences of SEQ ID NOS: 115, 116, and 117 and light chain CDR1-3 sequences of SEQ ID NOS: 178, 179 and 180.

2. The method of claim 1, the antibody or antibody fragment is encoded by a heavy chain variable coding region comprising SEQ ID NO: 21 and a light chain variable coding region comprising SEQ ID NO: 22.

3. The method of claim 1, the antibody or antibody fragment is encoded by a heavy chain variable region sequence having 95% identity to SEQ ID NO: 21 and a light chain variable region sequence having 95% identity to SEQ ID NO: 22, but retaining coding sequences for heavy chain CDR1-3 sequences of SEQ ID NOS: 115, 116, and 117 and for light chain CDR1-3 sequences of SEQ ID NOS: 178, 179 and 180.

4. The method of claim 1, wherein said antibody or antibody fragment is encoded by a heavy chain variable region sequence having 70%, 80%, or 90% identity to SEQ ID NO: 21 and a light chain variable region sequence having 70%, 80%, or 90% identity to SEQ ID NO: 22, but retaining coding sequences for heavy chain CDR1-3 sequences of SEQ ID NOS: 115, 116, and 117 and for light chain CDR1-3 sequences of SEQ ID NOS: 178, 179 and 180.

5. The method of claim 1, wherein said antibody or antibody fragment comprises a heavy chain variable sequence comprising SEQ ID NO: 63 and a light chain variable chain sequence comprising SEQ ID NO: 64.

6. The method of claim 1, wherein said antibody or antibody fragment comprises a heavy chain variable region sequence having 70%, 80% or 90% identity to SEQ ID NO: 63 and a light chain variable region sequence having 70%, 80% or 90% identity to SEQ ID NO: 64, but retaining the heavy chain CDR1-3 sequences of SEQ ID NOS: 115, 116, and 117 and the light chain CDR1-3 sequences of SEQ ID NOS: 178, 179 and 180.

7. The method of claim 1, wherein said antibody or antibody fragment comprises a heavy chain variable region sequence having 95% identity to SEQ ID NO: 63 and a light chain variable region sequence having 95% identity to SEQ ID NO: 64, but retaining the heavy chain CDR1-3 sequences of SEQ ID NOS: 115, 116, and 117 and the light chain CDR1-3 sequences of SEQ ID NOS: 178, 179 and 180.

8. The method of claim 1, wherein the antibody fragment is a recombinant scFv (single chain fragment variable) antibody, Fab fragment, F(ab')$_2$ fragment, or Fv fragment.

9. The method of claim 1, wherein said antibody is an IgG, or a recombinant IgG antibody or antibody fragment comprising an Fc portion mutated to alter FcR interactions, to increase half-life and/or increase therapeutic efficacy, or glycan modified to alter FcR interactions.

10. The method of claim 1, wherein said antibody is a chimeric antibody or a bispecific antibody.

11. The method of claim 1, wherein said antibody or antibody fragment is administered prior to infection or after infection.

12. The method of claim 1, wherein said subject is a pregnant female, a sexually active female, or a female undergoing fertility treatments.

13. The method of claim 1, wherein delivering comprises antibody or antibody fragment administration, or genetic delivery with an RNA or DNA sequence or vector encoding the antibody or antibody fragment.

14. The method of claim 1, further comprising treating said subject with a second anti-Isd antigen antibody.

15. The method of claim 14, wherein the second antibody recognizes IsdB.

16. The method of claim 9, wherein the mutation to increase half-life and/or increase therapeutic efficacy is a LALA, N297, GASD/ALIE, YTE or LS mutation.

17. The method of claim 9, wherein the glycan modification to alter FcR interactions is as enzymatic or chemical addition or removal of glycans or expression in a cell line engineered with a defined glycosylating pattern.

18. The method of claim 14, wherein the second antibody recognizes IsdH.

* * * * *

SEQUENCE LISTING

<160> NUMBER OF SEQ ID NOS: 213

<210> SEQ ID NO 1
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 1

```
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtagtac catatactac   180
gcagactctg tgaagggccg attcaccatc tccaggaca acgccaagaa ctcactgtat    240
ctgcaaatga acagcctgag agccgaggac acggctgtgt attactgtgc gagagagacc   300
ccccgacgta taactggaat gggcttgag gactactact acggtatgga cgtctggggc   360
caagggaccc tggtcaccgt ctcctca                                        387
```

<210> SEQ ID NO 2

<400> SEQUENCE: 2

000

<210> SEQ ID NO 3
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 3

```
gaggtgcagc tggtggagtc tgggggaggc ctggtcaagc cggggggtc cctgagactc     60
tcctgtgcag cctctggatt cagcttcagt tactatagca tgaattgggt ccgccaggct   120
ccagggaagg ggctggagtg gatctcatcg attagtagta gtggtgaata catatattac   180
gcagattcag tgaagggccg attcaccatc tccagagaca acgccgagaa ctcactgtat   240
ctgcaaatga acagcctgag agccgaggac acggctgtgt attactgtgc gaaagtggtt   300
tctcagcagt cccttgatta ctggggccag ggaaccctgg tcaccgtctc ctca         354
```

<210> SEQ ID NO 4
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 4

```
gacatcgtga tgacccagtc tccatcctcc ctgtctgtat ctgttggaga cagagtcacc    60
atcacttgcc gggcaagtca gagcattagt acctatttaa actggtatca gcagaaacca   120
gggaaagccc ctaagctcct gatctctggt ggatccaatt tgcaaagtgg ggtcccatca   180
aggttcagtg gcagtggatc tgggacagat ttcactctca ccatcatcag tctccaacct   240
gaagattttg caacttacta ctgtcaacag agttacagta cccggtacag ttttggccag   300
gggaccaagc tggagatcaa a                                              321
```

<210> SEQ ID NO 5

<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 5

```
cagctgcagc tgcaggagtc gggcccagga ctggtgaagc cttcggagac cctgtccctc      60
acctgcactg tctctggtgg ctccatcagc agtgtttctt actactgggg ctggatccgc     120
cagcccccag ggaaggggct ggagtgggtt gcgtccatat tttatagtgg gagcacaaag     180
tacaacccgt ccctcgagag tcgagtcacc atatcagtag acacgtccaa gaaccagttc     240
ttcctgaagc tgacctctgt gaccgccgca gacacggctg tatattactg tgcgagacaa     300
atatattact acgaacttga agaatttgac tactggggcc agggaaccct ggtcaccgtc     360
tcctca                                                                366
```

<210> SEQ ID NO 6

<400> SEQUENCE: 6

000

<210> SEQ ID NO 7

<400> SEQUENCE: 7

000

<210> SEQ ID NO 8
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 8

```
cagtctgtgt tgacgcagcc gccctcagtg tctgcggccc caggacagaa ggtcaccatc      60
tcctgctctg gaagcagctc aacattggga ataattatg tatcctggta ccagcagctc     120
ccaggaacag cccccaaact cctcatttat gacaataata gcgaccctc agggattcct     180
gaccgattct ctggctccaa gtctggcacg tcagccaccc tgggcatcac cggactccag     240
actggggacg aggccgatta ttactgcgga acatgggata gcagcctgag tgctggggta     300
ttcggcggag ggaccaagct gaccgtccta                                      330
```

<210> SEQ ID NO 9
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 9

```
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac     240
ctgcagtgga gcagcctgaa ggcctcggac accgccatgt attactgtgc gagaccgccg     300
ggactacgcg gagatgcttt tgatatctgg ggccaaggga ccctggtcac cgtctcctca     360
```

<210> SEQ ID NO 10
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 10

```
cagtctgccc tgactcagcc tccctccgcg tccgggtctc ctggacagtc agtcaccatc    60
tcctgcactg gaaccagcag tgacgttggt ggttataact atgtctcctg gtaccaacag   120
cacccaggca agcccccaa actcatgatt tatgaggtca gtaagcggcc ctcaggggtc    180
cctgatcgct tctctggctc caagtctggc aacacggcct ccctgaccgt ctctgggctc   240
caggctgagg atgaggctga ttattactgc agctcatatg caggcagcaa caatttggtg   300
ttcggcggag ggaccaagct gaccgtccta                                    330
```

<210> SEQ ID NO 11
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 11

```
gaggtgcagc tggtgcagtc tggaacagag gtgaaaaagc ccggggagtc tctgaggatc    60
tcctgtacgg gttctaaaca catgttttcc aattactgga tcgcctgggt gcgccagagg   120
cccgggaaag gcctggagtg gatggggatc atctaccctc ctgacgctga taccagatac   180
agcccgtcct tcaaaggcca ggtcaccatc tcagccgaca aggccaccaa caccgcctac   240
ctgcagtgga gcagcctgag ggcctcggac accgccatgt attactgtgc taccacggga   300
ggatcaggaa cctatttaga ttactttgac tactggggcc agggaaccct ggtcaccgtc   360
tcctca                                                              366
```

<210> SEQ ID NO 12

<400> SEQUENCE: 12

000

<210> SEQ ID NO 13
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 13

```
caggttcagc tggtgcagtc tggacctgag gtgaagaagc ctggggcctc agtgaaggtc    60
tcctgcaagg cttctggtta cacctttacc aactatggtc tcacctgggt gcgacaggcc   120
cctggaaaag gacttgagtg gattggatgg atcagccctt acactgggcg cgcaaagttt   180
gccctgaagt ccagggcag attcaccttg accacagaca catccacgac acagcctac    240 atggaggtga ggagcctgaa atctgacgac tcggccgtgt attactgcgc gagggaaggg   300
attaaagatg ctagtgcttt tgacttctgg ggccagggaa ccctggtcac cgtctcctca   360
```

<210> SEQ ID NO 14
<211> LENGTH: 330

<212> TYPE: DNA
<213> ORGANISM: Artificial sequence
<220> FEATURE:
<223> OTHER INFORMATION: Synthetic oligonucleotide

<400> SEQUENCE: 14

```
cagtctgccc tgactcagcc tgcctccgtg tctgggtctc ctggacagtc gatcaccatc    60
tcctgcactg gaaccggcag tgacattggt ggttataacc atgtctcctg gtaccaccat   120
tacccaggca aagcccccaa actcttgatt tttggggtca ctcatcgtcc ctcaggtgtt   180
tctgatcgct tctctggctc caagtctggc gtcacggcct tcctgaccat ctctgggctc   240
caggctgagg acgaggctga ttattactgc agctcatata cagacaacac ttcttgggtg   300
tttggcgggg ggaccaaggt gaccgtccta                                    330
```

<210> SEQ ID NO 15
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 15

```
caggtcacct tgaaggagtc tggtcctgta gtggtgaaac ccacagagac cctcacgctg    60
acctgcaccg tctctgacgt ctcactccgc aatgttcaaa tgggtgtgag ctggatccgc   120
cagcccccag ggaaggccct ggagtggctt gcacacatct tttcgcatga cgaaaaggcc   180
tacgttacat ctctggagaa ccggctcacc atctccaggg acacctccaa cagtcaggtg   240
gtcctgacca tgacgaacat ggaccctgtg acacaggca catattactg tgcacggata    300
cgttctactt cagggaaga ggaggatcct tttgctttct ggggccaggg gaccctggtc   360
accgtctcct ca                                                       372
```

<210> SEQ ID NO 16
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 16

```
gacatccaga tgacccagtc tccttcctcc ctgtctgcat ctgttggaga cagggtcacc    60
atcacttgcc gggccagtca gagtgtcact acctggttgg cctggtatca gcagaaacca   120
gggaaagccc ctaaactcct aatctatagt gcctcaagtt tggaaagtgg ggtcccatca   180
aggttcagcg gcagtggatc tgggacagac ttcactctca ccatcagtaa cctgcagcct   240
gatgactttg caacttatta ctgccaacag tatcgttttt attggacgtt cggccaaggg   300
accaaggtgg aaagcaag                                                 318
```

<210> SEQ ID NO 17
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 17

```
caggtcacct tgagggagtc tggtcctgcg ctggtgaaac ccacacagac cctcacactg    60
acctgcacct tctctgggtt ctcacttacc agtagtggaa tgtgtgtgtc ctggatccgt   120
```

| | |
|---|---|
| cagcccccag ggaaggccct ggagtggctt gcactcattg attgggatga tgataaatac | 180 |
| tacatcacat ctctaaagac caggctcatc atctccaagg acacctccaa aaaccaggtg | 240 |
| gtccttacaa tgaccaacat ggaccctgtg acacagcca cgtattactg tgcacggacg | 300 |
| caaagtggat atagtggcta ctacgttgac tactggggcc agggaaccct ggtcaccgtc | 360 |
| tcctca | 366 |

<210> SEQ ID NO 18
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 18

| | |
|---|---|
| cagtctgtgc tgactcagcc accctcagcg tctgggaccc ccgggcagaa ggtcaccatc | 60 |
| tcttgttctg gaagcagctc caacatcgga agtaatactg taaactggta ccagcagctc | 120 |
| ccaggaacgg cccccaaact cctcatctat agtaatgata gcggccctc aggggtccct | 180 |
| gaccgattct ctggctccaa gtctggcacc tcagcctccc tggccatcag tgggctccag | 240 |
| tctgaggatg aggctgatta ttactgttca gcgtgggatg acagcctgaa tggtcgttat | 300 |
| gtcttcggaa ctgggaccaa ggtcaccgtc cta | 333 |

<210> SEQ ID NO 19
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 19

| | |
|---|---|
| gaggtccagc tggtacagtc tggggctgag gtgaagaagc ctggggctac aatgaaaatc | 60 |
| tcctgcaagg tttctggata ccccttcacc gactactaca tgcactgggt gcaacaggcc | 120 |
| cctggaaaag ggcttgagtg gatgggactt attgatcctg aagatggtga acaaaactac | 180 |
| gcagagaagt tccagggcag agtcaccata accgcggaca cgtctacaga cacagtctac | 240 |
| atggaactga gcagcctgag atctgaggac acggccgtct atttctgtgc aaaaccacac | 300 |
| tgtagtagta ggacctgcca gcgggtgtcg gggtactact cggtatgga cgtctggggc | 360 |
| caagggaccc tggtcaccgt ctcctca | 387 |

<210> SEQ ID NO 20
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 20

| | |
|---|---|
| cagtctgccc tgactcagcc tcctccgcg tccgggtctc ctggacagtc agtcaccatc | 60 |
| tcctgcactg gaagcagcaa tgacgttggt gattataact tgtctcgtg gtaccaacaa | 120 |
| cacccaggca aacccccaa actcatgatt tatgaggtca ctaagcggcc ctcagggtc | 180 |
| cctgatcgct tctttggctc caagtctggc aacacggcct ccctgaccgt ctctgggctc | 240 |
| caggctgacg atgaggctga ttattattgc agctcatatg caggcggcaa ctctgtggta | 300 |
| ttcggcggtg ggaccaagct taccgtccta | 330 |

```
<210> SEQ ID NO 21
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 21
caggtgcagc tggtgcagtc tggggctgag gtgaagaagc ctgggtcttc ggtgaaggtc      60
tcctgcaggg cctctggagg ccccttcaac acctatgtta tcacctgggt gcgacaggcc     120
cctggacaag gtcttgagtg gatgggggga atcgtccctg tctttaatac atcacactcc     180
gcacagaagt tccagggcag agtcaagatt ccgcggaca catccaccaa cactgtctac     240
atggaattga ccagcctaac atttgaggac acggccgtat acttttgcgc gcgagatggc     300
gccgcagctc ccctgaattg gtacgacccc tggggccagg gaaccctggt caccgtctcc     360
tca                                                                    363

<210> SEQ ID NO 22
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 22
tcctatgtgc tgactcagcc accctcggtg tcgctggccc cagggcagac ggccacgctt      60
acctgtgggg gaaacaatat tggcagtaaa agtgtacact ggtaccagaa gaagccaggc     120
caggcccctg tgctggtcgt ctatgatgtc agggaccggc cctctgggat ccccgagcga     180
ttctctggct ccagctctga gaacacggcc accctgaccc tcagcagggt cgaagccgag     240
gatgaggccg actattactg tcaggtgtgg gaaagtacta cttctcatgt gatattcggc     300
ggagggacca agctgaccgt ccta                                            324

<210> SEQ ID NO 23
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 23
gaggtgcagc tggtggagtc ggggggaggc ttggtacaga ctggagggtc cctgagactc      60
tcctgtgcag cctctggatt caccttagt agatataaca tgaattgggt ccgccaggct     120
ccagggaagg gactggagtg ggtttccttc attagtgcta ctagtagtag catatactac     180
gcagactctg tgaagggccg attcaccatc tccagagaca tgccaagaa ctcactggat     240 ctgcaaatga acagcctgag agacgaggac acggctgtat atttctgtgt gagagaggat     300
gctgcgattt ttggagtggg gagttggttc gaccccctggg gccagggaac cctggtcacc     360
gtctcctca                                                              369

<210> SEQ ID NO 24
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 24
```

```
gaaattgtga tgactcagtc tccagccacc ctgtctgtgt ctccagggga aagagccacc    60
ctctcctgca gggccagtca gagtgttagt agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttattt ctgtcaggag tataatgact ggcccctgta cacttttggc   300
caggggacca agctggagat caaa                                          324
```

<210> SEQ ID NO 25
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 25

```
caggtgcagc tggtgcagtc tggggctgaa gtgaagaggc cagggtcctc ggtgagggtc    60
tcctgcaagg actctggaga cagcttcaga agatatgtta tcaattgggt gcgacaggcc   120
cctggacaag gcttgagtg gatgggaggg atcatcccta tctttgacaa agcaaagtcc    180
gtccagaaat tccaggacag actcaccatt accgcgacg aatctacgag cacatcgtac    240
atggagttga gcagtctgac atctgaagac acggccgtgt attactgtgc gagaaaagaa   300
gatggacgta gagatgatgt ttttgatatc tggggccaag gaccctggt caccgtctcc    360 tca                                                                363
```

<210> SEQ ID NO 26
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 26

```
gaaatagtga tgacgcagtc tccagccacc ctgtctgtgt ctctgggaga aagagccacc    60
ctctcctgca gggccagtca cagtgttggc agcagcttgg cctggtatca gcagaaacct   120
ggcctggctc ccaggctcct catctatggt gtctccacca gggccactgg tatcccagcc   180
aggttcagtg gcagtgggtc tgcgacagag ttcactctca ccatcagcag cctgcagtct   240
gaggatttag cagcttatca ctgtcagcag tatgataact ggccattcac atttggccag   300
gggaccaagc tggagatcaa a                                            321
```

<210> SEQ ID NO 27
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 27

```
caggtcacct tgagggagtc tggtcctgcg ctggtgaagc ccacagagac cgtcacactg    60
acctgcacct tctctgggtt ctcactcagc actagtggaa tgtgtgtgac ctggctccgt   120 cagccccag ggaaggccct ggagtggctt gcactcattg attgggagga tgataaatac    180
tacagcacat ctctgaagac caggttcacc atctccaagg acacctccaa aaaccaggtg   240
gtccttacaa tgaccaacat ggaccctgtg gacagagcca cgtattactg tgcacggacc   300
ccaacgtatc gcggggcttt tgatatgtgg ggccaaggga ccctggtcac cgtctcctca   360
```

<210> SEQ ID NO 28
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 28

```
cagtctgtgc tgactcagcc accctcagcg tctgggaccc ccgggcagag ggtcaccatc      60
tcttgttctg gaagcacctc caacatcgga agtaatactg taaactggta ccagcagctc    120
ccaggaacgg ccccccaact cctcatctat aataataatc agcggccctc aggggtccct    180
gaccgattct ctggctccaa gcctggcacc tcagcctccc tggccatcag tgggctccag    240
tctgaggatg aggctgatta ttactgcgca gcatgggatg acagcctgaa tggtgtggta    300
ttcggcggag ggaccaagct gaccgtccta                                      330
```

<210> SEQ ID NO 29
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 29

```
caggtgcagc tggtgcagtc tggggctgag gttaagaaga ctgggtcctc ggtgaaggtc      60
tcatgcacgg cttcaggagc caccttcaac accaatgatc tcatgtgggt gcgacaggcc    120
cctggacaag gacttgagtg gatgggggggg atcgtcccag tttttggaag accgaaatac    180
gcaaagaagt tccatggcag actcatcata agtgcggacg aattcacaac caccttctac    240
atggaactga ccagcctgac attcgacgac acggccatat attattgcgc gagaagtggc    300
agtacagaat cacccattca gcatattgac ttttggggcc agggaaccct ggtcaccgtc    360
tcctca                                                                366
```

<210> SEQ ID NO 30
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 30

```
tcctatgtgc tgactcagcc accctcggtg tcagtggccc caggacagac ggccacgatt      60
acctgtgggg gagacaacat tgcgactttc agtgtgcact ggtaccggca gaagccaggc    120
caggcccctg tgttggtcgt ctatgatgat ctcgaccggg cctcagggat ccctgcgcga    180
ttctccggct ccaattctgg gaacacggcc accctgacaa tcagcagagt cgagcccggg    240
gatgaggccg actatttctg tcaggtgtgg gaaatttcta gtgacgaata tgtcttcgga    300
cctgggacca gtgtcaccgt cctc                                            324
```

<210> SEQ ID NO 31
<211> LENGTH: 354
<212> TYPE: DNA
<213> ORGANISM: Artificial sequence
<220> FEATURE:
<223> OTHER INFORMATION: Synthetic oligonucleotide

<400> SEQUENCE: 31

| | |
|---|---|
| caggtgcagc tacagcagtg gggcgcagga ctgttgaagc cttcggagac cctgtccctc | 60 |
| acctgcgctg tctatggtgg gtccttcagt ggttactact ggagctggat ccgccagccc | 120 |
| ccagggaagg ggctggagtg gattggggaa atcaatcata gtggaagcac caactacaac | 180 |
| ccgtccctca agagtcgagt caccatatca gtagacacgt ccaagaacca gttctccctg | 240 |
| aagctgagct ctgtgaccgc cgcggacacg gctgtgtatt actgtgcgag agatgtcggt | 300 |
| gaccggtact actttgacta ctggggccag ggaaccctgg tcaccgtctc ctca | 354 |

<210> SEQ ID NO 32
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 32

| | |
|---|---|
| cagtctgccc tgactcagcc tgcctccgtg tctgggtctc ctggacagtc gatcaccatc | 60 |
| tcctgcactg gaaccagcag tgatgttggg agttataacc ttgtctcctg gtaccaacag | 120 |
| cacccaggca aagcccccaa actcatgatt tatgagggca gtaagcggcc ctcaggggtt | 180 |
| tctaatcgct tctctggctc caagtctggc aacacggcct ccctgacaat ctctgggctc | 240 |
| caggctgagg acgaggctga ttattactgc tgctcatatg caggtagtag cacttttgtg | 300 |
| gtattcggcg gagggaccaa gctgaccgtc cta | 333 |

<210> SEQ ID NO 33
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 33

| | |
|---|---|
| caggtgcagc tggtgcagtc tggggctgag gtaaagcagt ctgggtcctc gctgaaggtc | 60 |
| tcctgtaagg tttctggagg caatttacgg agttatggta tcagttgggt gcgacaggcc | 120 |
| cctggacagg ggcttgagtg gatgggagtg atcatcccta tctttggagc accaacctac | 180 |
| gcacagaagt tccagggcag agttacattt gtcgcggacg atggcaacaa tgtagtcttc | 240 |
| atggagctga gtagtctgag atctgaggac acggccgtgt attactgtgc gagagattgg | 300 |
| ccctcaatta cagtggcggt cgatgctatc aatttcgcaa tggacgtctg gggccaaggg | 360 |
| accctggtca ccgtctcctc a | 381 |

<210> SEQ ID NO 34
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 34

| | |
|---|---|
| cagtctgccc tgactcagcc tcgctcagtg tccgggtctc ctggacagtc agtcaccata | 60 |
| tcctgcaccg gaaccaacaa tgacgttgga tcttatgacc atgtctcctg gtaccagcag | 120 |
| cacccgggca aagcccccaa attcataatt tatgatgtct ctacgcggcc gtcaggggtc | 180 |
| cctgatcgct tctctggctc caagtctgac aacacggcct ccctgaccat ctctgggctc | 240 |
| caggctgagg atgaggctga ttattactgc tgctcatttg cgggcagcta cacttatgtc | 300 |
| ttcggaactg ggacgacggt caccgtcctc | 330 |

<210> SEQ ID NO 35
<211> LENGTH: 381
<212> TYPE: DNA
<213> ORGANISM: Artificial sequence
<220> FEATURE:
<223> OTHER INFORMATION: Synthetic oligonucleotide

<400> SEQUENCE: 35

| caggtgcagc tggtgcagtc tggggctgag gtaaagaagc ctgggtcctc gctgaaggtc | 60 |
| tcctgtaagg tttctggagg caatttacgg agttatggta tcagttgggt gcgacaggcc | 120 |
| cctggacagg ggcttgagtg gatgggagtg atcatcccta tctttggaac accaacctac | 180 |
| gcacagaagt tccagggcag agtcacactt gccgcggacg attccaacaa tatagtcttc | 240 |
| atggagctga gtagtcttag atctgaggac acggccgtat attactgtgc gagagattgg | 300 |
| ccctccatta cagtggcggt cgatgctacc aattacggaa tggacgtctg gggccaaggg | 360 |
| accctggtca ccgtctcctc a | 381 |

<210> SEQ ID NO 36
<211> LENGTH: 330
<212> TYPE: DNA
<213> ORGANISM: Artificial sequence
<220> FEATURE:
<223> OTHER INFORMATION: Synthetic oligonucleotide

<400> SEQUENCE: 36

| cagtctgccc tgactcagcc tcgctcagtg tccgggtctc ctggacagtc agtcaccata | 60 |
| tcctgcaccg gaaccagcaa tgacgttgga tattatgacc atgtctcctg gtaccagcag | 120 |
| cacccgggca aagcccccaa attcataatt tatgatgtca gtaagcggcc gtcaggggtc | 180 |
| cctgatcgct tctctggctc caagtctgac aacacggcct ccctgaccat ctctgggctc | 240 |
| caggctgagg atgaggctga ttattactgc tgctcatttg caggcagcta cacttatgtc | 300 |
| ttcggaactg ggacgaaggt caccgtcctc | 330 |

<210> SEQ ID NO 37
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 37

| caggttcagc tggtgcagtc tggacctgag gcgaggaagc ctgggacctc agtgaaggtc | 60 |
| tcctgcaaga cgtctggtta caccttagt agctatggca ttgcctgggt gcgacaggcc | 120 |
| cctggacaag ggcttgagtg gatgggatgg atcagcggtt acagtgatta cacaatctat | 180 |
| gcacagaggc tccagggcag agtctccatg accacagacc catatacgag cacagcctac | 240 |
| atggagctga ggagcctgag acctgacgac acggccgtct attactgtgc gaccctgtcg | 300 |
| ttcggggagt tagtggaaaa taaacttgac ttctggggac agggaaccct ggtcaccgtc | 360 |
| tcctca | 366 |

<210> SEQ ID NO 38
<211> LENGTH: 336
<212> TYPE: DNA
<213> ORGANISM: Artificial sequence
<220> FEATURE:
<223> OTHER INFORMATION: Synthetic oligonucleotide

```
<400> SEQUENCE: 38
cagtctgtgc tgacgcagcc gccctcagtg tctggggccc cagggcagag ggtcaccatc      60
tcctgcactg ggaccagctc caatatcggg gctgattatg ctgtccactg gtatcagcag     120
cttccaggaa cagcccccaa actcctcatc tatggtacca tcaatcggcc ctcagggggtc    180 cctgaccgat tctctggctc caggtctggc acgtcagcct ccctggccat cactgggctc     240
caggctgatg atgaggctga ttactactgc cagtcctatg acagcagcct gagcggctct     300
gtggttttcg gtggagggac caagctgacc gtgcta                               336

<210> SEQ ID NO 39
<211> LENGTH: 366
<212> TYPE: DNA
<213> ORGANISM: Artificial sequence
<220> FEATURE:
<223> OTHER INFORMATION: Synthetic oligonucleotide

<400> SEQUENCE: 39
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag gaaggggct ggagtggatt gggagtatct attatagtgg gagcacctac      180
tacaacccgt ccctcaagag tcgagtcacc atatccgtag acacgtccaa gaaccagttc     240
tccctgaagc tgagctctgt gaccgccgca gacacggctg tgtattactg tgcgagaccc     300
aatagcagtg gctggtcgta ctactttgac tactggggcc agggaaccct ggtcaccgtc     360
tcctca                                                                366

<210> SEQ ID NO 40
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 40
cagtctgtgc tgacgcagcc gccctcagtg tctggggccc cagggcagag ggtcaccatc      60
tcctgcactg ggaccagctc caatatcggg gctgattatg atgtccactg gtatcagcag     120
cttccaggaa cagcccccaa actcctcatc tatggtaaca tcaatcggcc ctcagggggtc    180 cctgaccgat tctctggctc caggtctggc acgtcagcct ccctggccat cactgggctc     240
caggctgatg atgaggctga ttactactgc cagtcctatg acagcagcct gagcggctct     300
gtggttttcg gtggagggac caagctgacc gtgcta                               336

<210> SEQ ID NO 41
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 41
cagctgcagc tgcaggagtc gggcccagga ctggtgaagc cctcggagac cctgtccctc      60
acttgcagtg tctctggtgg ctccatcagc aggacgtatt actactggga ctggatccgc     120
cagcccccag gaaggggct ggagtggatt gggagtgtct attatagtgg gagcacctac      180
tacaacccgt ccctcaagag tcgagtcacc atgtccgtag acacgtccaa gaacctgttc     240
tccctgaagc tgagctctgt gaccgccgca gacacggctg tgtattactg tgcgagccat     300
```

```
gagtcatggc agcagctgat ctcctggggc agggaaccc tggtcaccgt ctcctca       357
```

<210> SEQ ID NO 42
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 42

```
caggctgtgc tgactcagcc gtcttccctc tctgcatctc ctggagcatc agccagtctc    60
acctgcacct tacgcagtgg catcaatgtt ggtatctaca ggatatattg gtaccagcag   120
aagccaggga gtcctcccca gtatctcctg aggtacaaat cagactcaga taagcatcag   180
gggtctggag tccccagccg cttctctgga tccaaagatg cttcggccaa tgcagggatt   240
ttactcatct ctggcctcca gtctgaggat gaggctgact attattgtat gatttggcac   300
agcagcgccg tggcattcgg cggagggacc aagctgaccg tccta                   345
```

<210> SEQ ID NO 43
<211> LENGTH: 129
<212> TYPE: PRT
<213> ORGANISM: Artificial sequence
<220> FEATURE:
<223> OTHER INFORMATION: Synthetic amino acid

<400> SEQUENCE: 43

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Pro Arg Arg Ile Thr Gly Met Gly Leu Glu Asp Tyr
            100                 105                 110

Tyr Tyr Gly Met Asp Val Trp Gly Gln Gly Thr Leu Val Thr Val Ser
        115                 120                 125

Ser
```

<210> SEQ ID NO 44

<400> SEQUENCE: 44

000

<210> SEQ ID NO 45
<211> LENGTH: 118
<212> TYPE: PRT
<213> ORGANISM: Artificial sequence
<220> FEATURE:
<223> OTHER INFORMATION: Synthetic amino acid

<400> SEQUENCE: 45

Glu Val Gln Leu Val Glu Ser Gly Gly Gly Leu Val Lys Pro Gly Gly

```
              1               5                  10                 15
Ser Leu Arg Leu Ser Cys Ala Ala Ser Gly Phe Ser Phe Ser Tyr Tyr
                    20                  25                 30

Ser Met Asn Trp Val Arg Gln Ala Pro Gly Lys Gly Leu Glu Trp Ile
                    35                  40                 45

Ser Ser Ile Ser Ser Ser Gly Glu Tyr Ile Tyr Tyr Ala Asp Ser Val
            50                  55                  60

Lys Gly Arg Phe Thr Ile Ser Arg Asp Asn Ala Glu Asn Ser Leu Tyr
65                  70                  75                 80

Leu Gln Met Asn Ser Leu Arg Ala Glu Asp Thr Ala Val Tyr Tyr Cys
                    85                  90                 95

Ala Lys Val Val Ser Gln Gln Ser Leu Asp Tyr Trp Gly Gln Gly Thr
                    100                 105                110

Leu Val Thr Val Ser Ser
            115
```

<210> SEQ ID NO 46
<211> LENGTH: 107
<212> TYPE: PRT
<213> ORGANISM: Artificial sequence
<220> FEATURE:
<223> OTHER INFORMATION: Synthetic amino acid

<400> SEQUENCE: 46

```
              1               5                  10                 15
Asp Ile Val Met Thr Gln Ser Pro Ser Ser Leu Ser Val Ser Val Gly

Asp Arg Val Thr Ile Thr Cys Arg Ala Ser Gln Ser Ile Ser Thr Tyr
                    20                  25                 30

Leu Asn Trp Tyr Gln Gln Lys Pro Gly Lys Ala Pro Lys Leu Leu Ile
                    35                  40                 45

Ser Gly Gly Ser Asn Leu Gln Ser Gly Val Pro Ser Arg Phe Ser Gly
            50                  55                  60

Ser Gly Ser Gly Thr Asp Phe Thr Leu Thr Ile Ser Leu Gln Pro
65                  70                  75                 80

Glu Asp Phe Ala Thr Tyr Tyr Cys Gln Gln Ser Tyr Ser Thr Arg Tyr
                    85                  90                 95

Ser Phe Gly Gln Gly Thr Lys Leu Glu Ile Lys
            100                 105
```

<210> SEQ ID NO 47
<211> LENGTH: 122
<212> TYPE: PRT
<213> ORGANISM: Artificial sequence
<220> FEATURE:
<223> OTHER INFORMATION: Synthetic amino acid

<400> SEQUENCE: 47

```
              1               5                  10                 15
Gln Leu Gln Leu Gln Glu Ser Gly Pro Gly Leu Val Lys Pro Ser Glu

Thr Leu Ser Leu Thr Cys Thr Val Ser Gly Gly Ser Ile Ser Ser Val
                    20                  25                 30

Ser Tyr Tyr Trp Gly Trp Ile Arg Gln Pro Pro Gly Lys Gly Leu Glu
                    35                  40                 45

Trp Val Ala Ser Ile Phe Tyr Ser Gly Ser Thr Lys Tyr Asn Pro Ser
            50                  55                  60

Leu Glu Ser Arg Val Thr Ile Ser Val Asp Thr Ser Lys Asn Gln Phe
65                  70                  75                 80
```

Phe Leu Lys Leu Thr Ser Val Thr Ala Ala Asp Thr Ala Val Tyr Tyr
                85                  90                  95

Cys Ala Arg Gln Ile Tyr Tyr Tyr Glu Leu Glu Glu Phe Asp Tyr Trp
            100                 105                 110

Gly Gln Gly Thr Leu Val Thr Val Ser Ser
        115                 120

<210> SEQ ID NO 48

<400> SEQUENCE: 48

000

<210> SEQ ID NO 49

<400> SEQUENCE: 49

000

<210> SEQ ID NO 50
<211> LENGTH: 110
<212> TYPE: PRT
<213> ORGANISM: Artificial sequence
<220> FEATURE:
<223> OTHER INFORMATION: Synthetic amino acid

<400> SEQUENCE: 50

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Gly Val Phe Gly Gly Gly Thr Lys Leu Thr Val Leu
            100                 105                 110

<210> SEQ ID NO 51
<211> LENGTH: 120
<212> TYPE: PRT
<213> ORGANISM: Artificial sequence
<220> FEATURE:
<223> OTHER INFORMATION: Synthetic amino acid

<400> SEQUENCE: 51

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Pro Pro Gly Leu Arg Gly Asp Ala Phe Asp Ile Trp Gly Gln
            100                 105                 110

Gly Thr Leu Val Thr Val Ser Ser
        115                 120

<210> SEQ ID NO 52
<211> LENGTH: 110
<212> TYPE: PRT
<213> ORGANISM: Artificial sequence
<220> FEATURE:
<223> OTHER INFORMATION: Synthetic amino acid

<400> SEQUENCE: 52

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Asn Leu Val Phe Gly Gly Gly Thr Lys Leu Thr Val Leu
            100                 105                 110

<210> SEQ ID NO 53
<211> LENGTH: 122
<212> TYPE: PRT
<213> ORGANISM: Artificial sequence
<220> FEATURE:
<223> OTHER INFORMATION: Synthetic amino acid

<400> SEQUENCE: 53

Glu Val Gln Leu Val Gln Ser Gly Thr Glu Val Lys Lys Pro Gly Glu
1               5                   10                  15

Ser Leu Arg Ile Ser Cys Thr Gly Ser Lys His Met Phe Ser Asn Tyr
            20                  25                  30

Trp Ile Ala Trp Val Arg Gln Arg Pro Gly Lys Gly Leu Glu Trp Met
        35                  40                  45

Gly Ile Ile Tyr Pro Pro Asp Ala Asp Thr Arg Tyr Ser Pro Ser Phe
    50                  55                  60

Lys Gly Gln Val Thr Ile Ser Ala Asp Lys Ala Thr Asn Thr Ala Tyr
65                  70                  75                  80

Leu Gln Trp Ser Ser Leu Arg Ala Ser Asp Thr Ala Met Tyr Tyr Cys
                85                  90                  95

Ala Thr Thr Gly Gly Ser Gly Thr Tyr Leu Asp Tyr Phe Asp Tyr Trp
            100                 105                 110

Gly Gln Gly Thr Leu Val Thr Val Ser Ser
        115                 120

<210> SEQ ID NO 54

<400> SEQUENCE: 54
```

```
<210> SEQ ID NO 55
<211> LENGTH: 120
<212> TYPE: PRT
<213> ORGANISM: Artificial sequence
<220> FEATURE:
<223> OTHER INFORMATION: Synthetic amino acid

<400> SEQUENCE: 55

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Thr Trp Val Arg Gln Ala Pro Gly Lys Gly Leu Glu Trp Ile
        35                  40                  45

Gly Trp Ile Ser Pro Tyr Thr Gly Arg Ala Lys Phe Ala Leu Lys Phe
    50                  55                  60

Gln Gly Arg Phe Thr Leu Thr Thr Asp Thr Ser Thr Thr Thr Ala Tyr
65                  70                  75                  80

Met Glu Val Arg Ser Leu Lys Ser Asp Asp Ser Ala Val Tyr Tyr Cys
                85                  90                  95

Ala Arg Glu Gly Ile Lys Asp Ala Ser Ala Phe Asp Phe Trp Gly Gln
            100                 105                 110

Gly Thr Leu Val Thr Val Ser Ser
        115                 120

<210> SEQ ID NO 56
<211> LENGTH: 110
<212> TYPE: PRT
<213> ORGANISM: Artificial sequence
<220> FEATURE:
<223> OTHER INFORMATION: Synthetic amino acid

<400> SEQUENCE: 56

Gln Ser Ala Leu Thr Gln Pro Ala Ser Val Ser Gly Ser Pro Gly Gln
1               5                   10                  15

Ser Ile Thr Ile Ser Cys Thr Gly Thr Gly Ser Asp Ile Gly Gly Tyr
            20                  25                  30

Asn His Val Ser Trp Tyr His His Tyr Pro Gly Lys Ala Pro Lys Leu
        35                  40                  45

Leu Ile Phe Gly Val Thr His Arg Pro Ser Gly Val Ser Asp Arg Phe
    50                  55                  60

Ser Gly Ser Lys Ser Gly Val Thr Ala Phe Leu Thr Ile Ser Gly Leu
65                  70                  75                  80

Gln Ala Glu Asp Glu Ala Asp Tyr Tyr Cys Ser Ser Tyr Thr Asp Asn
                85                  90                  95

Thr Ser Trp Val Phe Gly Gly Gly Thr Lys Val Thr Val Leu
            100                 105                 110

<210> SEQ ID NO 57
<211> LENGTH: 124
<212> TYPE: PRT
<213> ORGANISM: Artificial sequence
<220> FEATURE:
<223> OTHER INFORMATION: Synthetic amino acid

<400> SEQUENCE: 57

Gln Val Thr Leu Lys Glu Ser Gly Pro Val Val Lys Pro Thr Glu
1               5                   10                  15
```

```
Thr Leu Thr Leu Thr Cys Thr Val Ser Asp Val Ser Leu Arg Asn Val
            20                  25                  30

Gln Met Gly Val Ser Trp Ile Arg Gln Pro Pro Gly Lys Ala Leu Glu
        35                  40                  45

Trp Leu Ala His Ile Phe Ser His Asp Glu Lys Ala Tyr Val Thr Ser
    50                  55                  60

Leu Glu Asn Arg Leu Thr Ile Ser Arg Asp Thr Ser Asn Ser Gln Val
65                  70                  75                  80

Val Leu Thr Met Thr Asn Met Asp Pro Val Asp Thr Gly Thr Tyr Tyr
                85                  90                  95

Cys Ala Arg Ile Arg Ser Thr Ser Gly Glu Glu Glu Asp Pro Phe Ala
            100                 105                 110

Phe Trp Gly Gln Gly Thr Leu Val Thr Val Ser Ser
        115                 120
```

<210> SEQ ID NO 58
<211> LENGTH: 106
<212> TYPE: PRT
<213> ORGANISM: Artificial sequence
<220> FEATURE:
<223> OTHER INFORMATION: Synthetic amino acid

<400> SEQUENCE: 58

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Thr Thr Trp
            20                  25                  30

Leu Ala Trp Tyr Gln Gln Lys Pro Gly Lys Ala Pro Lys Leu Leu Ile
        35                  40                  45

Tyr Ser Ala Ser Ser Leu Glu Ser Gly Val Pro Ser Arg Phe Ser Gly
    50                  55                  60

Ser Gly Ser Gly Thr Asp Phe Thr Leu Thr Ile Ser Asn Leu Gln Pro
65                  70                  75                  80

Asp Asp Phe Ala Thr Tyr Tyr Cys Gln Gln Tyr Arg Phe Tyr Trp Thr
                85                  90                  95

Phe Gly Gln Gly Thr Lys Val Glu Ser Lys
            100                 105
```

<210> SEQ ID NO 59
<211> LENGTH: 122
<212> TYPE: PRT
<213> ORGANISM: Artificial sequence
<220> FEATURE:
<223> OTHER INFORMATION: Synthetic amino acid

<400> SEQUENCE: 59

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Thr Ser Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ile Thr Ser
    50                  55                  60

Leu Lys Thr Arg Leu Ile Ile Ser Lys Asp Thr Ser Lys Asn Gln Val
65                  70                  75                  80

Val Leu Thr Met Thr Asn Met Asp Pro Val Asp Thr Ala Thr Tyr Tyr
```

```
                85                  90                  95
Cys Ala Arg Thr Gln Ser Gly Tyr Ser Gly Tyr Tyr Val Asp Tyr Trp
                100                 105                 110
Gly Gln Gly Thr Leu Val Thr Val Ser Ser
            115                 120
```

<210> SEQ ID NO 60
<211> LENGTH: 111
<212> TYPE: PRT
<213> ORGANISM: Artificial sequence
<220> FEATURE:
<223> OTHER INFORMATION: Synthetic amino acid

<400> SEQUENCE: 60

```
Gln Ser Val Leu Thr Gln Pro Pro Ser Ala Ser Gly Thr Pro Gly Gln
1               5                   10                  15
Lys Val Thr Ile Ser Cys Ser Gly Ser Ser Ser Asn Ile Gly Ser Asn
            20                  25                  30
Thr Val Asn Trp Tyr Gln Gln Leu Pro Gly Thr Ala Pro Lys Leu Leu
        35                  40                  45
Ile Tyr Ser Asn Asp Lys Arg Pro Ser Gly Val Pro Asp Arg Phe Ser
50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ser Ala Trp Asp Asp Ser Leu
                85                  90                  95
Asn Gly Arg Tyr Val Phe Gly Thr Gly Thr Lys Val Thr Val Leu
                100                 105                 110
```

<210> SEQ ID NO 61
<211> LENGTH: 129
<212> TYPE: PRT
<213> ORGANISM: Artificial sequence
<220> FEATURE:
<223> OTHER INFORMATION: Synthetic amino acid

<400> SEQUENCE: 61

```
Glu Val Gln Leu Val Gln Ser Gly Ala Glu Val Lys Lys Pro Gly Ala
1               5                   10                  15
Thr Met Lys Ile Ser Cys Lys Val Ser Gly Tyr Pro Phe Thr Asp Tyr
            20                  25                  30
Tyr Met His Trp Val Gln Gln Ala Pro Gly Lys Gly Leu Glu Trp Met
        35                  40                  45
Gly Leu Ile Asp Pro Glu Asp Gly Glu Thr Asn Tyr Ala Glu Lys Phe
50                  55                  60
Gln Gly Arg Val Thr Ile Thr Ala Asp Thr Ser Thr Asp Thr Val Tyr
65                  70                  75                  80
Met Glu Leu Ser Ser Leu Arg Ser Glu Asp Thr Ala Val Tyr Phe Cys
                85                  90                  95
Ala Lys Pro His Cys Ser Ser Arg Thr Cys Gln Arg Val Ser Gly Tyr
                100                 105                 110
Tyr Phe Gly Met Asp Val Trp Gly Gln Gly Thr Leu Val Thr Val Ser
            115                 120                 125
Ser
```

<210> SEQ ID NO 62
<211> LENGTH: 110
<212> TYPE: PRT

<213> ORGANISM: Artificial sequence
<220> FEATURE:
<223> OTHER INFORMATION: Synthetic amino acid

<400> SEQUENCE: 62

```
Gln Ser Ala Leu Thr Gln Pro Pro Ser Ala Ser Gly Ser Pro Gly Gln
1               5                   10                  15

Ser Val Thr Ile Ser Cys Thr Gly Ser Ser Asn Asp Val Gly Asp Tyr
            20                  25                  30

Asn Phe Val Ser Trp Tyr Gln Gln His Pro Gly Lys Pro Pro Lys Leu
        35                  40                  45

Met Ile Tyr Glu Val Thr Lys Arg Pro Ser Gly Val Pro Asp Arg Phe
50                  55                  60

Phe Gly Ser Lys Ser Gly Asn Thr Ala Ser Leu Thr Val Ser Gly Leu
65                  70                  75                  80

Gln Ala Asp Asp Glu Ala Asp Tyr Tyr Cys Ser Ser Tyr Ala Gly Gly
                85                  90                  95

Asn Ser Val Val Phe Gly Gly Gly Thr Lys Leu Thr Val Leu
            100                 105                 110
```

<210> SEQ ID NO 63
<211> LENGTH: 121
<212> TYPE: PRT
<213> ORGANISM: Artificial sequence
<220> FEATURE:
<223> OTHER INFORMATION: Synthetic amino acid

<400> SEQUENCE: 63

```
Gln Val Gln Leu Val Gln Ser Gly Ala Glu Val Lys Lys Pro Gly Ser
1               5                   10                  15

Ser Val Lys Val Ser Cys Arg Ala Ser Gly Gly Pro Phe Asn Thr Tyr
            20                  25                  30

Val Ile Thr Trp Val Arg Gln Ala Pro Gly Gln Gly Leu Glu Trp Met
        35                  40                  45

Gly Gly Ile Val Pro Val Phe Asn Thr Ser His Ser Ala Gln Lys Phe
50                  55                  60

Gln Gly Arg Val Lys Ile Ser Ala Asp Thr Ser Thr Asn Thr Val Tyr
65                  70                  75                  80

Met Glu Leu Thr Ser Leu Thr Phe Glu Asp Thr Ala Val Tyr Phe Cys
                85                  90                  95

Ala Arg Asp Gly Ala Ala Ala Pro Leu Asn Trp Tyr Asp Pro Trp Gly
            100                 105                 110

Gln Gly Thr Leu Val Thr Val Ser Ser
        115                 120
```

<210> SEQ ID NO 64
<211> LENGTH: 108
<212> TYPE: PRT
<213> ORGANISM: Artificial sequence
<220> FEATURE:
<223> OTHER INFORMATION: Synthetic amino acid

<400> SEQUENCE: 64

```
Ser Tyr Val Leu Thr Gln Pro Pro Ser Val Ser Leu Ala Pro Gly Gln
1               5                   10                  15

Thr Ala Thr Leu Thr Cys Gly Gly Asn Asn Ile Gly Ser Lys Ser Val
            20                  25                  30

His Trp Tyr Gln Lys Lys Pro Gly Gln Ala Pro Val Leu Val Val Tyr
        35                  40                  45
```

```
Asp Val Arg Asp Arg Pro Ser Gly Ile Pro Glu Arg Phe Ser Gly Ser
    50                  55                  60

Ser Ser Glu Asn Thr Ala Thr Leu Thr Leu Ser Arg Val Glu Ala Glu
65                  70                  75                  80

Asp Glu Ala Asp Tyr Tyr Cys Gln Val Trp Glu Ser Thr Thr Ser His
                85                  90                  95

Val Ile Phe Gly Gly Gly Thr Lys Leu Thr Val Leu
                100                 105
```

<210> SEQ ID NO 65
<211> LENGTH: 123
<212> TYPE: PRT
<213> ORGANISM: Artificial sequence
<220> FEATURE:
<223> OTHER INFORMATION: Synthetic amino acid

<400> SEQUENCE: 65

```
Glu Val Gln Leu Val Glu Ser Gly Gly Gly Leu Val Gln Thr Gly Gly
1               5                   10                  15

Ser Leu Arg Leu Ser Cys Ala Ala Ser Gly Phe Thr Phe Ser Arg Tyr
                20                  25                  30

Asn Met Asn Trp Val Arg Gln Ala Pro Gly Lys Gly Leu Glu Trp Val
                35                  40                  45

Ser Phe Ile Ser Ala Thr Ser Ser Ile Tyr Tyr Ala Asp Ser Val
    50                  55                  60

Lys Gly Arg Phe Thr Ile Ser Arg Asp Asn Ala Lys Asn Ser Leu Asp
65                  70                  75                  80

Leu Gln Met Asn Ser Leu Arg Asp Glu Asp Thr Ala Val Tyr Phe Cys
                85                  90                  95

Val Arg Glu Asp Ala Ala Ile Phe Gly Val Gly Ser Trp Phe Asp Pro
                100                 105                 110

Trp Gly Gln Gly Thr Leu Val Thr Val Ser Ser
                115                 120
```

<210> SEQ ID NO 66
<211> LENGTH: 108
<212> TYPE: PRT
<213> ORGANISM: Artificial sequence
<220> FEATURE:
<223> OTHER INFORMATION: Synthetic amino acid

<400> SEQUENCE: 66

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
                50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Glu Tyr Asn Asp Trp Pro Leu
                85                  90                  95

Tyr Thr Phe Gly Gln Gly Thr Lys Leu Glu Ile Lys
                100                 105
```

```
<210> SEQ ID NO 67
<211> LENGTH: 121
<212> TYPE: PRT
<213> ORGANISM: Artificial sequence
<220> FEATURE:
<223> OTHER INFORMATION: Synthetic amino acid

<400> SEQUENCE: 67

Gln Val Gln Leu Val Gln Ser Gly Ala Glu Val Lys Arg Pro Gly Ser
1               5                   10                  15

Ser Val Arg Val Ser Cys Lys Asp Ser Gly Asp Ser Phe Arg Arg Tyr
            20                  25                  30

Val Ile Asn Trp Val Arg Gln Ala Pro Gly Gln Gly Leu Glu Trp Met
        35                  40                  45

Gly Gly Ile Ile Pro Ile Phe Asp Lys Ala Lys Ser Val Gln Lys Phe
    50                  55                  60

Gln Asp Arg Leu Thr Ile Thr Ala Asp Glu Ser Thr Ser Thr Ser Tyr
65                  70                  75                  80

Met Glu Leu Ser Ser Leu Thr Ser Glu Asp Thr Ala Val Tyr Tyr Cys
                85                  90                  95

Ala Arg Lys Glu Asp Gly Arg Arg Asp Asp Val Phe Asp Ile Trp Gly
            100                 105                 110

Gln Gly Thr Leu Val Thr Val Ser Ser
        115                 120

<210> SEQ ID NO 68
<211> LENGTH: 107
<212> TYPE: PRT
<213> ORGANISM: Artificial sequence
<220> FEATURE:
<223> OTHER INFORMATION: Synthetic amino acid

<400> SEQUENCE: 68

Glu Ile Val Met Thr Gln Ser Pro Ala Thr Leu Ser Val Ser Leu Gly
1               5                   10                  15

Glu Arg Ala Thr Leu Ser Cys Arg Ala Ser His Ser Val Gly Ser Ser
            20                  25                  30

Leu Ala Trp Tyr Gln Gln Lys Pro Gly Leu Ala Pro Arg Leu Leu Ile
        35                  40                  45

Tyr Gly Val Ser Thr Arg Ala Thr Gly Ile Pro Ala Arg Phe Ser Gly
    50                  55                  60

Ser Gly Ser Ala Thr Glu Phe Thr Leu Thr Ile Ser Ser Leu Gln Ser
65                  70                  75                  80

Glu Asp Leu Ala Ala Tyr His Cys Gln Gln Tyr Asp Asn Trp Pro Phe
                85                  90                  95

Thr Phe Gly Gln Gly Thr Lys Leu Glu Ile Lys
            100                 105

<210> SEQ ID NO 69
<211> LENGTH: 120
<212> TYPE: PRT
<213> ORGANISM: Artificial sequence
<220> FEATURE:
<223> OTHER INFORMATION: Synthetic amino acid

<400> SEQUENCE: 69

Gln Val Thr Leu Arg Glu Ser Gly Pro Ala Leu Val Lys Pro Thr Glu
1               5                   10                  15

Thr Val Thr Leu Thr Cys Thr Phe Ser Gly Phe Ser Leu Ser Thr Ser
            20                  25                  30
```

```
Gly Met Cys Val Thr Trp Leu Arg Gln Pro Gly Lys Ala Leu Glu
            35                  40                  45

Trp Leu Ala Leu Ile Asp Trp Glu Asp Asp Lys Tyr Tyr Ser Thr Ser
 50                  55                  60

Leu Lys Thr Arg Phe Thr Ile Ser Lys Asp Ser Lys Asn Gln Val
 65                  70                  75                  80

Val Leu Thr Met Thr Asn Met Asp Pro Val Asp Thr Ala Thr Tyr Tyr
                    85                  90                  95

Cys Ala Arg Thr Pro Thr Tyr Arg Gly Ala Phe Asp Met Trp Gly Gln
                100                 105                 110

Gly Thr Leu Val Thr Val Ser Ser
            115                 120

<210> SEQ ID NO 70
<211> LENGTH: 110
<212> TYPE: PRT
<213> ORGANISM: Artificial sequence
<220> FEATURE:
<223> OTHER INFORMATION: Synthetic amino acid

<400> SEQUENCE: 70

Gln Ser Val Leu Thr Gln Pro Pro Ser Ala Ser Gly Thr Pro Gly Gln
 1               5                  10                  15

Arg Val Thr Ile Ser Cys Ser Gly Ser Thr Ser Asn Ile Gly Ser Asn
                20                  25                  30

Thr Val Asn Trp Tyr Gln Gln Leu Pro Gly Thr Ala Pro Gln Leu Leu
            35                  40                  45

Ile Tyr Asn Asn Asn Gln Arg Pro Ser Gly Val Pro Asp Arg Phe Ser
 50                  55                  60

Gly Ser Lys Pro Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
                100                 105                 110

<210> SEQ ID NO 71
<211> LENGTH: 122
<212> TYPE: PRT
<213> ORGANISM: Artificial sequence
<220> FEATURE:
<223> OTHER INFORMATION: Synthetic amino acid

<400> SEQUENCE: 71

Gln Val Gln Leu Val Gln Ser Gly Ala Glu Val Lys Lys Thr Gly Ser
 1               5                  10                  15

Ser Val Lys Val Ser Cys Thr Ala Ser Gly Ala Thr Phe Asn Thr Asn
                20                  25                  30

Asp Leu Met Trp Val Arg Gln Ala Pro Gly Gln Gly Leu Glu Trp Met
            35                  40                  45

Gly Gly Ile Val Pro Val Phe Gly Arg Pro Lys Tyr Ala Lys Lys Phe
 50                  55                  60

His Gly Arg Leu Ile Ile Ser Ala Asp Glu Phe Thr Thr Thr Phe Tyr
 65                  70                  75                  80

Met Glu Leu Thr Ser Leu Thr Phe Asp Asp Thr Ala Ile Tyr Tyr Cys
                85                  90                  95

Ala Arg Ser Gly Ser Thr Glu Ser Pro Ile Gln His Ile Asp Phe Trp
```

```
                 100                 105                 110
Gly Gln Gly Thr Leu Val Thr Val Ser Ser
            115                 120

<210> SEQ ID NO 72
<211> LENGTH: 108
<212> TYPE: PRT
<213> ORGANISM: Artificial sequence
<220> FEATURE:
<223> OTHER INFORMATION: Synthetic amino acid

<400> SEQUENCE: 72

Ser Tyr Val Leu Thr Gln Pro Pro Ser Val Ser Val Ala Pro Gly Gln
1               5                   10                  15

Thr Ala Thr Ile Thr Cys Gly Gly Asp Asn Ile Ala Thr Phe Ser Val
            20                  25                  30

His Trp Tyr Arg Gln Lys Pro Gly Gln Ala Pro Val Leu Val Val Tyr
        35                  40                  45

Asp Asp Leu Asp Arg Ala Ser Gly Ile Pro Ala Arg Phe Ser Gly Ser
    50                  55                  60

Asn Ser Gly Asn Thr Ala Thr Leu Thr Ile Ser Arg Val Glu Pro Gly
65                  70                  75                  80

Asp Glu Ala Asp Tyr Phe Cys Gln Val Trp Glu Ile Ser Ser Asp Glu
                85                  90                  95

Tyr Val Phe Gly Pro Gly Thr Ser Val Thr Val Leu
            100                 105

<210> SEQ ID NO 73
<211> LENGTH: 118
<212> TYPE: PRT
<213> ORGANISM: Artificial sequence
<220> FEATURE:
<223> OTHER INFORMATION: Synthetic amino acid

<400> SEQUENCE: 73

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Val Gly Asp Arg Tyr Tyr Phe Asp Tyr Trp Gly Gln Gly Thr
            100                 105                 110

Leu Val Thr Val Ser Ser
        115

<210> SEQ ID NO 74
<211> LENGTH: 111
<212> TYPE: PRT
<213> ORGANISM: Artificial sequence
<220> FEATURE:
<223> OTHER INFORMATION: Synthetic amino acid

<400> SEQUENCE: 74
```

-continued

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Leu
        35                  40                  45

Met Ile Tyr Glu Gly Ser Lys Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Phe Val Val Phe Gly Gly Gly Thr Lys Leu Thr Val Leu
            100                 105                 110

<210> SEQ ID NO 75
<211> LENGTH: 127
<212> TYPE: PRT
<213> ORGANISM: Artificial sequence
<220> FEATURE:
<223> OTHER INFORMATION: Synthetic amino acid

<400> SEQUENCE: 75

Gln Val Gln Leu Val Gln Ser Gly Ala Glu Val Lys Gln Ser Gly Ser
1               5                   10                  15

Ser Leu Lys Val Ser Cys Lys Val Ser Gly Gly Asn Leu Arg Ser Tyr
            20                  25                  30

Gly Ile Ser Trp Val Arg Gln Ala Pro Gly Gln Gly Leu Glu Trp Met
        35                  40                  45

Gly Val Ile Ile Pro Ile Phe Gly Ala Pro Thr Tyr Ala Gln Lys Phe
50                  55                  60

Gln Gly Arg Val Thr Phe Val Ala Asp Asp Gly Asn Asn Val Val Phe
65                  70                  75                  80

Met Glu Leu Ser Ser Leu Arg Ser Glu Asp Thr Ala Val Tyr Tyr Cys
                85                  90                  95

Ala Arg Asp Trp Pro Ser Ile Thr Val Ala Val Asp Ala Ile Asn Phe
            100                 105                 110

Ala Met Asp Val Trp Gly Gln Gly Thr Leu Val Thr Val Ser Ser
        115                 120                 125

<210> SEQ ID NO 76
<211> LENGTH: 110
<212> TYPE: PRT
<213> ORGANISM: Artificial sequence
<220> FEATURE:
<223> OTHER INFORMATION: Synthetic amino acid

<400> SEQUENCE: 76

Gln Ser Ala Leu Thr Gln Pro Arg Ser Val Ser Gly Ser Pro Gly Gln
1               5                   10                  15

Ser Val Thr Ile Ser Cys Thr Gly Thr Asn Asn Asp Val Gly Ser Tyr
            20                  25                  30

Asp His Val Ser Trp Tyr Gln Gln His Pro Gly Lys Ala Pro Lys Phe
        35                  40                  45

Ile Ile Tyr Asp Val Ser Thr Arg Pro Ser Gly Val Pro Asp Arg Phe
50                  55                  60

Ser Gly Ser Lys Ser Asp Asn Thr Ala Ser Leu Thr Ile Ser Gly Leu 65                  70                  75                  80
Gln Ala Glu Asp Glu Ala Asp Tyr Tyr Cys Cys Ser Phe Ala Gly Ser
                    85                  90                  95

Tyr Thr Tyr Val Phe Gly Thr Gly Thr Val Thr Val Leu
                100                 105                 110

<210> SEQ ID NO 77
<211> LENGTH: 127
<212> TYPE: PRT
<213> ORGANISM: Artificial sequence
<220> FEATURE:
<223> OTHER INFORMATION: Synthetic amino acid

<400> SEQUENCE: 77

Gln Val Gln Leu Val Gln Ser Gly Ala Glu Val Lys Lys Pro Gly Ser
1               5                   10                  15

Ser Leu Lys Val Ser Cys Lys Val Ser Gly Gly Asn Leu Arg Ser Tyr
                20                  25                  30

Gly Ile Ser Trp Val Arg Gln Ala Pro Gly Gln Gly Leu Glu Trp Met
            35                  40                  45

Gly Val Ile Ile Pro Ile Phe Gly Thr Pro Thr Tyr Ala Gln Lys Phe
        50                  55                  60

Gln Gly Arg Val Thr Leu Ala Ala Asp Asp Ser Asn Ile Val Phe
65                  70                  75                  80

Met Glu Leu Ser Ser Leu Arg Ser Glu Asp Thr Ala Val Tyr Tyr Cys
                85                  90                  95

Ala Arg Asp Trp Pro Ser Ile Val Ala Val Asp Ala Thr Asn Tyr
                100                 105                 110

Gly Met Asp Val Trp Gly Gln Gly Thr Leu Val Thr Val Ser Ser
            115                 120                 125

<210> SEQ ID NO 78
<211> LENGTH: 110
<212> TYPE: PRT
<213> ORGANISM: Artificial sequence
<220> FEATURE:
<223> OTHER INFORMATION: Synthetic amino acid

<400> SEQUENCE: 78

Gln Ser Ala Leu Thr Gln Pro Arg Ser Val Ser Gly Ser Pro Gly Gln
1               5                   10                  15

Ser Val Thr Ile Ser Cys Thr Gly Thr Ser Asn Asp Val Gly Tyr Tyr
                20                  25                  30

Asp His Val Ser Trp Tyr Gln Gln His Pro Gly Lys Ala Pro Lys Phe
            35                  40                  45

Ile Ile Tyr Asp Val Ser Lys Arg Pro Ser Gly Val Pro Asp Arg Phe
        50                  55                  60

Ser Gly Ser Lys Ser Asp Asn Thr Ala Ser Leu Thr Ile Ser Gly Leu
65                  70                  75                  80

Gln Ala Glu Asp Glu Ala Asp Tyr Tyr Cys Cys Ser Phe Ala Gly Ser
                85                  90                  95

Tyr Thr Tyr Val Phe Gly Thr Gly Thr Lys Val Thr Val Leu
                100                 105                 110

<210> SEQ ID NO 79
<211> LENGTH: 122
<212> TYPE: PRT
<213> ORGANISM: Artificial sequence
<220> FEATURE:

<223> OTHER INFORMATION: Synthetic amino acid

<400> SEQUENCE: 79

Gln Val Gln Leu Val Gln Ser Gly Pro Glu Ala Arg Lys Pro Gly Thr
1               5                   10                  15

Ser Val Lys Val Ser Cys Lys Thr Ser Gly Tyr Thr Phe Ser Ser Tyr
            20                  25                  30

Gly Ile Ala Trp Val Arg Gln Ala Pro Gly Gln Gly Leu Glu Trp Met
        35                  40                  45

Gly Trp Ile Ser Gly Tyr Ser Asp Tyr Thr Ile Tyr Ala Gln Arg Leu
    50                  55                  60

Gln Gly Arg Val Ser Met Thr Thr Asp Pro Tyr Thr Ser Thr Ala Tyr
65                  70                  75                  80

Met Glu Leu Arg Ser Leu Arg Pro Asp Asp Thr Ala Val Tyr Tyr Cys
                85                  90                  95

Ala Thr Leu Ser Phe Gly Glu Leu Val Glu Asn Lys Leu Asp Phe Trp
            100                 105                 110

Gly Gln Gly Thr Leu Val Thr Val Ser Ser
        115                 120

<210> SEQ ID NO 80
<211> LENGTH: 112
<212> TYPE: PRT
<213> ORGANISM: Artificial sequence
<220> FEATURE:
<223> OTHER INFORMATION: Synthetic amino acid

<400> SEQUENCE: 80

Gln Ser Val Leu Thr Gln Pro Pro Ser Val Ser Gly Ala Pro Gly Gln
1               5                   10                  15

Arg Val Thr Ile Ser Cys Thr Gly Thr Ser Ser Asn Ile Gly Ala Asp
            20                  25                  30

Tyr Ala Val His Trp Tyr Gln Gln Leu Pro Gly Thr Ala Pro Lys Leu
        35                  40                  45

Leu Ile Tyr Gly Thr Ile Asn Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Ala Asp Asp Glu Ala Asp Tyr Tyr Cys Gln Ser Tyr Asp Ser Ser
                85                  90                  95

Leu Ser Gly Ser Val Val Phe Gly Gly Gly Thr Lys Leu Thr Val Leu
            100                 105                 110

<210> SEQ ID NO 81
<211> LENGTH: 122
<212> TYPE: PRT
<213> ORGANISM: Artificial sequence
<220> FEATURE:
<223> OTHER INFORMATION: Synthetic amino acid

<400> SEQUENCE: 81

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser

```
                    50                  55                  60
Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Pro Asn Ser Ser Gly Trp Ser Tyr Tyr Phe Asp Tyr Trp
                100                 105                 110

Gly Gln Gly Thr Leu Val Thr Val Ser Ser
            115                 120

<210> SEQ ID NO 82
<211> LENGTH: 112
<212> TYPE: PRT
<213> ORGANISM: Artificial sequence
<220> FEATURE:
<223> OTHER INFORMATION: Synthetic amino acid

<400> SEQUENCE: 82

Gln Ser Val Leu Thr Gln Pro Pro Ser Val Ser Gly Ala Pro Gly Gln
 1               5                  10                  15

Arg Val Thr Ile Ser Cys Thr Gly Thr Ser Ser Asn Ile Gly Ala Asp
                20                  25                  30

Tyr Asp Val His Trp Tyr Gln Gln Leu Pro Gly Thr Ala Pro Lys Leu
            35                  40                  45

Leu Ile Tyr Gly Asn Ile Asn Arg Pro Ser Gly Val Pro Asp Arg Phe
        50                  55                  60

Ser Gly Ser Arg Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Ser Ser
                 85                  90                  95

Leu Ser Gly Ser Val Val Phe Gly Gly Gly Thr Lys Leu Thr Val Leu
                100                 105                 110

<210> SEQ ID NO 83
<211> LENGTH: 119
<212> TYPE: PRT
<213> ORGANISM: Artificial sequence
<220> FEATURE:
<223> OTHER INFORMATION: Synthetic amino acid

<400> SEQUENCE: 83

Gln Leu Gln Leu Gln Glu Ser Gly Pro Gly Leu Val Lys Pro Ser Glu
 1               5                  10                  15

Thr Leu Ser Leu Thr Cys Ser Val Ser Gly Gly Ser Ile Ser Arg Thr
                20                  25                  30

Tyr Tyr Tyr Trp Asp Trp Ile Arg Gln Pro Pro Gly Lys Gly Leu Glu
            35                  40                  45

Trp Ile Gly Ser Val Tyr Tyr Ser Gly Ser Thr Tyr Tyr Asn Pro Ser
        50                  55                  60

Leu Lys Ser Arg Val Thr Met Ser Val Asp Thr Ser Lys Asn Leu Phe
 65                  70                  75                  80

Ser Leu Lys Leu Ser Ser Val Thr Ala Ala Asp Thr Ala Val Tyr Tyr
                     85                  90                  95

Cys Ala Ser His Glu Ser Trp Gln Gln Leu Ile Ser Trp Gly Gln Gly
                100                 105                 110

Thr Leu Val Thr Val Ser Ser
            115
```

<210> SEQ ID NO 84
<211> LENGTH: 115
<212> TYPE: PRT
<213> ORGANISM: Artificial sequence
<220> FEATURE:
<223> OTHER INFORMATION: Synthetic amino acid

<400> SEQUENCE: 84

```
Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Ile
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys His Gln Gly Ser Gly Val
        50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Val Ala Phe Gly Gly Gly Thr Lys Leu
            100                 105                 110

Thr Val Leu
        115
```

<210> SEQ ID NO 85
<211> LENGTH: 8
<212> TYPE: PRT
<213> ORGANISM: Artificial sequence
<220> FEATURE:
<223> OTHER INFORMATION: Synthetic amino acid

<400> SEQUENCE: 85

```
Gly Phe Thr Phe Ser Asp Tyr Tyr
1               5
```

<210> SEQ ID NO 86
<211> LENGTH: 8
<212> TYPE: PRT
<213> ORGANISM: Artificial sequence
<220> FEATURE:
<223> OTHER INFORMATION: Synthetic amino acid

<400> SEQUENCE: 86

```
Ile Ser Ser Ser Gly Ser Thr Ile
1               5
```

<210> SEQ ID NO 87
<211> LENGTH: 22
<212> TYPE: PRT
<213> ORGANISM: Artificial sequence
<220> FEATURE:
<223> OTHER INFORMATION: Synthetic amino acid

<400> SEQUENCE: 87

```
Ala Arg Glu Thr Pro Arg Arg Ile Thr Gly Met Gly Leu Glu Asp Tyr
1               5                   10                  15

Tyr Tyr Gly Met Asp Val
            20
```

<210> SEQ ID NO 88
<211> LENGTH: 8

```
<212> TYPE: PRT
<213> ORGANISM: Artificial sequence
<220> FEATURE:
<223> OTHER INFORMATION: Synthetic amino acid

<400> SEQUENCE: 88

Gly Phe Ser Phe Ser Tyr Tyr Ser
1               5

<210> SEQ ID NO 89
<211> LENGTH: 8
<212> TYPE: PRT
<213> ORGANISM: Artificial sequence
<220> FEATURE:
<223> OTHER INFORMATION: Synthetic amino acid

<400> SEQUENCE: 89

Ile Ser Ser Ser Gly Glu Tyr Ile
1               5

<210> SEQ ID NO 90
<211> LENGTH: 11
<212> TYPE: PRT
<213> ORGANISM: Artificial sequence
<220> FEATURE:
<223> OTHER INFORMATION: Synthetic amino acid

<400> SEQUENCE: 90

Ala Lys Val Val Ser Gln Gln Ser Leu Asp Tyr
1               5                   10

<210> SEQ ID NO 91
<211> LENGTH: 10
<212> TYPE: PRT
<213> ORGANISM: Artificial sequence
<220> FEATURE:
<223> OTHER INFORMATION: Synthetic amino acid

<400> SEQUENCE: 91

Gly Gly Ser Ile Ser Ser Val Ser Tyr Tyr
1               5                   10

<210> SEQ ID NO 92
<211> LENGTH: 7
<212> TYPE: PRT
<213> ORGANISM: Artificial sequence
<220> FEATURE:
<223> OTHER INFORMATION: Synthetic amino acid

<400> SEQUENCE: 92

Ile Phe Tyr Ser Gly Ser Thr
1               5

<210> SEQ ID NO 93
<211> LENGTH: 14
<212> TYPE: PRT
<213> ORGANISM: Artificial sequence
<220> FEATURE:
<223> OTHER INFORMATION: Synthetic amino acid

<400> SEQUENCE: 93

Ala Arg Gln Ile Tyr Tyr Tyr Glu Leu Glu Glu Phe Asp Tyr
1               5                   10

<210> SEQ ID NO 94

<400> SEQUENCE: 94
```

000

<210> SEQ ID NO 95

<400> SEQUENCE: 95

000

<210> SEQ ID NO 96

<400> SEQUENCE: 96

000

<210> SEQ ID NO 97
<211> LENGTH: 8
<212> TYPE: PRT
<213> ORGANISM: Artificial sequence
<220> FEATURE:
<223> OTHER INFORMATION: Synthetic amino acid

<400> SEQUENCE: 97

Gly Tyr Ser Phe Thr Ser Tyr Trp
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic amino acid

<400> SEQUENCE: 98

Ile Tyr Pro Gly Asp Ser Asp Thr
1               5

<210> SEQ ID NO 99
<211> LENGTH: 13
<212> TYPE: PRT
<213> ORGANISM: Artificial sequence
<220> FEATURE:
<223> OTHER INFORMATION: Synthetic amino acid

<400> SEQUENCE: 99

Ala Arg Pro Pro Gly Leu Arg Gly Asp Ala Phe Asp Ile
1               5                   10

<210> SEQ ID NO 100
<211> LENGTH: 8
<212> TYPE: PRT
<213> ORGANISM: Artificial sequence
<220> FEATURE:
<223> OTHER INFORMATION: Synthetic amino acid

<400> SEQUENCE: 100

Lys His Met Phe Ser Asn Tyr Trp
1               5

<210> SEQ ID NO 101
<211> LENGTH: 8
<212> TYPE: PRT
<213> ORGANISM: Artificial sequence
<220> FEATURE:
<223> OTHER INFORMATION: Synthetic amino acid

<400> SEQUENCE: 101

```
Ile Tyr Pro Pro Asp Ala Asp Thr
1               5
```

<210> SEQ ID NO 102
<211> LENGTH: 15
<212> TYPE: PRT
<213> ORGANISM: Artificial sequence
<220> FEATURE:
<223> OTHER INFORMATION: Synthetic amino acid

<400> SEQUENCE: 102

```
Ala Thr Thr Gly Gly Ser Gly Thr Tyr Leu Asp Tyr Phe Asp Tyr
1               5                   10                  15
```

<210> SEQ ID NO 103
<211> LENGTH: 8
<212> TYPE: PRT
<213> ORGANISM: Artificial sequence
<220> FEATURE:
<223> OTHER INFORMATION: Synthetic amino acid

<400> SEQUENCE: 103

```
Gly Tyr Thr Phe Thr Asn Tyr Gly
1               5
```

<210> SEQ ID NO 104
<211> LENGTH: 8
<212> TYPE: PRT
<213> ORGANISM: Artificial sequence
<220> FEATURE:
<223> OTHER INFORMATION: Synthetic amino acid

<400> SEQUENCE: 104

```
Ile Ser Pro Tyr Thr Gly Arg Ala
1               5
```

<210> SEQ ID NO 105
<211> LENGTH: 13
<212> TYPE: PRT
<213> ORGANISM: Artificial sequence
<220> FEATURE:
<223> OTHER INFORMATION: Synthetic amino acid

<400> SEQUENCE: 105

```
Ala Arg Glu Gly Ile Lys Asp Ala Ser Ala Phe Asp Phe
1               5                   10
```

<210> SEQ ID NO 106
<211> LENGTH: 10
<212> TYPE: PRT
<213> ORGANISM: Artificial sequence
<220> FEATURE:
<223> OTHER INFORMATION: Synthetic amino acid

<400> SEQUENCE: 106

```
Asp Val Ser Leu Arg Asn Val Gln Met Gly
1               5                   10
```

<210> SEQ ID NO 107
<211> LENGTH: 7
<212> TYPE: PRT
<213> ORGANISM: Artificial sequence
<220> FEATURE:
<223> OTHER INFORMATION: Synthetic amino acid

<400> SEQUENCE: 107

```
Ile Phe Ser His Asp Glu Lys
```

```
1               5
```

<210> SEQ ID NO 108
<211> LENGTH: 16
<212> TYPE: PRT
<213> ORGANISM: Artificial sequence
<220> FEATURE:
<223> OTHER INFORMATION: Synthetic amino acid

<400> SEQUENCE: 108

```
Ala Arg Ile Arg Ser Thr Ser Gly Glu Glu Glu Asp Pro Phe Ala Phe
1               5                   10                  15
```

<210> SEQ ID NO 109
<211> LENGTH: 10
<212> TYPE: PRT
<213> ORGANISM: Artificial sequence
<220> FEATURE:
<223> OTHER INFORMATION: Synthetic amino acid

<400> SEQUENCE: 109

```
Gly Phe Ser Leu Thr Ser Ser Gly Met Cys
1               5                   10
```

<210> SEQ ID NO 110
<211> LENGTH: 7
<212> TYPE: PRT
<213> ORGANISM: Artificial sequence
<220> FEATURE:
<223> OTHER INFORMATION: Synthetic amino acid

<400> SEQUENCE: 110

```
Ile Asp Trp Asp Asp Asp Lys
1               5
```

<210> SEQ ID NO 111
<211> LENGTH: 14
<212> TYPE: PRT
<213> ORGANISM: Artificial sequence
<220> FEATURE:
<223> OTHER INFORMATION: Synthetic amino acid

<400> SEQUENCE: 111

```
Ala Arg Thr Gln Ser Gly Tyr Ser Gly Tyr Tyr Val Asp Tyr
1               5                   10
```

<210> SEQ ID NO 112
<211> LENGTH: 8
<212> TYPE: PRT
<213> ORGANISM: Artificial sequence
<220> FEATURE:
<223> OTHER INFORMATION: Synthetic amino acid

<400> SEQUENCE: 112

```
Gly Tyr Pro Phe Thr Asp Tyr Tyr
1               5
```

<210> SEQ ID NO 113
<211> LENGTH: 8
<212> TYPE: PRT
<213> ORGANISM: Artificial sequence
<220> FEATURE:
<223> OTHER INFORMATION: Synthetic amino acid

<400> SEQUENCE: 113

```
Ile Asp Pro Glu Asp Gly Glu Thr
1               5
```

<210> SEQ ID NO 114
<211> LENGTH: 22
<212> TYPE: PRT
<213> ORGANISM: Artificial sequence
<220> FEATURE:
<223> OTHER INFORMATION: Synthetic amino acid

<400> SEQUENCE: 114

Ala Lys Pro His Cys Ser Ser Arg Thr Cys Gln Arg Val Ser Gly Tyr
1               5                   10                  15

Tyr Phe Gly Met Asp Val
            20

<210> SEQ ID NO 115
<211> LENGTH: 8
<212> TYPE: PRT
<213> ORGANISM: Artificial sequence
<220> FEATURE:
<223> OTHER INFORMATION: Synthetic amino acid

<400> SEQUENCE: 115

Gly Gly Pro Phe Asn Thr Tyr Val
1               5

<210> SEQ ID NO 116
<211> LENGTH: 8
<212> TYPE: PRT
<213> ORGANISM: Artificial sequence
<220> FEATURE:
<223> OTHER INFORMATION: Synthetic amino acid

<400> SEQUENCE: 116

Ile Val Pro Val Phe Asn Thr Ser
1               5

<210> SEQ ID NO 117
<211> LENGTH: 14
<212> TYPE: PRT
<213> ORGANISM: Artificial sequence
<220> FEATURE:
<223> OTHER INFORMATION: Synthetic amino acid

<400> SEQUENCE: 117

Ala Arg Asp Gly Ala Ala Ala Pro Leu Asn Trp Tyr Asp Pro
1               5                   10

<210> SEQ ID NO 118
<211> LENGTH: 8
<212> TYPE: PRT
<213> ORGANISM: Artificial sequence
<220> FEATURE:
<223> OTHER INFORMATION: Synthetic amino acid

<400> SEQUENCE: 118

Gly Phe Thr Phe Ser Arg Tyr Asn
1               5

<210> SEQ ID NO 119
<211> LENGTH: 8
<212> TYPE: PRT
<213> ORGANISM: Artificial sequence
<220> FEATURE:
<223> OTHER INFORMATION: Synthetic amino acid

<400> SEQUENCE: 119

Ile Ser Ala Thr Ser Ser Ser Ile
1               5

<210> SEQ ID NO 120
<211> LENGTH: 16
<212> TYPE: PRT
<213> ORGANISM: Artificial sequence
<220> FEATURE:
<223> OTHER INFORMATION: Synthetic amino acid

<400> SEQUENCE: 120

Val Arg Glu Asp Ala Ala Ile Phe Gly Val Gly Ser Trp Phe Asp Pro
1               5                   10                  15

<210> SEQ ID NO 121
<211> LENGTH: 8
<212> TYPE: PRT
<213> ORGANISM: Artificial sequence
<220> FEATURE:
<223> OTHER INFORMATION: Synthetic amino acid

<400> SEQUENCE: 121

Gly Asp Ser Phe Arg Arg Tyr Val
1               5

<210> SEQ ID NO 122
<211> LENGTH: 8
<212> TYPE: PRT
<213> ORGANISM: Artificial sequence
<220> FEATURE:
<223> OTHER INFORMATION: Synthetic amino acid

<400> SEQUENCE: 122

Ile Ile Pro Ile Phe Asp Lys Ala
1               5

<210> SEQ ID NO 123
<211> LENGTH: 14
<212> TYPE: PRT
<213> ORGANISM: Artificial sequence
<220> FEATURE:
<223> OTHER INFORMATION: Synthetic amino acid

<400> SEQUENCE: 123

Ala Arg Lys Glu Asp Gly Arg Arg Asp Asp Val Phe Asp Ile
1               5                   10

<210> SEQ ID NO 124
<211> LENGTH: 10
<212> TYPE: PRT
<213> ORGANISM: Artificial sequence
<220> FEATURE:
<223> OTHER INFORMATION: Synthetic amino acid

<400> SEQUENCE: 124

Gly Phe Ser Leu Ser Thr Ser Gly Met Cys
1               5                   10

<210> SEQ ID NO 125
<211> LENGTH: 7
<212> TYPE: PRT
<213> ORGANISM: Artificial sequence
<220> FEATURE:
<223> OTHER INFORMATION: Synthetic amino acid

<400> SEQUENCE: 125

Ile Asp Trp Glu Asp Asp Lys

```
1               5
```

<210> SEQ ID NO 126
<211> LENGTH: 12
<212> TYPE: PRT
<213> ORGANISM: Artificial sequence
<220> FEATURE:
<223> OTHER INFORMATION: Synthetic amino acid

<400> SEQUENCE: 126

```
Ala Arg Thr Pro Thr Tyr Arg Gly Ala Phe Asp Met
1               5                   10
```

<210> SEQ ID NO 127
<211> LENGTH: 8
<212> TYPE: PRT
<213> ORGANISM: Artificial sequence
<220> FEATURE:
<223> OTHER INFORMATION: Synthetic amino acid

<400> SEQUENCE: 127

```
Gly Ala Thr Phe Asn Thr Asn Asp
1               5
```

<210> SEQ ID NO 128
<211> LENGTH: 8
<212> TYPE: PRT
<213> ORGANISM: Artificial sequence
<220> FEATURE:
<223> OTHER INFORMATION: Synthetic amino acid

<400> SEQUENCE: 128

```
Ile Val Pro Val Phe Gly Arg Pro
1               5
```

<210> SEQ ID NO 129
<211> LENGTH: 15
<212> TYPE: PRT
<213> ORGANISM: Artificial sequence
<220> FEATURE:
<223> OTHER INFORMATION: Synthetic amino acid

<400> SEQUENCE: 129

```
Ala Arg Ser Gly Ser Thr Glu Ser Pro Ile Gln His Ile Asp Phe
1               5                   10                  15
```

<210> SEQ ID NO 130
<211> LENGTH: 8
<212> TYPE: PRT
<213> ORGANISM: Artificial sequence
<220> FEATURE:
<223> OTHER INFORMATION: Synthetic amino acid

<400> SEQUENCE: 130

```
Gly Gly Ser Phe Ser Gly Tyr Tyr
1               5
```

<210> SEQ ID NO 131
<211> LENGTH: 7
<212> TYPE: PRT
<213> ORGANISM: Artificial sequence
<220> FEATURE:
<223> OTHER INFORMATION: Synthetic amino acid

<400> SEQUENCE: 131

```
Ile Asn His Ser Gly Ser Thr
1               5
```

<210> SEQ ID NO 132
<211> LENGTH: 12
<212> TYPE: PRT
<213> ORGANISM: Artificial sequence
<220> FEATURE:
<223> OTHER INFORMATION: Synthetic amino acid

<400> SEQUENCE: 132

Ala Arg Asp Val Gly Asp Arg Tyr Tyr Phe Asp Tyr
1               5                   10

<210> SEQ ID NO 133
<211> LENGTH: 8
<212> TYPE: PRT
<213> ORGANISM: Artificial sequence
<220> FEATURE:
<223> OTHER INFORMATION: Synthetic amino acid

<400> SEQUENCE: 133

Gly Gly Asn Leu Arg Ser Tyr Gly
1               5

<210> SEQ ID NO 134
<211> LENGTH: 8
<212> TYPE: PRT
<213> ORGANISM: Artificial sequence
<220> FEATURE:
<223> OTHER INFORMATION: Synthetic amino acid

<400> SEQUENCE: 134

Ile Ile Pro Ile Phe Gly Ala Pro
1               5

<210> SEQ ID NO 135
<211> LENGTH: 20
<212> TYPE: PRT
<213> ORGANISM: Artificial sequence
<220> FEATURE:
<223> OTHER INFORMATION: Synthetic amino acid

<400> SEQUENCE: 135

Ala Arg Asp Trp Pro Ser Ile Thr Val Ala Val Asp Ala Ile Asn Phe
1               5                   10                  15

Ala Met Asp Val
            20

<210> SEQ ID NO 136
<211> LENGTH: 8
<212> TYPE: PRT
<213> ORGANISM: Artificial sequence
<220> FEATURE:
<223> OTHER INFORMATION: Synthetic amino acid

<400> SEQUENCE: 136

Gly Gly Asn Leu Arg Ser Tyr Gly
1               5

<210> SEQ ID NO 137
<211> LENGTH: 8
<212> TYPE: PRT
<213> ORGANISM: Artificial sequence
<220> FEATURE:
<223> OTHER INFORMATION: Synthetic amino acid

<400> SEQUENCE: 137

```
Ile Ile Pro Ile Phe Gly Thr Pro
1               5

<210> SEQ ID NO 138
<211> LENGTH: 20
<212> TYPE: PRT
<213> ORGANISM: Artificial sequence
<220> FEATURE:
<223> OTHER INFORMATION: Synthetic amino acid

<400> SEQUENCE: 138

Ala Arg Asp Trp Pro Ser Ile Thr Val Ala Val Asp Ala Thr Asn Tyr
1               5                   10                  15

Gly Met Asp Val
            20

<210> SEQ ID NO 139
<211> LENGTH: 8
<212> TYPE: PRT
<213> ORGANISM: Artificial sequence
<220> FEATURE:
<223> OTHER INFORMATION: Synthetic amino acid

<400> SEQUENCE: 139

Gly Tyr Thr Phe Ser Ser Tyr Gly
1               5

<210> SEQ ID NO 140
<211> LENGTH: 8
<212> TYPE: PRT
<213> ORGANISM: Artificial sequence
<220> FEATURE:
<223> OTHER INFORMATION: Synthetic amino acid

<400> SEQUENCE: 140

Ile Ser Gly Tyr Ser Asp Tyr Thr
1               5

<210> SEQ ID NO 141
<211> LENGTH: 15
<212> TYPE: PRT
<213> ORGANISM: Artificial sequence
<220> FEATURE:
<223> OTHER INFORMATION: Synthetic amino acid

<400> SEQUENCE: 141

Ala Thr Leu Ser Phe Gly Glu Leu Val Glu Asn Lys Leu Asp Phe
1               5                   10                  15

<210> SEQ ID NO 142
<211> LENGTH: 10
<212> TYPE: PRT
<213> ORGANISM: Artificial sequence
<220> FEATURE:
<223> OTHER INFORMATION: Synthetic amino acid

<400> SEQUENCE: 142

Gly Gly Ser Ile Ser Ser Ser Ser Tyr Tyr
1               5                   10

<210> SEQ ID NO 143
<211> LENGTH: 7
<212> TYPE: PRT
<213> ORGANISM: Artificial sequence
<220> FEATURE:
<223> OTHER INFORMATION: Synthetic amino acid
```

```
<400> SEQUENCE: 143

Ile Tyr Tyr Ser Gly Ser Thr
1               5

<210> SEQ ID NO 144
<211> LENGTH: 14
<212> TYPE: PRT
<213> ORGANISM: Artificial sequence
<220> FEATURE:
<223> OTHER INFORMATION: Synthetic amino acid

<400> SEQUENCE: 144

Ala Arg Pro Asn Ser Ser Gly Trp Ser Tyr Tyr Phe Asp Tyr
1               5                   10

<210> SEQ ID NO 145
<211> LENGTH: 10
<212> TYPE: PRT
<213> ORGANISM: Artificial sequence
<220> FEATURE:
<223> OTHER INFORMATION: Synthetic amino acid

<400> SEQUENCE: 145

Gly Gly Ser Ile Ser Arg Thr Tyr Tyr Tyr
1               5                   10

<210> SEQ ID NO 146
<211> LENGTH: 7
<212> TYPE: PRT
<213> ORGANISM: Artificial sequence
<220> FEATURE:
<223> OTHER INFORMATION: Synthetic amino acid

<400> SEQUENCE: 146

Val Tyr Tyr Ser Gly Ser Thr
1               5

<210> SEQ ID NO 147
<211> LENGTH: 11
<212> TYPE: PRT
<213> ORGANISM: Artificial sequence
<220> FEATURE:
<223> OTHER INFORMATION: Synthetic amino acid

<400> SEQUENCE: 147

Ala Ser His Glu Ser Trp Gln Gln Leu Ile Ser
1               5                   10

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000
```

-continued

```
<210> SEQ ID NO 151
<211> LENGTH: 6
<212> TYPE: PRT
<213> ORGANISM: Artificial sequence
<220> FEATURE:
<223> OTHER INFORMATION: Synthetic amino acid

<400> SEQUENCE: 151

Gln Ser Ile Ser Thr Tyr
1               5

<210> SEQ ID NO 152
<211> LENGTH: 3
<212> TYPE: PRT
<213> ORGANISM: Artificial sequence
<220> FEATURE:
<223> OTHER INFORMATION: Synthetic amino acid

<400> SEQUENCE: 152

Gly Gly Ser
1

<210> SEQ ID NO 153
<211> LENGTH: 9
<212> TYPE: PRT
<213> ORGANISM: Artificial sequence
<220> FEATURE:
<223> OTHER INFORMATION: Synthetic amino acid

<400> SEQUENCE: 153

Gln Gln Ser Tyr Ser Thr Arg Tyr Ser
1               5

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157
<211> LENGTH: 8
<212> TYPE: PRT
<213> ORGANISM: Artificial sequence
<220> FEATURE:
<223> OTHER INFORMATION: Synthetic amino acid

<400> SEQUENCE: 157

Ser Ser Asn Ile Gly Asn Asn Tyr
1               5

<210> SEQ ID NO 158
<211> LENGTH: 3
<212> TYPE: PRT
<213> ORGANISM: Artificial sequence
<220> FEATURE:
<223> OTHER INFORMATION: Synthetic amino acid
```

```
<400> SEQUENCE: 158

Asp Asn Asn
1

<210> SEQ ID NO 159
<211> LENGTH: 11
<212> TYPE: PRT
<213> ORGANISM: Artificial sequence
<220> FEATURE:
<223> OTHER INFORMATION: Synthetic amino acid

<400> SEQUENCE: 159

Gly Thr Trp Asp Ser Ser Leu Ser Ala Gly Val
1               5                   10

<210> SEQ ID NO 160
<211> LENGTH: 9
<212> TYPE: PRT
<213> ORGANISM: Artificial sequence
<220> FEATURE:
<223> OTHER INFORMATION: Synthetic amino acid

<400> SEQUENCE: 160

Ser Ser Asp Val Gly Gly Tyr Asn Tyr
1               5

<210> SEQ ID NO 161
<211> LENGTH: 3
<212> TYPE: PRT
<213> ORGANISM: Artificial sequence
<220> FEATURE:
<223> OTHER INFORMATION: Synthetic amino acid

<400> SEQUENCE: 161

Glu Val Ser
1

<210> SEQ ID NO 162
<211> LENGTH: 10
<212> TYPE: PRT
<213> ORGANISM: Artificial sequence
<220> FEATURE:
<223> OTHER INFORMATION: Synthetic amino acid

<400> SEQUENCE: 162

Ser Ser Tyr Ala Gly Ser Asn Asn Leu Val
1               5                   10

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000
```

```
<210> SEQ ID NO 166
<211> LENGTH: 9
<212> TYPE: PRT
<213> ORGANISM: Artificial sequence
<220> FEATURE:
<223> OTHER INFORMATION: Synthetic amino acid

<400> SEQUENCE: 166

Gly Ser Asp Ile Gly Gly Tyr Asn His
1               5

<210> SEQ ID NO 167
<211> LENGTH: 3
<212> TYPE: PRT
<213> ORGANISM: Artificial sequence
<220> FEATURE:
<223> OTHER INFORMATION: Synthetic amino acid

<400> SEQUENCE: 167

Gly Val Thr
1

<210> SEQ ID NO 168
<211> LENGTH: 10
<212> TYPE: PRT
<213> ORGANISM: Artificial sequence
<220> FEATURE:
<223> OTHER INFORMATION: Synthetic amino acid

<400> SEQUENCE: 168

Ser Ser Tyr Thr Asp Asn Thr Ser Trp Val
1               5                   10

<210> SEQ ID NO 169
<211> LENGTH: 6
<212> TYPE: PRT
<213> ORGANISM: Artificial sequence
<220> FEATURE:
<223> OTHER INFORMATION: Synthetic amino acid

<400> SEQUENCE: 169

Gln Ser Val Thr Thr Trp
1               5

<210> SEQ ID NO 170
<211> LENGTH: 3
<212> TYPE: PRT
<213> ORGANISM: Artificial sequence
<220> FEATURE:
<223> OTHER INFORMATION: Synthetic amino acid

<400> SEQUENCE: 170

Ser Ala Ser
1

<210> SEQ ID NO 171
<211> LENGTH: 8
<212> TYPE: PRT
<213> ORGANISM: Artificial sequence
<220> FEATURE:
<223> OTHER INFORMATION: Synthetic amino acid

<400> SEQUENCE: 171

Gln Gln Tyr Arg Phe Tyr Trp Thr
1               5
```

```
<210> SEQ ID NO 172
<211> LENGTH: 8
<212> TYPE: PRT
<213> ORGANISM: Artificial sequence
<220> FEATURE:
<223> OTHER INFORMATION: Synthetic amino acid

<400> SEQUENCE: 172

Ser Ser Asn Ile Gly Ser Asn Thr
1               5

<210> SEQ ID NO 173
<211> LENGTH: 3
<212> TYPE: PRT
<213> ORGANISM: Artificial sequence
<220> FEATURE:
<223> OTHER INFORMATION: Synthetic amino acid

<400> SEQUENCE: 173

Ser Asn Asp
1

<210> SEQ ID NO 174
<211> LENGTH: 12
<212> TYPE: PRT
<213> ORGANISM: Artificial sequence
<220> FEATURE:
<223> OTHER INFORMATION: Synthetic amino acid

<400> SEQUENCE: 174

Ser Ala Trp Asp Asp Ser Leu Asn Gly Arg Tyr Val
1               5                   10

<210> SEQ ID NO 175
<211> LENGTH: 9
<212> TYPE: PRT
<213> ORGANISM: Artificial sequence
<220> FEATURE:
<223> OTHER INFORMATION: Synthetic amino acid

<400> SEQUENCE: 175

Ser Asn Asp Val Gly Asp Tyr Asn Phe
1               5

<210> SEQ ID NO 176
<211> LENGTH: 3
<212> TYPE: PRT
<213> ORGANISM: Artificial sequence
<220> FEATURE:
<223> OTHER INFORMATION: Synthetic amino acid

<400> SEQUENCE: 176

Glu Val Thr
1

<210> SEQ ID NO 177
<211> LENGTH: 10
<212> TYPE: PRT
<213> ORGANISM: Artificial sequence
<220> FEATURE:
<223> OTHER INFORMATION: Synthetic amino acid

<400> SEQUENCE: 177

Ser Ser Tyr Ala Gly Gly Asn Ser Val Val
1               5                   10

<210> SEQ ID NO 178
```

```
<211> LENGTH: 6
<212> TYPE: PRT
<213> ORGANISM: Artificial sequence
<220> FEATURE:
<223> OTHER INFORMATION: Synthetic amino acid

<400> SEQUENCE: 178

Asn Ile Gly Ser Lys Ser
1               5

<210> SEQ ID NO 179
<211> LENGTH: 3
<212> TYPE: PRT
<213> ORGANISM: Artificial sequence
<220> FEATURE:
<223> OTHER INFORMATION: Synthetic amino acid

<400> SEQUENCE: 179

Asp Val Arg
1

<210> SEQ ID NO 180
<211> LENGTH: 11
<212> TYPE: PRT
<213> ORGANISM: Artificial sequence
<220> FEATURE:
<223> OTHER INFORMATION: Synthetic amino acid

<400> SEQUENCE: 180

Gln Val Trp Glu Ser Thr Thr Ser His Val Ile
1               5                   10

<210> SEQ ID NO 181
<211> LENGTH: 6
<212> TYPE: PRT
<213> ORGANISM: Artificial sequence
<220> FEATURE:
<223> OTHER INFORMATION: Synthetic amino acid

<400> SEQUENCE: 181

Gln Ser Val Ser Ser Asn
1               5

<210> SEQ ID NO 182
<211> LENGTH: 3
<212> TYPE: PRT
<213> ORGANISM: Artificial sequence
<220> FEATURE:
<223> OTHER INFORMATION: Synthetic amino acid

<400> SEQUENCE: 182

Gly Ala Ser
1

<210> SEQ ID NO 183
<211> LENGTH: 10
<212> TYPE: PRT
<213> ORGANISM: Artificial sequence
<220> FEATURE:
<223> OTHER INFORMATION: Synthetic amino acid

<400> SEQUENCE: 183

Gln Glu Tyr Asn Asp Trp Pro Leu Tyr Thr
1               5                   10

<210> SEQ ID NO 184
<211> LENGTH: 6
```

<212> TYPE: PRT
<213> ORGANISM: Artificial sequence
<220> FEATURE:
<223> OTHER INFORMATION: Synthetic amino acid

<400> SEQUENCE: 184

His Ser Val Gly Ser Ser
1               5

<210> SEQ ID NO 185
<211> LENGTH: 3
<212> TYPE: PRT
<213> ORGANISM: Artificial sequence
<220> FEATURE:
<223> OTHER INFORMATION: Synthetic amino acid

<400> SEQUENCE: 185

Gly Val Ser
1

<210> SEQ ID NO 186
<211> LENGTH: 9
<212> TYPE: PRT
<213> ORGANISM: Artificial sequence
<220> FEATURE:
<223> OTHER INFORMATION: Synthetic amino acid

<400> SEQUENCE: 186

Gln Gln Tyr Asp Asn Trp Pro Phe Thr
1               5

<210> SEQ ID NO 187
<211> LENGTH: 8
<212> TYPE: PRT
<213> ORGANISM: Artificial sequence
<220> FEATURE:
<223> OTHER INFORMATION: Synthetic amino acid

<400> SEQUENCE: 187

Thr Ser Asn Ile Gly Ser Asn Thr
1               5

<210> SEQ ID NO 188
<211> LENGTH: 3
<212> TYPE: PRT
<213> ORGANISM: Artificial sequence
<220> FEATURE:
<223> OTHER INFORMATION: Synthetic amino acid

<400> SEQUENCE: 188

Asn Asn Asn
1

<210> SEQ ID NO 189
<211> LENGTH: 11
<212> TYPE: PRT
<213> ORGANISM: Artificial sequence
<220> FEATURE:
<223> OTHER INFORMATION: Synthetic amino acid

<400> SEQUENCE: 189

Ala Ala Trp Asp Asp Ser Leu Asn Gly Val Val
1               5                   10

<210> SEQ ID NO 190
<211> LENGTH: 6
<212> TYPE: PRT

```
<213> ORGANISM: Artificial sequence
<220> FEATURE:
<223> OTHER INFORMATION: Synthetic amino acid

<400> SEQUENCE: 190

Asn Ile Ala Thr Phe Ser
1               5

<210> SEQ ID NO 191
<211> LENGTH: 3
<212> TYPE: PRT
<213> ORGANISM: Artificial sequence
<220> FEATURE:
<223> OTHER INFORMATION: Synthetic amino acid

<400> SEQUENCE: 191

Asp Asp Leu
1

<210> SEQ ID NO 192
<211> LENGTH: 11
<212> TYPE: PRT
<213> ORGANISM: Artificial sequence
<220> FEATURE:
<223> OTHER INFORMATION: Synthetic amino acid

<400> SEQUENCE: 192

Gln Val Trp Glu Ile Ser Ser Asp Glu Tyr Val
1               5                   10

<210> SEQ ID NO 193
<211> LENGTH: 9
<212> TYPE: PRT
<213> ORGANISM: Artificial sequence
<220> FEATURE:
<223> OTHER INFORMATION: Synthetic amino acid

<400> SEQUENCE: 193

Ser Ser Asp Val Gly Ser Tyr Asn Leu
1               5

<210> SEQ ID NO 194
<211> LENGTH: 3
<212> TYPE: PRT
<213> ORGANISM: Artificial sequence
<220> FEATURE:
<223> OTHER INFORMATION: Synthetic amino acid

<400> SEQUENCE: 194

Glu Gly Ser
1

<210> SEQ ID NO 195
<211> LENGTH: 11
<212> TYPE: PRT
<213> ORGANISM: Artificial sequence
<220> FEATURE:
<223> OTHER INFORMATION: Synthetic amino acid

<400> SEQUENCE: 195

Cys Ser Tyr Ala Gly Ser Ser Thr Phe Val Val
1               5                   10

<210> SEQ ID NO 196
<211> LENGTH: 9
<212> TYPE: PRT
<213> ORGANISM: Artificial sequence
```

```
<220> FEATURE:
<223> OTHER INFORMATION: Synthetic amino acid

<400> SEQUENCE: 196

Asn Asn Asp Val Gly Ser Tyr Asp His
1               5

<210> SEQ ID NO 197
<211> LENGTH: 3
<212> TYPE: PRT
<213> ORGANISM: Artificial sequence
<220> FEATURE:
<223> OTHER INFORMATION: Synthetic amino acid

<400> SEQUENCE: 197

Asp Val Ser
1

<210> SEQ ID NO 198
<211> LENGTH: 10
<212> TYPE: PRT
<213> ORGANISM: Artificial sequence
<220> FEATURE:
<223> OTHER INFORMATION: Synthetic amino acid

<400> SEQUENCE: 198

Cys Ser Phe Ala Gly Ser Tyr Thr Tyr Val
1               5                   10

<210> SEQ ID NO 199
<211> LENGTH: 9
<212> TYPE: PRT
<213> ORGANISM: Artificial sequence
<220> FEATURE:
<223> OTHER INFORMATION: Synthetic amino acid

<400> SEQUENCE: 199

Ser Asn Asp Val Gly Tyr Tyr Asp His
1               5

<210> SEQ ID NO 200
<211> LENGTH: 3
<212> TYPE: PRT
<213> ORGANISM: Artificial sequence
<220> FEATURE:
<223> OTHER INFORMATION: Synthetic amino acid

<400> SEQUENCE: 200

Asp Val Ser
1

<210> SEQ ID NO 201
<211> LENGTH: 10
<212> TYPE: PRT
<213> ORGANISM: Artificial sequence
<220> FEATURE:
<223> OTHER INFORMATION: Synthetic amino acid

<400> SEQUENCE: 201

Cys Ser Phe Ala Gly Ser Tyr Thr Tyr Val
1               5                   10

<210> SEQ ID NO 202
<211> LENGTH: 9
<212> TYPE: PRT
<213> ORGANISM: Artificial sequence
<220> FEATURE:
```

```
<223> OTHER INFORMATION: Synthetic amino acid

<400> SEQUENCE: 202

Ser Ser Asn Ile Gly Ala Asp Tyr Ala
1               5

<210> SEQ ID NO 203
<211> LENGTH: 3
<212> TYPE: PRT
<213> ORGANISM: Artificial sequence
<220> FEATURE:
<223> OTHER INFORMATION: Synthetic amino acid

<400> SEQUENCE: 203

Gly Thr Ile
1

<210> SEQ ID NO 204
<211> LENGTH: 12
<212> TYPE: PRT
<213> ORGANISM: Artificial sequence
<220> FEATURE:
<223> OTHER INFORMATION: Synthetic amino acid

<400> SEQUENCE: 204

Gln Ser Tyr Asp Ser Ser Leu Ser Gly Ser Val Val
1               5                   10

<210> SEQ ID NO 205
<211> LENGTH: 9
<212> TYPE: PRT
<213> ORGANISM: Artificial sequence
<220> FEATURE:
<223> OTHER INFORMATION: Synthetic amino acid

<400> SEQUENCE: 205

Ser Ser Asn Ile Gly Ala Asp Tyr Asp
1               5

<210> SEQ ID NO 206
<211> LENGTH: 3
<212> TYPE: PRT
<213> ORGANISM: Artificial sequence
<220> FEATURE:
<223> OTHER INFORMATION: Synthetic amino acid

<400> SEQUENCE: 206

Gly Asn Ile
1

<210> SEQ ID NO 207
<211> LENGTH: 12
<212> TYPE: PRT
<213> ORGANISM: Artificial sequence
<220> FEATURE:
<223> OTHER INFORMATION: Synthetic amino acid

<400> SEQUENCE: 207

Gln Ser Tyr Asp Ser Ser Leu Ser Gly Ser Val Val
1               5                   10

<210> SEQ ID NO 208
<211> LENGTH: 9
<212> TYPE: PRT
<213> ORGANISM: Artificial sequence
<220> FEATURE:
<223> OTHER INFORMATION: Synthetic amino acid
```

```
<400> SEQUENCE: 208

Ser Gly Ile Asn Val Gly Ile Tyr Arg
1               5

<210> SEQ ID NO 209
<211> LENGTH: 7
<212> TYPE: PRT
<213> ORGANISM: Artificial sequence
<220> FEATURE:
<223> OTHER INFORMATION: Synthetic amino acid

<400> SEQUENCE: 209

Tyr Lys Ser Asp Ser Asp Lys
1               5

<210> SEQ ID NO 210
<211> LENGTH: 9
<212> TYPE: PRT
<213> ORGANISM: Artificial sequence
<220> FEATURE:
<223> OTHER INFORMATION: Synthetic amino acid

<400> SEQUENCE: 210

Met Ile Trp His Ser Ser Ala Val Ala
1               5

<210> SEQ ID NO 211
<211> LENGTH: 125
<212> TYPE: PRT
<213> ORGANISM: Staphylococcus aureus

<400> SEQUENCE: 211

Val Ser Gln Ala Thr Ser Gln Pro Ile Asn Phe Gln Val Gln Lys Asp
1               5                   10                  15

Gly Ser Ser Glu Lys Ser His Met Asp Asp Tyr Met Gln His Pro Gly
            20                  25                  30

Lys Val Ile Lys Gln Asn Asn Lys Tyr Tyr Phe Gln Ala Val Leu Asn
        35                  40                  45

Asn Ala Ser Phe Trp Lys Glu Tyr Lys Phe Tyr Asn Ala Asn Asn Gln
    50                  55                  60

Glu Leu Ala Thr Thr Val Val Asn Asp Asp Lys Lys Ala Asp Thr Arg
65                  70                  75                  80

Thr Ile Asn Val Ala Val Glu Pro Gly Tyr Lys Ser Leu Thr Thr Lys
                85                  90                  95

Val His Ile Val Val Pro Gln Ile Asn Tyr Asn His Arg Tyr Thr Thr
            100                 105                 110

His Leu Glu Phe Glu Lys Ala Ile Pro Thr Leu Ala Asp
        115                 120                 125

<210> SEQ ID NO 212
<211> LENGTH: 259
<212> TYPE: PRT
<213> ORGANISM: Staphylococcus aureus

<400> SEQUENCE: 212

Ser Thr Gln Val Ser Ala Thr Ser Gln Pro Ile Asn Phe Gln Val
1               5                   10                  15

Gln Lys Asp Gly Ser Ser Glu Lys Ser His Met Asp Asp Tyr Met Gln
            20                  25                  30

His Pro Gly Lys Val Ile Lys Gln Asn Asn Lys Tyr Tyr Phe Gln Ala
```

```
                    35                  40                  45
Val Leu Asn Asn Ala Ser Phe Trp Lys Glu Tyr Lys Phe Tyr Asn Ala
    50                  55                  60

Asn Asn Gln Glu Leu Ala Thr Thr Val Val Asn Asp Lys Lys Ala
65                  70                  75                  80

Asp Thr Arg Thr Ile Asn Val Ala Val Glu Pro Gly Tyr Lys Ser Leu
                85                  90                  95

Thr Thr Lys Val His Ile Val Val Pro Gln Ile Asn Tyr Asn His Arg
            100                 105                 110

Tyr Thr Thr His Leu Glu Phe Glu Lys Ala Ile Pro Thr Leu Ala Asp
        115                 120                 125

Ala Ala Lys Pro Asn Asn Val Lys Pro Val Gln Pro Lys Pro Gly Gln
    130                 135                 140

Pro Lys Thr Pro Thr Glu Gln Thr Lys Pro Val Gln Pro Lys Val Glu
145                 150                 155                 160

Lys Val Lys Pro Ala Val Thr Ala Pro Ser Lys Ala Glu Asn Thr Gln
                165                 170                 175

Thr Thr Lys Val Val Ser Thr Glu Ala Thr Lys Asp Gln Ser Gln Thr
            180                 185                 190

Gln Ser Ala Arg Thr Val Lys Thr Thr Gln Thr Ala Gln Glu Gln Asn
        195                 200                 205

Lys Val Gln Thr Pro Val Lys Asp Val Ala Thr Ala Lys Ser Glu Ser
    210                 215                 220

Asn Asn Gln Ala Val Ser Asp Asn Lys Ser Gln Gln Thr Asn Lys Val
225                 230                 235                 240

Thr Lys Gln Asn Glu Val His Lys Gln Gly Pro Ser Lys Asp Ser Lys
                245                 250                 255

Ala Lys Glu

<210> SEQ ID NO 213
<211> LENGTH: 20
<212> TYPE: DNA
<213> ORGANISM: Artificial sequence
<220> FEATURE:
<223> OTHER INFORMATION: Synthetic phosphorothioate-modified
      oligodeoxynucleotide
<220> FEATURE:
<221> NAME/KEY: modified_base
<222> LOCATION: (1)..(19)
<223> OTHER INFORMATION: phosphorothioate base

<400> SEQUENCE: 213
cgtcgttttt cggtcgtttt                                              20
```

UNITED STATES PATENT AND TRADEMARK OFFICE
CERTIFICATE OF CORRECTION

| | |
|---|---|
| PATENT NO. | : 11,992,520 B2 |
| APPLICATION NO. | : 17/276361 |
| DATED | : May 28, 2024 |
| INVENTOR(S) | : James E. Crowe, Jr. and Eric Skaar |

It is certified that error appears in the above-identified patent and that said Letters Patent is hereby corrected as shown below:

In the Claims

In Claim 13, Column 184, Line 10, delete ", or genetic delivery with an RNA or DNA sequence or vector encoding the antibody fragment" and insert -- . -- therefor.

Signed and Sealed this
Sixth Day of August, 2024

Katherine Kelly Vidal
*Director of the United States Patent and Trademark Office*